(12) United States Patent
Gosselin et al.

(10) Patent No.: US 7,138,376 B2
(45) Date of Patent: Nov. 21, 2006

(54) METHODS AND COMPOSITIONS FOR TREATING HEPATITIS C VIRUS USING 4'-MODIFIED NUCLEOSIDES

(75) Inventors: Gilles Gosselin, Montpellier (FR); Jean-Louis Imbach, Montpellier (FR); Jean-Pierre Sommadossi, Cambridge, MA (US)

(73) Assignees: Idenix Pharmaceuticals, Inc., Cambridge, MA (US); Centre National de la Recherche Scientifique, Paris (FR)

( * ) Notice: Subject to any disclaimer, the term of this patent is extended or adjusted under 35 U.S.C. 154(b) by 19 days.

(21) Appl. No.: 10/261,244

(22) Filed: Sep. 30, 2002

(65) Prior Publication Data

US 2004/0006007 A1    Jan. 8, 2004

Related U.S. Application Data

(60) Provisional application No. 60/326,184, filed on Sep. 28, 2001.

(51) Int. Cl.
*A61K 31/70* (2006.01)
*A61K 38/14* (2006.01)
*A61K 31/7076* (2006.01)
*C07K 9/00* (2006.01)
*C07H 19/067* (2006.01)

(52) U.S. Cl. .................. 514/43; 514/18; 514/422; 514/894; 514/2; 514/12; 514/312; 514/314; 514/21; 514/269; 514/339; 514/370; 514/42; 514/423; 514/425; 536/23.1; 536/23.72; 536/23.4; 536/24.5; 536/24.32; 435/5; 435/6; 435/69.1; 424/228.1; 424/85.4; 424/85.7; 546/153; 546/171; 546/276.4; 548/523; 548/517

(58) Field of Classification Search .................. 514/43, 514/18, 422, 894, 2, 12, 312, 314, 21, 269, 514/339, 370, 42, 423, 425; 536/23.1, 23–72, 536/23.4, 24.5, 24.32; 435/5, 6, 671; 424/228.1, 424/85.4, 85.7; 546/153, 171, 276.4; 548/523, 548/517; 544/283
See application file for complete search history.

(56) References Cited

U.S. PATENT DOCUMENTS

| | | |
|---|---|---|
| 3,798,209 A | 3/1974 | Witkowski et al. |
| RE29,835 E | 11/1978 | Witkowski et al. |
| 4,522,811 A | 6/1985 | Eppstein et al. |
| 4,957,924 A | 9/1990 | Beauchamp |
| 5,026,687 A | 6/1991 | Yarchoan |
| 5,149,794 A | 9/1992 | Yatvin et al. |
| 5,157,027 A | 10/1992 | Biller et al. |
| 5,194,654 A | 3/1993 | Hostetler et al. |
| 5,223,263 A | 6/1993 | Hostetler et al. |
| 5,256,641 A | 10/1993 | Yatvin et al. |

(Continued)

FOREIGN PATENT DOCUMENTS

DE        3512781        10/1985

(Continued)

OTHER PUBLICATIONS

Alt M. et al., *Archives of Virology*, 1997, 142, 589-599.

(Continued)

*Primary Examiner*—Shaojia Anna Jiang
*Assistant Examiner*—Devesh Khare
(74) *Attorney, Agent, or Firm*—Sherry M. Knowles, Esq.; King & Spalding LLP

(57) ABSTRACT

A compound, method and composition for treating a host infected with a hepatitis C viral comprising administering an effective hepatitis C treatment amount of a described 4'-disubstituted nucleoside or a pharmaceutically acceptable salt or prodrug thereof, is provided.

31 Claims, 4 Drawing Sheets

U.S. PATENT DOCUMENTS

| | | |
|---|---|---|
| 5,372,808 A | 12/1994 | Blatt |
| 5,411,947 A | 5/1995 | Hostetler et al. |
| 5,463,092 A | 10/1995 | Hostetler et al. |
| 5,491,135 A | 2/1996 | Blough |
| 5,496,546 A | 3/1996 | Wang |
| 5,538,865 A | 7/1996 | Reyes |
| 5,543,389 A | 8/1996 | Yatvin et al. |
| 5,543,390 A | 8/1996 | Yatvin et al. |
| 5,543,391 A | 8/1996 | Yatvin et al. |
| 5,554,728 A | 9/1996 | Basava et al. |
| 5,597,691 A | 1/1997 | Houghton et al. |
| 5,610,054 A | 3/1997 | Draper |
| 5,633,358 A | 5/1997 | Gruetzke et al. |
| 5,633,388 A | 5/1997 | Diana |
| 5,676,942 A | 10/1997 | Testa et al. |
| 5,725,859 A | 3/1998 | Omer |
| 5,738,845 A | 4/1998 | Imakawa |
| 5,738,985 A | 4/1998 | Miles et al. |
| 5,739,002 A | 4/1998 | De Francesco et al. |
| 5,759,795 A | 6/1998 | Jubin |
| 5,830,455 A | 11/1998 | Valtuena |
| 5,830,905 A | 11/1998 | Diana et al. |
| 5,837,257 A | 11/1998 | Tsai et al. |
| 5,846,964 A | 12/1998 | Ozeki |
| 5,849,696 A | 12/1998 | Chretien et al. |
| 5,849,800 A | 12/1998 | Smith |
| 5,858,389 A | 1/1999 | Elsherbini |
| 5,861,267 A | 1/1999 | Su |
| 5,869,253 A | 2/1999 | Draper |
| 5,891,874 A | 4/1999 | Colacino et al. |
| 5,908,621 A | 6/1999 | Glue et al. |
| 5,922,757 A | 7/1999 | Chojkier |
| 5,922,857 A | 7/1999 | Han et al. |
| 5,928,636 A | 7/1999 | Alber et al. |
| 5,942,223 A | 8/1999 | Bazer et al. |
| 5,969,109 A | 10/1999 | Bona et al. |
| 5,972,347 A | 10/1999 | Eder |
| 5,980,884 A | 11/1999 | Blatt |
| 5,990,276 A | 11/1999 | Zhang et al. |
| 6,001,799 A | 12/1999 | Chretien |
| 6,001,990 A | 12/1999 | Wands et al. |
| 6,004,933 A | 12/1999 | Spruce et al. |
| 6,010,848 A | 1/2000 | Delvecchio et al. |
| 6,030,785 A | 2/2000 | Katze et al. |
| 6,030,960 A | 2/2000 | Morris-Natschke |
| 6,034,134 A | 3/2000 | Gold et al. |
| 6,043,077 A | 3/2000 | Barber et al. |
| 6,056,961 A | 5/2000 | Lavie |
| 6,312,662 B1 | 11/2001 | Erion et al. |
| 6,348,587 B1 | 2/2002 | Schinazi et al. |
| 6,495,677 B1 | 12/2002 | Ramasamy et al. |
| 6,573,248 B1 | 6/2003 | Ramasamy et al. |
| 6,660,721 B1 | 12/2003 | Devos et al. |
| 6,777,395 B1 | 8/2004 | Bhat et al. |
| 6,784,166 B1 | 8/2004 | Devos et al. |
| 6,846,810 B1 | 1/2005 | Martin et al. |
| 6,911,424 B1 | 6/2005 | Schinazi et al. |
| 2002/0095033 A1 | 7/2002 | Ramasamy et al. |
| 2002/0147160 A1 | 10/2002 | Bhat et al. |
| 2002/0198171 A1 | 12/2002 | Schinazi et al. |
| 2003/0008841 A1 | 1/2003 | Devos et al. |
| 2003/0083307 A1 | 5/2003 | Devos et al. |
| 2003/0225029 A1 | 12/2003 | Stuyver et al. |
| 2003/0236216 A1 | 12/2003 | Devos et al. |
| 2004/0002476 A1 | 1/2004 | Stuyver et al. |
| 2004/0023921 A1 | 2/2004 | Yao et al. |
| 2004/0059104 A1 | 3/2004 | Cook et al. |
| 2004/0063658 A1 | 4/2004 | Roberts et al. |
| 2004/0067901 A1 | 4/2004 | Bhat et al. |
| 2004/0072788 A1 | 4/2004 | Bhat et al. |
| 2004/0110717 A1 | 6/2004 | Bhat et al. |
| 2004/0110718 A1 | 6/2004 | Devos et al. |
| 2004/0121980 A1 | 6/2004 | Martin et al. |
| 2004/0147464 A1 | 7/2004 | Roberts et al. |
| 2004/0266722 A1 | 12/2004 | Devos et al. |
| 2005/0119200 A1 | 6/2005 | Roberts et al. |

FOREIGN PATENT DOCUMENTS

| | | |
|---|---|---|
| DE | 19914474 | 10/1999 |
| EP | 0180276 | 12/1988 |
| EP | 0350287 | 10/1990 |
| EP | 0 650 371 | 5/1995 |
| EP | 0747389 | 12/1996 |
| EP | 0350287 | 9/2000 |
| GB | 1163102 | 9/1969 |
| GB | 1163103 | 9/1969 |
| GB | 1209654 | 10/1970 |
| JP | 06080688 | * 3/1994 |
| JP | 08268890 | 10/1996 |
| WO | WO 89/02733 | 4/1989 |
| WO | WO 90/00555 | 1/1990 |
| WO | WO 91/6920 | 11/1991 |
| WO | 91/19721 | 12/1991 |
| WO | WO 91/18914 | 12/1991 |
| WO | WO 93/00910 | 1/1993 |
| WO | WO 94/26273 | 11/1994 |
| WO | WO 96/15132 | 5/1996 |
| WO | WO 97/12033 | 4/1997 |
| WO | WO 97/36554 | 10/1997 |
| WO | WO 98/17679 | 4/1998 |
| WO | WO 98/19670 | * 5/1998 |
| WO | WO 99/07734 | 2/1999 |
| WO | WO 99/15194 | 4/1999 |
| WO | WO 99/29350 | 6/1999 |
| WO | WO 99/43691 | 9/1999 |
| WO | WO 99/45016 | 9/1999 |
| WO | WO 99/59621 | 11/1999 |
| WO | WO 99/64016 | 12/1999 |
| WO | WO 00/24355 | 5/2000 |
| WO | WO 00/37110 | 6/2000 |
| WO | WO 00/52015 | 9/2000 |
| WO | WO 01/81359 | 11/2000 |
| WO | WO 01/18013 | 3/2001 |
| WO | WO 01/32153 | 5/2001 |
| WO | WO 01/47935 | 7/2001 |
| WO | WO 01/60315 | 8/2001 |
| WO | WO 01/79246 | 10/2001 |
| WO | WO 01/90121 | 11/2001 |
| WO | WO 01/92282 | 12/2001 |
| WO | WO 01/96353 | 12/2001 |
| WO | WO 02/18404 | 3/2002 |
| WO | WO 02/32414 | 4/2002 |
| WO | WO 02/32920 | 4/2002 |
| WO | WO 02/48165 | 6/2002 |
| WO | WO 02/057287 | 7/2002 |
| WO | WO 02/057425 | 7/2002 |
| WO | WO 03/024461 | 3/2003 |
| WO | WO 03/051899 | 6/2003 |
| WO | WO 03/061385 | 7/2003 |
| WO | WO 03/061576 | 7/2003 |
| WO | WO 03/062255 | 7/2003 |
| WO | WO 03/062256 | 7/2003 |
| WO | WO 03/062257 | 7/2003 |
| WO | WO 04/000858 | 12/2003 |
| WO | WO 04/003138 | 1/2004 |
| WO | WO 04/007512 | 1/2004 |
| WO | WO 04/009020 | 1/2004 |

OTHER PUBLICATIONS

Battaglia, A.M. et al., *Ann. Pharmacother*, 2000, 34, 487-494.
Berenguer, M. et al. *Antivir. Ther.*, 1998, 3 (Suppl. 3), 125-136).
Chu M. et al., *Tetrahedron Letters*, 1996, 37, 7229-7232.
Ferrari R. et al. *Journal of Virology*, 1999, 73, 1649-1654.

Galderisi U. et al., *Journal of Cellular Physiology*, 1999, 181, 251-257.

Ikeda N et al., *Agent for the prevention and treatment of hepatitis C*, Japanese Patent Pub. JP-08268890, Oct. 15, 1996.

Kai Y. et al. *Prevention and treatment of viral diseases*, Japanese Patent Pub. JP-10101591, 1998.

Kakiuchi N. et al. *J. EBS Letters 421*, 217-220.

Lohmann V. et al., *Virology*, 1998, 249,108-118.

Maccjak, D. J. et al., *Hepatology* 1999, 30, abstract 995.

Qasim M.A. et al., *Biochemistry*, 1997, 36, 1598-1607.

Sudo, K. et al. (1998) *Antiviral Chemistry and Chemotherapy* 9:186.

Sudo, K. et al., (1997) *Biochemical and Biophysical Research Communications*, 238:643-647.

Sudo, K. et al. (1996) *Antiviral Research* 32:9-18.

Takeshita N. et al. *Analytical Biochemistry*, 1997, 247, 242-246.

Boyer, N. et al. *J. Hepatol.* 32:98-112, 2000.

Di Besceglie, A. M. and Bacon, B. R., *Scientific American*, Oct.: 80-85, (1999).

The Merck Manual, ch. 69, p. 901, 16th ed., (1992).

Rice, C. M. Flaviviridae: The viruses and their replication. *In*: Fields Virology, Editors: Fields, B. N., Knipe, D. M., and Howley, P. M., Lippincott-Raven Publishers, Philadelphia, PA, Chapter 30, 931-959, 1996.

Gary L. Davis. *Gastroenterology* 118:S104-S114, 2000.

Bymock et al. in *Antiviral Chemistry & Chemotherapy*, 11:2; 79-95 (2000).

Awano, H., et al., "Nucleosides and nucleotides. Part 144. Synthesis and antiviral activity of 5-substituted (2'S)-2'-C-methylcytidines and -uridines," *Archiv der Pharmazie*, VCH Verlagsgesellschaft mbh, Weinheim, DE. 329 :66-72 (Feb. 1, 1996).

Baginski, S. G, et al., "Mechanism of action of a pestivirus antiviral compound," *PNAS USA*, 97(14) : 7981-7986 (2000).

Battaglia, A.M. et al.,"Combination Therapy with Interferon and Ribavirin in the Treatment of Chronic Hepatitis C Infection", *Ann. Pharmacother*, 34:487-494 (2000).

Beigelman, L.N., et al., "A general method for synthesis of 3'-C-alkylnucleosides," *Nucleic Acids Symp. Ser.*, 9:115-118 (1981).

Berenguer, M. et al., "Hepatitis C virus in the transplant setting", *Antivir. Ther. 3 (Suppl 3)* :125-136 (1998).

Berman, E, et al., "Synergistic cytotoxic effect of azidothymidine and recombinant interferon alpha on normal human bone marrow progenitor cells," *Blood*, 74(4):1281-1286 (1989).

Bhat et al. (Oral Session V, Hepatitis C Virus, Flaviviridae, 2003 (Oral Session V, Hepatitis C Virus, Flaviviridae; 16th International Conference on Antiviral Research (Apr. 27, 2003, Savannah, Ga.); p A75).

Browne, M.J., et al., "2', 3'-didehydro-3'-deoxythmidine (d4T) in patients with AIDS or AIDS-Related Complex: A Phase I trial," *J. Infect. Dis.*, 167(1):21-29 (1993).

Cappellacci, L., et al., "Ribose-modified nucleosides as ligands for adenosine receptors: Synthesis, conformational analysis, and biological evaluation of 1'-C-methyl adenosine analogues," *J. Med. Chem.*, 45:1196-1202 (2002).

Colacino, J. M., "Review article: Mechanisms for the anti-hepatitis B virus activity and mitochondrial toxicity of fialurdine (FIAU)," *Antiviral Res.*, 29(2-3): 125-39 (1996).

Cui, L., et al., "Cellular and molecular events leading to mitochondrial toxicity of 1-(2-deoxy-2-fluoro-1β-D-arabinofuranosyl)-5-iodouracil in human liver cells," *J. Clin. Invest.*, 95:555-563 (1995).

Davis, G.L., "Current therapy for chronic Hepatitis C." *Gastroenterology*118:S104-S114 (2000).

De Francesco, R., et al., "Approaching a new era for hepatitis C virus therapy: inhibitors of the NS3-4A Serine protease and the NS5B RNA-dependent RNA polymerase," *Antiviral Research*, 58: 1-16 (2003).

De Lombaert, S., et al., "N-Phosphonomethyl dipeptides and their phosphonate prodrugs, a new generation of neutral endopeptidase (NEP, EC 3.4.24.11) inhibitors," *J. Med. Chem.*, 37:498-511 (1994).

Dornsife, R.E., et al, "In vitro potency of inhibition by antiviral drugs of hematopoietic progenitor colony formation correlates with exposure at hemotoxic levels in Human immunodeficiency Virus-positive humans," *Antimicrob. Agents Chemother.*, 40(2):514-519 (1996).

Dymock, B.W., et al., "Review: Novel approaches to the treatment of hepatitis C virus infection," *Antiviral Chemistry & Chemotherapy*, 11(2):79-95 (2000).

Eldrup et al. (Oral Session V, Hepatitis C Virus, Flaviviridae; 16[th]International Conference on Antiviral Research (Apr. 27, 2003, Savannah, Ga.).

Farkas, J., et al., "Nucleic acid components and their analogues. XCIV, Synthesis of 6-amino-9-(1-deoxy-β-D-psicofuranosyl)purine", *Collect. Czech. Chem. Commun.* 32:2663-2667 (1967).

Farkas, J., et al., "Nucleic acid components and their analogues. LXXIX. Synthesis off methyl 1-deoxy-D-psicofuranosides substituted at $C_{(1)}$with halo atoms or a mercapto group," *Collect. Czech. Chem. Commun.*, 31:1535-1543 (1996).

Farquhar, D., et al., "Synthesis and biological evaluation of neutral derivatives of 3-fluoro-2'-deoxyuridine 5'-phosphate," *J. Med. Chem.* 26: 1153 (1983).

Farquhar, D., et al., "Synthesis and biological evaluation of 9-[5'-(2-oxo-1, 3, 2-oxazaphosphorinan-2-yl)-β-D-arabinosyl]adenine and 9-[5'-(2-oxo-1, 3, 2-dioxazaphosphorinan-2-yl)-β-D-arabinsoyl]adenine: Potential neutral precursors of 9-[β-D-arabinofuranosyl]adenine 5'-monophosphate," *J. Med. Chem.* 28:1358-1381 (1985).

Fedorov, I.I., et al., "3'-C-branched 2'-deoxy-5-methyluridines: Synthesis, enzyme inhibition, and antiviral properties," *J. Med. Chem.*, 35:4567-4575 (1992).

Ferrari R., et al., "Characterization of soluble hepatitis C virus RNA-dependent RNA polymerase expressed in *Escherichia coli*," *Journal of Virology*, 73(2), 1649-1654 (1999).

Fischl, M.A., et al., "Zalcitabine compared with zidovudine in patients with advanced HIV-1 infection who received previous zidovudine therapy," *Ann. Intern. Med.*, 18(10):762-769 (1993).

Franchetti, P., et al., "2'-C-Methyl analogues of selective adenosine receptor agonists: synthesis and binding studies," *J. Med. Chem.*, 41(10):1708-1715 (1998).

Freed, J.J., et al., "Evidence for acyloxymethyl esters of pyrimidine 5'-deoxyribonucleotides as extracellular sources of ative 5'-deoxyribonucleotides in cultured cells," *Biochemical Pharmacology*. 38:3193-3198 (1989).

Gunic, E., et al., "Synthesis and cytotoxicity of 4'-C-and 5'-C-substituted Toyocamycins,"*Bioorg. Med. Chem.*, 9:163-170 (2001).

Harry-O'Kuru, R.E., J.M. Smith, and M.S. Wolfe, "A short, flexible route towar 2'-C-branched ribonucleosides", *J. Org. Chem.* 62, 1754-1759 (1997). (Scheme 11).

Hattori, H., et al., "Nucleosides and nucleotides. 158.," *J. Med. Chem.*, 39:5005-5011 (1996).

Hostetler, K.Y., et al., "Synthesis and antiretroviral activity of phospholipids analogs of azidothymidine and other antiviral nucleosides," *J. Biol. Chem.*, 265:6112-6117 (1990).

Hostetler, K. Y., et al., "Greatly enhanced inhibition of Human Immunodeficiency Virus Type I replication in CEM and HT4-6C cells by 3'-deoxythmidine diphosphate dimyristoylglycerol, a lipid prodrug of 3'-deoxythmidine," *Antimicrob. Agents Chemother.*, 36:2025.2029 (Sep. 1992).

Hrebabecky, H., et al., "Nucleic acid components and their analogues. CXLIX. Synthesis of pyrimidine nucleosides derived from 1-deoxy-D-psicose," *Collect. Czech. Chem. Commun.*, 37:2059-2065 (1972).

Hrebabecky, H., et al. "Synthesis of 7- and 9β-D-psicofuranosylguanine and their 1'-deoxy derivatives," *Collect. Czech. Chem. Commun.*, 39:2115-2123 (1974).

Hunston, R.N., et al., "Synthesis and biological properties of some cyclic phosphotriesters drived from 2'-deoxy-5-fluorouridine," *J. Med. Chem.* 37:440-444 (1984).

Johnson, C.R., et al, "3'-C-Trifluoromethyl ribonucleosides," *Nucleosides & Nucleotides*, 14(1&2):185-194 (1995).

Jones, G. H.; Moffatt, J. G., *Methods in Carbohydrate Chemistry*; Whisler, R.L. and Moffatt, J. L. Eds; Academic Press: New York, 1972; 315-322.

Jones, G. H., et al., "4'-substituted nucleosides. 5. Hydroxymethylatin of nucleoside 5'-aldehydes," *J. Org. Chem.*, 44:1309-1317 (1979).

Khamnei, S., "Neighboring group catalysis in the design of nucleotide prodrugs," *J. Med. Chem.*, 39:4109-4115 (1996).

Kucera, L.S., et al., "Novel membrane-interactive rther lipid analogs that inhibit infectious HIV-1 production and induce defective virus formation," *AIDS Res. Hum. Retro Viruses*, 6:491-501 (1990).

Kurtzberg J., et al., "Differential toxicity of carbovir and AZT to human bone marrow hematopoietic progenitor cells in vitro," *Exp. Hematol.*, 18(10):1094-1096 (1990).

Leonard, N. J., et al., "5-Amino-5-deoxyribose derivatives. Synthesis and use in the preparation of "reversed" nucleosides" *J. Heterocycl. Chem.*, 3:485-489 (Dec. 1966).

Lerza, R, et al., "In vitro synergistic inhibition of human bone marrow hemopoietic progenitor growth by a 3'-azido-3'-deoxythymidine, 2'-dideoxycytidine combination," *Exp. Hematol.*, 25(3):252-255 (1997).

Lewis W, et al., "Zidovudine induces molecular, biochemical, and ultrastructural changes in rat skeletal muscle mitochondria," *J. Clin. Invest.*, 89(4):1354-1360 (1992).

Lewis, L. D., et al., "Ultrastructural changes associated with reduced mitochondrial DNA and impaired mitochondrial function in the presence of 2'3'-dideoxycytidine," *Antimicrob. Agents Chemother.*, 36(9):2061-2065 (1992).

Lewis, W., et al., "Fialuridine an dits metabolites inhibit DNA polymerase γ at sites of ultiple adacent analog incorporation, decrease mtDNA abundance, and cause mitochondrial structural defects in cultured hepatoblasts," *Proceedings of the National Academy of Sciences, USA*. 93(8): 3592-7 (1996).

Li, Nan.-Sheng., et al., "2'-C-branched ribonucleosides. 2. Synthesis of 2'-C-γ-trifluoromethyl pryimidine ribonucleosides," *Organic Letters*, 3(7):1025-1028 (2001).

Lohmann V., et al., "Biochemical and kinetic analyses of NS5B RNA-dependent RNA polymerase of the Hepatitis C virus," *Virology*, 249, 108-118 (1998).

Luh, T.-Y., et al.,"A convenient method for the selective esterification of amino-alcohols," *Synthetic Communications*, 8(5):327-333 (1978).

Matsuda, A., et al., "Radical deoxygenation of tert-alcohols in 2'-branched-chain sugar pyrimidine nucleosides: Synthesis and antileukemic activity of 2' (S)-methylctidine," *Chem. Pharm. Bull.*, 35(9):3967-3970 (1987).

Matsuda, A., et al., "Nucleosides and Nucleotides. 94. Radical deoxygenation of tert-alcohols in 1-(2-C-alkylpentofuranosyl)pyrimidines: Synthesis of (2'S)-2'-deoxy-2'-C-methylcytidine, an antileukemic nucleoside," *J. Med. Chem.*, 34:234-239 (1991).

McCormick, J., et al., "Structure and total synthesis of HF-7, a neuroactive glyconucleoside disulfate from he funnel-web spide *Hololena curta*," *J. Am. Chem. Soc.*, 12(24), 5661-5664 (1999).

McKenzie, R., et al., "Hepatic failure and lactic acidosis due to fialuridine (FIAU), an investigational nucleoside analogue for chronic hepatitis B", *N. Engl. J. Med.*, 333(17):1099-1105 (1995).

Medina, D. J., et al., "Comparison of mitochondrial morphology, mitochondrial DNA content, and cell viability in cultured cells treated with three anti-Human Immunodeficiency Virus dideoxynucleosides," *Antimicrob. Agents Chemother.*, 38(8):1824-8 (1994).

Meier, C., et al., "Cyclic saligenyl phosphotriesters of 2',3'-didehydrothymidine (d4T)—A new pro-nucleic approach." *Bioorganic & Med. Chem. Letters*7(2):99-104 (1997).

Meyer, R.B., Jr., et al., "2'-O-Acyl-6-thioinosine cyclic 3',5'-phosphates as prodrugs of thioinosinic acid," *J. Med. Chem.* 22: 811-815 (1979).

Mikhailov, S.N., et al., "Synthesis and properties of 3'C-methylnucleosides and their phosphoric esters," *Carbohydrate Research*, 124:75-96 (1983).

Mural, Y., et al., "A synthesis and an X-ray analysis of 2'-C- and 5'-C-methylsangivamycins," *Heterocycles*, 1(33):391-404 (1992).

Neidlein, R., et al., "Mild preparationof 1-benzyuloxyiminoalkylphosphonic dichlorides: Application to the synthesis of cyclic phosphonic diesters and cyclic monoester amides," *Heterocycles*35:1185-1203 (1993).

Nutt, R.F., et al., "Branched-chain sugar nucleosides. III. 3'-C-methyladenine", *J. Org. Che..*, 33:1789-1795 (1968).

Ong, S.P., et al, "Synthesis of 3'-C-methyladenosine and 3'-C-methyluridine diphosphates and their interaction with the ribonucleoside diphosphate reductase from *Corynebacterium nephridii*," *Biochemistry,*, 31(45):11210-11215 (1992).

Olsen, et al. (Oral Session V, Hepatitis C Virus, Flaviviridae; 16[th]International Conference on Antiviral Research (Apr. 27, 2003, Savannah, Ga.) p A76).

Pan-Zhou, X-R, et al., "Differential effects of antiretroviral nucleoside analogs on mitochondrial function in HepG2 cells," *Antimicrob. Agents Chemother*. 44:496-503 (2000).

Piantadosi, C., et al., "Synthesis and evaluation of novel ether lipid nucleoside conjugates for anti-HIV-1 activity," *J. Med. Chem.* 34:1408-1414 (1991).

Richman, D.D., et al., "The toxicity of azidothymidine (AZT) in the treatment of patients with AIDS and AIDS-Related Complex," *N. Engl. J. Med.*, 317(4):192-197 (1987).

Rosenthal, A., et al., Branched-chain sugar nucleosides. Synthesis of 3'-C-ethyl (and 3'-C-butyl)uridine *Carbohydrate Research*, 79:235-242 (1980).

Schmit, C., "Synthesis of 2'-α-monofluromethyl and trifluoromethylnucleosides," *Synlett*, Thieme Verlag, Stuttgart, DE, (4):241-242 (1994).

Sharma, P.K., et al., "Synthesis of 3'-trifluoromethyl nucleosides as potenial antiviral agents," *Nucleosides, Nucleotides and Nucleic Acids*, 19(4):757-774 (2000).

Sommadossi J-P, et al., "Comparison of cytotoxicity of the (-)- and (#)- enantiomer of 2', 3'- dideoxy-3'-thiacytidine in normal human bone marrow progenitor cells," *Biochemical Pharmacology*44(10):1921-1925 (1992).

Sommadossi J.-P., et al., "Toxicity of 3'-azido-3'-deoxythymidine and 9-(1, 3-dihydroxy-2-propoxymethyl)guanine for normal human hematopoietic progenitor cells in vitro," *Antimicrobial Agents and Chemotherapy*, 31:452-454 (1987).

Starrett, J.E. Jr., et al., "Synthesis oral bioavailability determination, and *In vitro*evaluation of prodrugs of the antiviral agents 9-(2-(phosphononomethoxy)ethyl)adenine (PMEA)," *J. Med. Chem.* 37: 1857-1864 (1994).

Tronchet, J.M.J.; et al., "72. Synthesis et désamination enzymatique des C-hydroxyméthyl-3'-et C-méthyl-3'-beta-D-xylofurannosyl-9-adénin es," *Helv. Chim. Acta*, 62:689-695 (1979).

Weinberg, R.S., et al., "Effect of antiviral drugs and hematopoietic growth factors on *in vitro*erythropoiesis," *Mt. Sinai J. Med.* 1998;65(1):5-13.

Wolf, J., et al., "New 2'-C-branched-chain sugar nucleosides analogs with potential antiviral or antitumor activity," *Synthesis*, Georg Thieme Verlag, Stuttgart, DE, (8):773-778 (Aug. 1992).

Yarchoan, R., et al. "Long-term toxicity / activity profile /of 2', 3'-dideoxyinosine in AIDS or AIDS-related complex," *The Lancet*, 336(8714):526-529 (1990).

Yoshida Y, et al., "Reversal of azidothymidine-induced bone marrow suppression by 2',3'- dideoxythymidine as studied by hemopoietic clonal culture," *AIDS Res. Hum. Retroviruses*, 6(7):929-932 (1990).

Zon, G., "Cyclophosphamide Analogues," Chapter 4 in Progress in Medicinal Chemistry, vol. 19, G.P. Ellis and G.B. West, Eds., pp. 205-246 (1982).

* cited by examiner

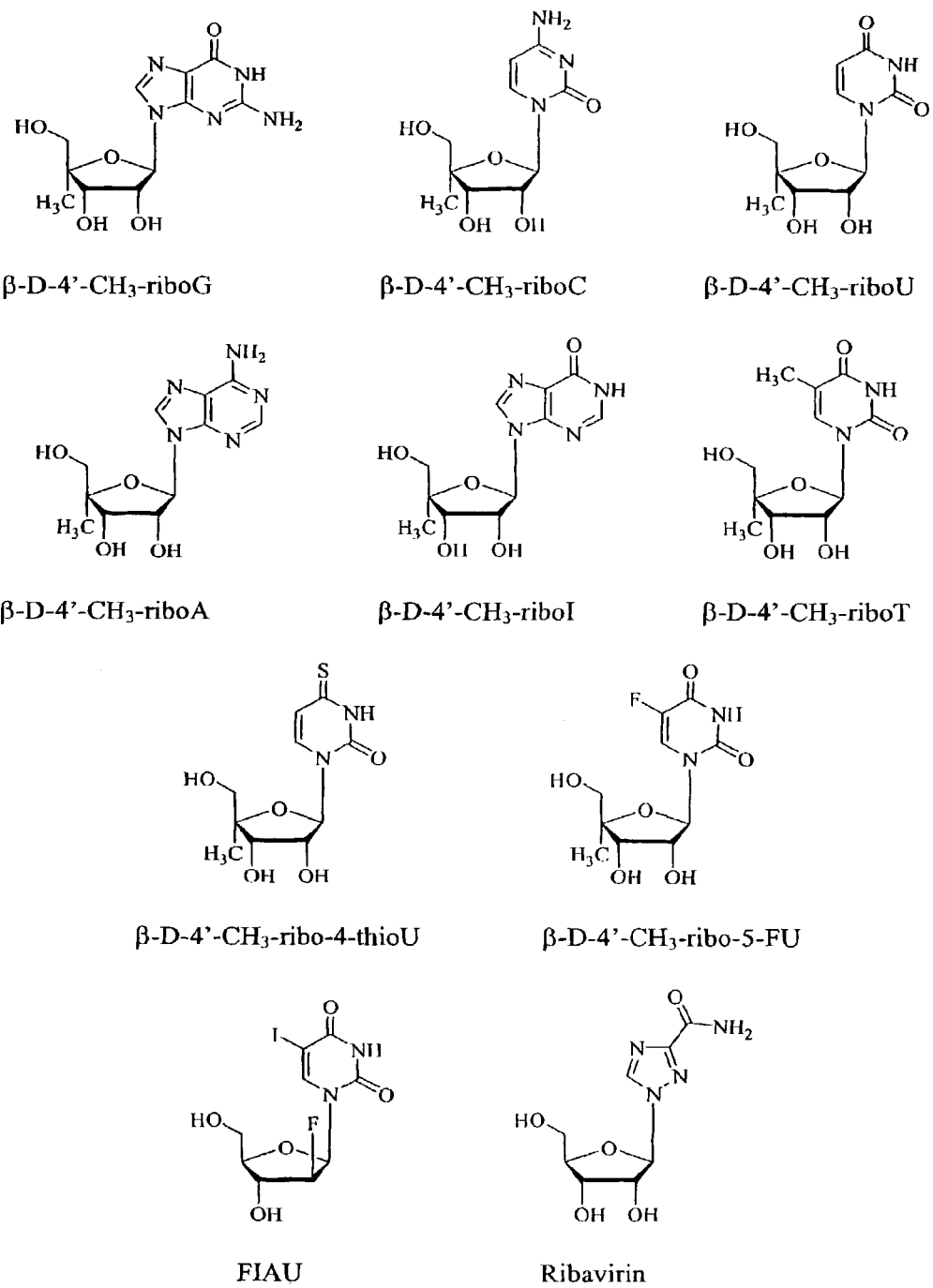
FIGURE 1/5: CHEMICAL STRUCTURES OF ILLUSTRATIVE NUCLEOSIDES

FIGURE 2/5: PREPARATION OF THE PROTECTED 4-C-METHYL-D-RIBOFURANOSE (7)
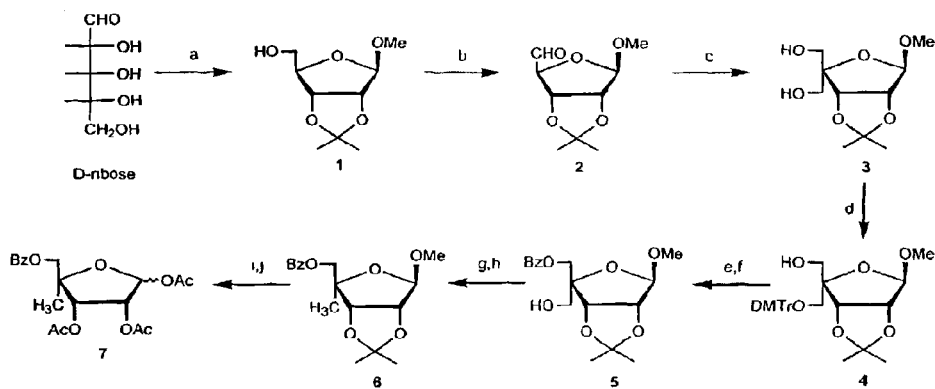
Reagents and conditions: (a) Me₂CO, 2,2-dimethoxypropane, MeOH/HCl; (b) DMSO, DCC, H₃PO₄, benzene/pyridine, r.t.; (c) CH₂O, 2N aqueous NaOH, dioxane, r.t; (d) DMTrCl, pyridine, 4°C to r.t.; (e) C₆H₅COCl, pyridine, r.t.; (f) 80% CH₃CO₂H, r.t.; (g) PhOC(S)Cl, DMAP, acetonitrile, r.t.; (h) ACCN, TMSS, toluene, reflux; (i) 80% CH₃CO₂H, 100°C; (j) Ac₂O, DMAP, pyridine, r.t.

FIGURE 3/5: SYNTHESIS OF COMPOUNDS 9, 11, 12, 14 AND 17
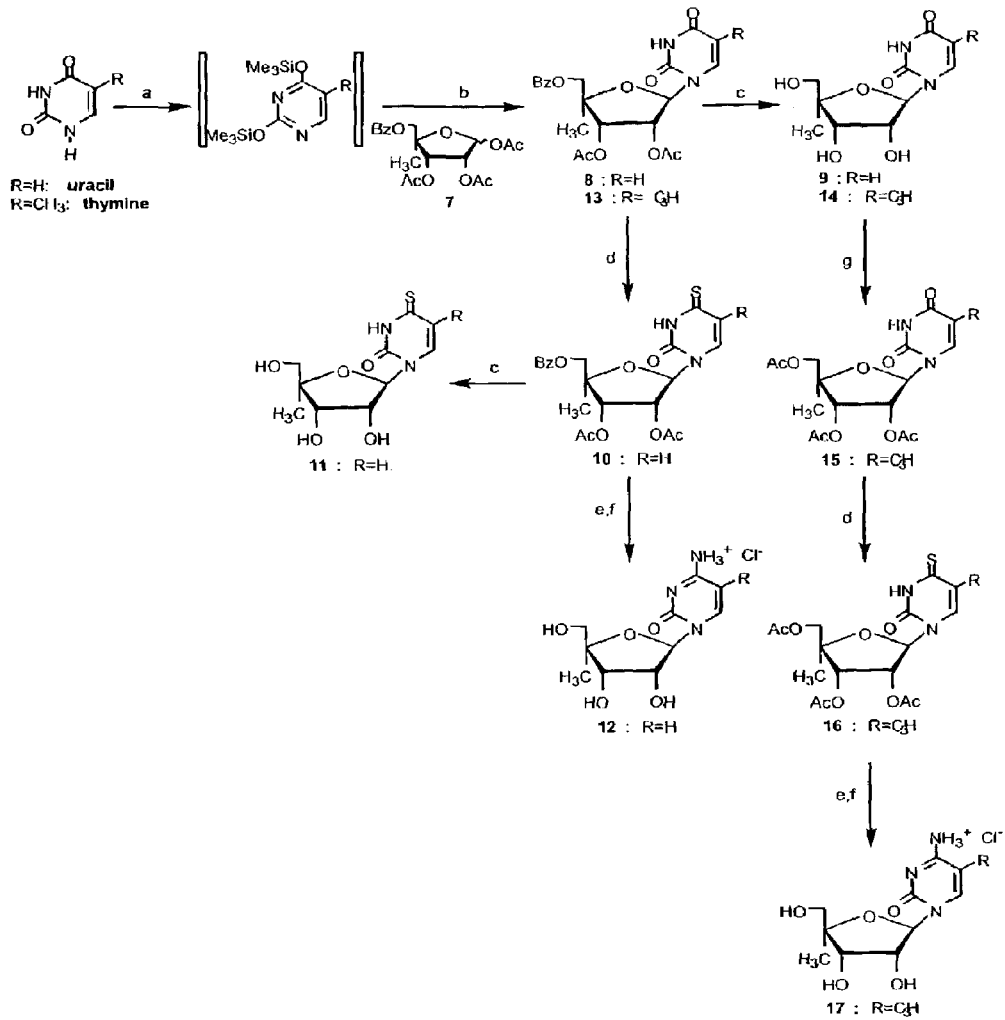
Reagents and conditions: (a) HMDS, (NH$_4$)$_2$SO$_4$, reflux; (b) TMSTf, (CH$_2$Cl)$_2$, r.t.; (c) MeOH/NH$_3$, r.t.(d) Lawesson's reagent, (CH$_2$Cl)$_2$, reflux; (e) MeOH-NH$_3$, 100°C; (f) EtOH/HCl (2N); (g) Ac$_2$O, pyridine, r.t.

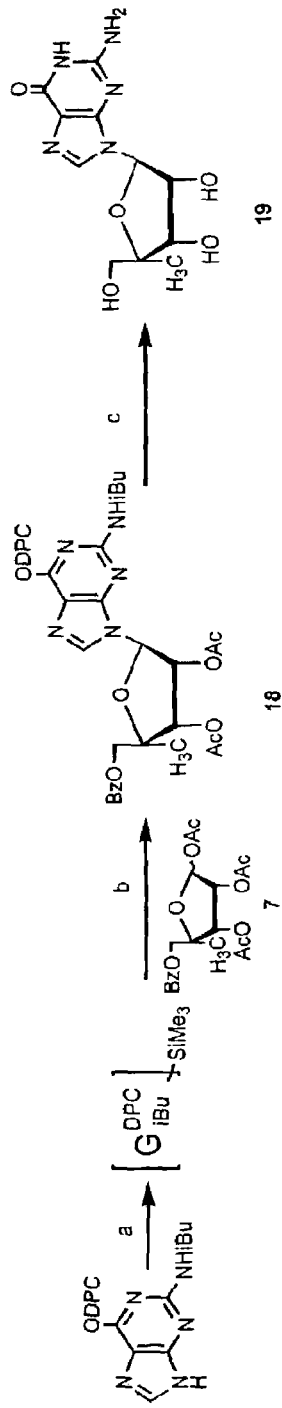
FIGURE 4/5: SYNTHESIS OF COMPOUND 19
Reagents and conditions: (a) BSA, toluene, reflux; (b) TMSTf, reflux; (c) MeOH/NH₃.
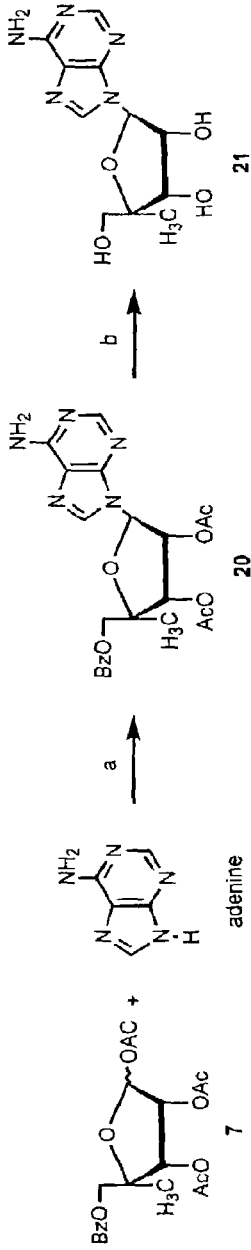
FIGURE 5/5: SYNTHESIS OF COMPOUND 21
Reagents and conditions: (a) SnCl₄, acetonitrile, r.t.; (b) MeOH/NH₃.

METHODS AND COMPOSITIONS FOR TREATING HEPATITIS C VIRUS USING 4'-MODIFIED NUCLEOSIDES

FIELD OF THE INVENTION

This invention is in the area of pharmaceutical chemistry, and is in particular, is a compound, method and composition for the treatment of hepatitis C virus and other viruses that replicate through an RNA-dependent RNA viral polymerase. This application claims priority to U.S. patent application No. 60/326,184 filed Sep. 28, 2001.

BACKGROUND OF THE INVENTION

The hepatitis C virus (HCV) is the leading cause of chronic liver disease worldwide. (Boyer, N. et al. *J. Hepatol.* 32:98–112, 2000). HCV causes a slow growing viral infection and is the major cause of cirrhosis and hepatocellular carcinoma (Di Besceglie, A. M. and Bacon, B. R., *Scientific American*, October: 80–85, (1999); Boyer, N. et al. *J. Hepatol.* 32:98–112, 2000). An estimated 170 million persons are infected with HCV worldwide. (Boyer, N. et al. *J. Hepatol.* 32:98–112, 2000). Cirrhosis caused by chronic hepatitis C infection accounts for 8,000–12,000 deaths per year in the United States, and HCV infection is the leading indication of liver transplantation.

HCV is known to cause at least 80% of posttransfusion hepatitis and a substantial proportion of sporadic acute hepatitis. Preliminary evidence also implicates HCV in many cases of "idiopathic" chronic hepatitis, "cryptogenic" cirrhosis, and probably hepatocellular carcinoma unrelated to other hepatitis viruses, such as hepatitis B virus (HBV). A small proportion of healthy persons appear to be chronic HCV carriers, varying with geography and other epidemiological factors. The numbers may substantially exceed those for HBV, though information is still preliminary; how many of these persons have subclinical chronic liver disease is unclear. (The Merck Manual, ch. 69, p. 901, 16th ed., (1992)).

HCV has been classified as a member of the virus family Flaviviridae that includes the genera flaviviruses, pestiviruses, and hepaciviruses which includes hepatitis C virus (Rice, C. M., Flaviviridae: The viruses and their replication. In: Fields Virology, Editors: Fields, B. N., Knipe, D. M., and Howley, P. M., Lippincott-Raven Publishers, Philadelphia, Pa., Chapter 30, 931–959, 1996). HCV is an enveloped virus containing a positive-sense single-stranded RNA genome of approximately 9.4 kb. The viral genome consists of a 5' untranslated region (UTR), a long open reading frame encoding a polyprotein precursor of approximately 3011 amino acids, and a short 3' UTR. The 5' UTR is the most highly conserved part of the HCV genome and is important for the initiation and control of polyprotein translation. Translation of the HCV genome is initiated by a cap-independent mechanism known as internal ribosome entry. This mechanism involves the binding of ribosomes to an RNA sequence known as the internal ribosome entry site (IRES). An RNA pseudoknot structure has recently been determined to be an essential structural element of the UCV IRES. Viral structural proteins include a nucleocapsid core protein (C) and two envelope glycoproteins, E1 and E2. HCV also encodes two proteinases, a zinc-dependent metalloproteinase encoded by the NS2–NS3 region and a serine proteinase encoded in the NS3 region. These proteinases are required for cleavage of specific regions of the precursor polyprotein into mature peptides. The carboxyl half of nonstructural protein 5, NS5B, contains the RNA-dependent RNA polymerase. The function of the remaining nonstructural proteins, NS4A and NS4B, and that of NS5A (the amino-terminal half of nonstructural protein 5) remain unknown.

A significant focus of current antiviral research is directed toward the development of improved methods of treatment of chronic HCV infections in humans (Di Besceglie, A. M. and Bacon, B. R., *Scientific American*, October: 80–85, (1999)). Currently, there are two primary antiviral compounds, ribavirin and interferon-alpha, which are used for the treatment of chronic HCV infections in humans.

Treatment of HCV Infection with Ribavarin and Interferon

Ribavirin (1-β-D-ribofuranosyl-1-1,2,4-triazole-3-carboxamide) is a synthetic, non-interferon-inducing, broad spectrum antiviral nucleoside analog sold under the trade name, Virazole™ (The Merck Index, 11th edition, Editor: Budavari, S., Merck & Co., Inc., Rahway, N.J., p1304, 1989). U.S. Pat. No. 3,798,209 and RE29,835 disclose and claim ribavirin. Ribavirin is structurally similar to guanosine, and has in vitro activity against several DNA and RNA viruses including Flaviviridae (Gary L. Davis. *Gastroenterology* 118:S104–S114, 2000).

Ribavirin reduces serum amino transferase levels to normal in 40% or patients, but it does not lower serum levels of HCV-RNA (Gary L. Davis. *Gastroenterology* 118:S104–S114, 2000). Thus, ribavirin alone is not effective in reducing viral RNA levels. Additionally, ribavirin has significant toxicity and is known to induce anemia.

Interferons (IFNs) are compounds that have been commercially available for the treatment of chronic hepatitis for nearly a decade. IFNs are glycoproteins produced by immune cells in response to viral infection. IFNs inhibit viral replication of many viruses, including HCV, and when used as the sole treatment for hepatitis C infection, IFN suppresses serum HCV-RNA to undetectable levels. Additionally, IFN normalizes serum amino transferase levels. Unfortunately, the effects of IFN are temporary and a sustained response occurs in only 8%–9% of patients chronically infected with HCV (Gary L. Davis. *Gastroenterology* 118:S104–S114, 2000).

A number of patents disclose HCV treatments using interferon-based therapies. For example, U.S. Pat. No. 5,980,884 to Blatt et al. discloses methods for retreatment of patients afflicted with HCV using consensus interferon. U.S. Pat. No. 5,942,223 to Bazer et al. discloses an anti-HCV therapy using ovine or bovine interferon-tau. U.S. Pat. No. 5,928,636 to Alber et al. discloses the combination therapy of interleukin-12 and interferon alpha for the treatment of infectious diseases including HCV. U.S. Pat. No. 5,908,621 to Glue et al. discloses the use of polyethylene glycol modified interferon for the treatment of HCV. U.S. Pat. No. 5,849,696 to Chretien et al. discloses the use of thymosins, alone or in combination with interferon, for treating HCV. U.S. Pat. No. 5,830,455 to Valtuena et al. discloses a combination HCV therapy employing interferon and a free radical scavenger. U.S. Pat. No. 5,738,845 to Imakawa discloses the use of human interferon tau proteins for treating HCV. Other interferon-based treatments for HCV are disclosed in U.S. Pat. No. 5,676,942 to Testa et al., U.S. Pat. No. 5,372,808 to Blatt et al., and U.S. Pat. No. 5,849,696.

Combination of Interferon and Ribavirin

Schering-Plough sells ribavirin as Rebetol® capsules (200 mg) for administration to patients with HCV. The U.S. FDA has approved Rebetol capsules to treat chronic HCV infection in combination with Schering's alpha interferon products Intron® A and PEG-Intron™. Rebetol capsules are not approved for monotherapy (i.e., administration independent of Intron A or PEG-Intron), although Intron A and PEG-Intron are approved for monotherapy (i.e., administration without ribavirin). Hoffman La Roche is selling ribavirin under the name CoPegus, also for use in combination with interferon for the treatment of HCV. Other alpha interferon products are Roferon-A (Hoffmann-La Roche), Infergen® (Intermune, formerly Amgen's product), and Wellferon® (Wellcome Foundation) are currently FDA-approved for HCV monotherapy.

Additional References Disclosing Methods to Treat HCV Infections

A number of HCV treatments are reviewed by Bymock et al. in *Antiviral Chemistry & Chemotherapy*, 11:2; 79–95 (2000).

Several substrate-based NS3 protease inhibitors have been identified in the literature, in which the scissile amide bond of a cleaved substrate is replaced by an electrophile, which interacts with the catalytic serine. Attwood et al. (1998) Antiviral peptide derivatives, 98/22496; Attwood et al. (1999), *Antiviral Chemistry and Chemotherapy* 10.259–273; Attwood et al. (1999) Preparation and use of amino acid derivatives as anti-viral agents, German Patent Publication DE 19914474; Tung et al. (1998) Inhibitors of serine proteases, particularly hepatitis C virus NS3 protease, WO 98/17679. The reported inhibitors terminate in an electrophile such as a boronic acid or phosphonate. Llinas-Brunet et al. (1999) Hepatitis C inhibitor peptide analogues, WO 99/07734. Two classes of electrophile-based inhibitors have been described, alphaketoamides and hydrazinoureas.

The literature has also described a number of non-substrate-based inhibitors. For example, evaluation of the inhibitory effects of 2,4,6-trihydroxy-3-nitro-benzamide derivatives against HCV protease and other serine proteases has been reported. Sudo, K. et al., (1997) *Biochemical and Biophysical Research Communications*, 238:643–647; Sudo, K. et al. (1998) *Antiviral Chemistry and Chemotherapy* 9:186. Using a reverse-phase HPLC assay, the two most potent compounds identified were RD3–4082 and RD3–4078, the former substituted on the amide with a 14 carbon chain and the latter processing a para-phenoxyphenyl group.

Thiazolidine derivatives have been identified as micromolar inhibitors, using a reverse-phase HPLC assay with an NS3/4A fusion protein and NS5A/5B substrate. Sudo, K. et al. (1996) *Antiviral Research* 32:9–18. Compound RD-1–6250, possessing a fused cinnamoyl moiety substituted with a long alkyl chain, was the most potent against the isolated enzyme. Two other active examples were RD4 6205 and RD4 6193.

Other literature reports screening of a relatively small library using an ELISA assay and the identification of three compounds as potent inhibitors, a thiazolidine and two benzanilides. Kakiuchi N. et al. *J. EBS Letters* 421:217–220; Takeshita N. et al., *Analytical Biochemistry* 247:242–246, 1997. Several U.S. patents disclose protease inhibitors for the treatment of HCV. For example, U.S. Pat. No. 6,004,933 to Spruce et al. discloses a class of cysteine protease inhibitors for inhibiting HCV endopeptidase 2. U.S. Pat. No. 5,990,276 to Zhang et al. discloses synthetic inhibitors of hepatitis C virus NS3 protease. The inhibitor is a subsequence of a substrate of the NS3 protease or a substrate of the NS4A cofactor. The use of restriction enzymes to treat HCV is disclosed in U.S. Pat. No. 5,538,865 to Reyes et al.

Isolated from the fermentation culture broth of *Streptomyces* sp., Sch 68631, a phenan-threnequinone, possessed micromolar activity against HCV protease in a SDS-PAGE and autoradiography assay. Chu M. et al., *Tetrahedron Letters* 37:7229–7232, 1996. In another example by the same authors, Sch 351633, isolated from the fungus *Penicillium griscofuluum*, demonstrated micromolar activity in a scintillation proximity assay. Chu M. et al., *Bioorganic and Medicinal Chemistry Letters* 9:1949–1952. Nanomolar potency against the HCV NS3 protease enzyme has been achieved by the design of selective inhibitors based on the macromolecule eglin c. Eglin c, isolated from leech, is a potent inhibitor of several serine proteases such as *S. griseus* proteases A and B, α-chymotrypsin, chymase and subtilisin. Qasim M. A. et al., *Biochemistry* 36:1598–1607, 1997.

HCV helicase inhibitors have also been reported. U.S. Pat. No. 5,633,358 to Diana G. D. et al.; PCT Publication No. WO 97/36554 of Diana G. D. et al. There are a few reports of HCV polymerase inhibitors: some nucleotide analogues, gliotoxin and the natural product cerulenin. Ferrari R. et al., *Journal of Virology* 73:1649–1654, 1999; Lohmann V. et al., *Virology* 249:108–118, 1998.

Antisense phosphorothioate oligodeoxynucleotides complementary to sequence stretches in the 5' non-coding region of the HCV, are reported as efficient inhibitors of HCV gene expression in in vitro translation and IIcpG2 IICV-luciferase cell culture systems. Alt M. et al., *Hepatology* 22:707–717, 1995. Recent work has demonstrated that nucleotides 326–348 comprising the 3' end of the NCR and nucleotides 371–388 located in the core coding region of the HCV RNA are effective targets for antisense-mediated inhibition of viral translation. Alt M. et al., *Archives of Virology* 142:589–599, 1997. U.S. Pat. No. 6,001,990 to Wands et al. discloses oligonucleotides for inhibiting the replication of HCV. PCT Publication No. WO 99/29350 discloses compositions and methods of treatment for hepatitis C infection comprising the administration of antisense oligonucleotides that are complementary and hybridizable to HCV-RNA. U.S. Pat. No. 5,922,857 to Han et al. disclose nucleic acids corresponding to the sequence of the pestivirus homology box IV area for controlling the translation of HCV. Antisense oligonucleotides as therapeutic agents have been recently reviewed (Galderisi U. et al., *Journal of Cellular Physiology* 181:251–257, 1999).

Other compounds have been reported as inhibitors of IRES-dependent translation in HCV. Japanese Patent Publication JP-08268890 of Ikeda N et al.; Japanese Patent Publication JP-10101591 of Kai, Y. et al. Nuclease-resistant ribozymes have been targeted at the IRES and recently reported as inhibitors in an HCV-poliovirus chimera plaque assay. Maccjak D. J. et al., *Hepatology* 30 abstract 995, 1999. The use of ribozymes to treat HCV is also disclosed in U.S. Pat. No. 6,043,077 to Barber et al., and U.S. Pat. Nos. 5,869,253 and 5,610,054 to Draper et al.

Other patents disclose the use of immune system potentiating compounds for the treatment of HCV. For example, U.S. Pat. No. 6,001,799 to Chretien et al. discloses a method of treating hepatitis C in non-responders to interferon treatment by administering an immune system potentiating dose of thymosin or a thymosin fragment. U.S. Pat. Nos. 5,972, 347 to Eder et al. and 5,969,109 to Bona et al. disclose antibody-based treatments for treating HCV.

U.S. Pat. No. 6,034,134 to Gold et al. discloses certain NMDA receptor agonists having immunodulatory, antimalarial, anti-Borna virus and anti-Hepatitis C activities. The disclosed NMDA receptor agonists belong to a family of 1-amino-alkylcyclohexanes. U.S. Pat. No. 6,030,960 to Morris-Natschke et al. discloses the use of certain alkyl lipids to inhibit the production of hepatitis-induced antigens, including those produced by the HCV virus. U.S. Pat. No. 5,922,757 to Chojkier et al. discloses the use of vitamin E and other antioxidants to treat hepatic disorders including HCV. U.S. Pat. No. 5,858,389 to Elsherbi et al. discloses the use of squalene for treating hepatitis C. U.S. Pat. No. 5,849,800 to Smith et al discloses the use of amantadine for treatment of Hepatitis C. U.S. Pat. No. 5,846,964 to Ozeki et al. discloses the use of bile acids for treating HCV. U.S. Pat. No. 5,491,135 to Blough et al. discloses the use of N-(phosphonoacetyl)-L-aspartic acid to treat flaviviruses such as HCV.

Other compounds proposed for treating HCV include plant extracts (U.S. Pat. No. 5,837,257 to Tsai et al., U.S. Pat. No. 5,725,859 to Omer et al., and U.S. Pat. No. 6,056,961), piperidenes (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxyinosine (U.S. Pat. No. 5,026,687 to Yarchoan et al.), benzimidazoles (U.S. Pat. No. 5,891,874 to Colacino et al.).

Other agents developed for the treatment of HCV includes PEGASYS (pegylated interferon alfa-2a) by Roche, INFERGEN (interferon alfacon-1) by InterMune, OMNIFERON (natural interferon) by Viragen, ALBUFERON by Human Genome Sciences, REBIF (interferon beta-1a) by Ares-Serono, Omega Interferon by BioMedicine, Oral Interferon Alpha by Amarillo Biosciences, Interferon gamma-1b by InterMune, Interleukin-10 by Schering-Plough, IP-501 by Interneuron, Merimebodib VX-497 by Vertex, AMANTADINE (Symmetrel) by Endo Labs Solvay, HEPTAZYME by RPI, IDN-6556 by Idun Pharma., XTL-002 by XTL., HCV/MF59 by Chiron, CIVACIR by NABI, LEVOVIRIN by ICN, VIRAMIDINE by ICN, ZADAXIN (thymosin alfa-1) by Sci Clone, CEPLENE (histamine dihydrochloride) by Maxim, VX 950/LY 570310 by Vertex/Eli Lilly, ISIS 14803 by Isis Pharmaceutical/Elan, IDN-6556 by Idun Pharmaceuticals, Inc. and JTK 003 by AKROS Pharma.

Idenix Pharmaceuticals, Ltd. was first to disclose branched nucleosides, and their use in the treatment of HCV and flaviviruses and pestiviruses in International Publication Nos. WO 01/90121 and WO 01/92282.

A method for the treatment of hepatitis C infection (and flaviviruses and pestiviruses) in humans and other host animals is disclosed in the Idenix publications that includes administering an effective amount of a biologically active 1', 2', or 3'-branched β-D or β-L nucleosides or a pharmaceutically acceptable salt or prodrug thereof, administered either alone or in combination, optionally in a pharmaceutically acceptable carrier.

WO 01/96353 to Indenix Pharmaceuticals, Ltd. discloses 3'-prodrugs of 2'-deoxy-β-L-nucleosides for the treatment of HBV. U.S. Pat. No. 4,957,924 to Beauchamp discloses various therapeutic esters of acyclovir.

Other patent applications disclosing the use of certain nucleoside analogs to treat hepatitis C virus include: PCT/CA00/01316 (WO 01/32153) and PCTCA01/00197 (WO 01/60315) filed by BioChem Pharma, Inc. (now Shire Biochem, Inc.); PCT/US02/01531 (WO 02/057425 A2) and PCT/US02/03086 (WO 02/057287) filed by Merck & Co., Inc., and PCTEP01/09633 (WO 02/18404) filed by Hoffman La Roche.

In light of the fact that the hepatitis C virus has reached epidemic levels worldwide, and has tragic effects on the infected patient, there remains a strong need to provide new effective pharmaceutical agents to treat hepatitis C that has low toxicity to the host.

Therefore, it is an object of the present invention to provide a compound, method and composition for the treatment of a host infected with hepatitis C virus.

SUMMARY OF THE INVENTION

Compounds, methods and compositions for the treatment of hepatitis C infection are described that include an effective hepatitis C treatment amount of a β-D- or β-L-nucleoside of the Formulas (I)–(VI), or a pharmaceutically acceptable salt or prodrug thereof. These compounds can also be used generally as inhibitors of RNA-dependent RNA viral polymerase.

In a first principal embodiment, a compound of Formula I, or a pharmaceutically acceptable salt or prodrug thereof, is provided:

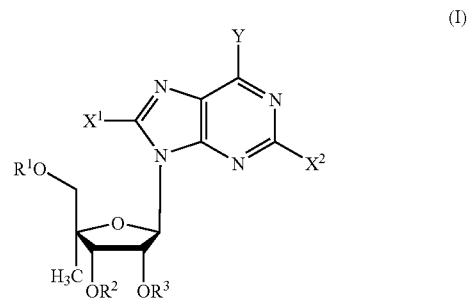

(I)

wherein:

$R^1$, $R^2$ and $R^3$ are independently H, phosphate (including mono-, di- or triphosphate and a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

Y is hydrogen, bromo, chloro, fluoro, iodo, $OR^4$, $NR^4R^5$ or $SR^4$;

$X^1$ and $X^2$ are independently selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a second principal embodiment, a compound of Formula II, or a pharmaceutically acceptable salt or prodrug thereof, is provided:

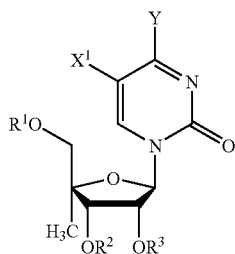

(II)

wherein:
$R^1$, $R^2$ and $R^3$ are independently H, phosphate (including mono-, di- or triphosphate and a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

Y is hydrogen, bromo, chloro, fluoro, iodo, $OR^4$, $NR^4R^5$ or $SR^4$;

$X^1$ is selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a third principal embodiment, a compound selected from Formulas III, IV and V, or a pharmaceutically acceptable salt or prodrug thereof, is provided:

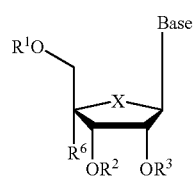

(III)

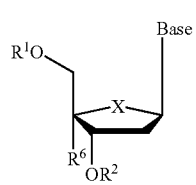

(IV)

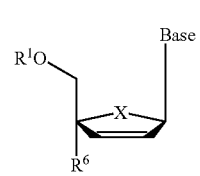

(V)

wherein:
Base is a purine or pyrimidine base as defined herein;
$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

$R^6$ is hydroxy, alkyl (including lower alkyl), azido, cyano, alkenyl, alkynyl, Br-vinyl, 2-Br-ethyl, —C(O)O(alkyl), —C(O)O(lower alkyl), —O(acyl), —O(lower acyl), —O(alkyl), —O(lower alkyl), —O(alkenyl), $CF_3$, chloro, bromo, fluoro, iodo, $NO_2$, $NH_2$, —NH(lower alkyl), —NH(acyl), —N(lower alkyl)$_2$, —N(acyl)$_2$; and X is O, S, $SO_2$ or $CH_2$.

In a fourth principal embodiment the invention provides a compound of Formula VI, or a pharmaceutically acceptable salt or prodrug thereof:

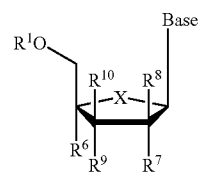

(VI)

wherein:
Base is a purine or pyrimidine base as defined herein;
$R^1$ and $R^2$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ or $R^2$ is independently H or phosphate;

$R^6$ is hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;

$R^7$ and $R^9$ are independently hydrogen, $OR^2$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$;

$R^8$ and $R^{10}$ are independently H, alkyl (including lower alkyl), chlorine, bromine or iodine;

alternatively, $R^7$ and $R^9$, $R^7$ and $R^{10}$, $R^8$ and $R^9$, or $R^8$ and $R^{10}$ can come together to form a pi bond; and X is O, S, SO$_2$ or CH$_2$.

The β-D- and β-L-nucleosides of this invention may inhibit HCV polymerase activity, and can be generally used as inhibitors of RNA-dependent RNA viral polymerase. Nucleosides can be screened for their ability to inhibit HCV polymerase activity in vitro according to screening methods set forth more particularly herein. One can readily determine the spectrum of activity by evaluating the compound in the assays described herein or with another confirmatory assay.

In one embodiment the efficacy of the anti-HCV compound is measured according to the concentration of compound necessary to reduce the plaque number of the virus in vitro, according to methods set forth more particularly herein, by 50% (i.e. the compound's EC$_{50}$). In preferred embodiments the compound exhibits an EC$_{50}$ of less than 25, 15, 10, 5, or 1 micromolar.

In another embodiment, the active compound can be administered in combination or alternation with another anti-HCV agent or anti-RNA-dependent RNA polymerase agent. In combination therapy, an effective dosage of two or more agents are administered together, whereas during alternation therapy an effective dosage of each agent is administered serially. The dosages will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens and schedules should be adjusted over time according to the individual need and the professional judgment of the person administering or supervising the administration of the compositions.

BRIEF DESCRIPTION OF THE FIGURES

FIG. 1 provides the structure of various non-limiting examples of nucleosides of the present invention, as well as other known nucleosides, FIAU and Ribavirin, which are used as comparative examples in the text.

FIG. 2 is a non-limiting illustration of the synthesis of a pentodialdo-furanose of the present invention, 1-O-methyl-2,3-O-isopropylidene β-D-ribo-pentodialdo-furanose (2) and a 4'-modified sugar of the present invention, 5-O-benzoyl-4-C-methyl-1,2,3-O-acetyl-α,β-D-ribofuranose (7).

FIG. 3 is a non-limiting illustration of the synthesis of various 4'-modified pyrimidine nucleoside of the present invention, including 1-(4-C-methyl-β-D-ribofuranosyl)-uracil (9), 1-(4-C-methyl-β-D-ribofuranosyl)4-thio-uracil (11) and 1-(4-C-methyl-β-D-ribo-furanosyl)thymine (14); and pharmaceutically acceptable salts, including 1-(4-C-methyl-β-D-ribofuranosyl)cytosine, hydrochloric form (12) and 1-(4-C-methyl-β-D-ribofuranosyl)-5-methyl-cytosine, hydrochloride form (17).

FIG. 4 is a non-limiting illustration of the synthesis of a 4'-modified purine nucleoside of the present invention, 9-(4-C-methyl-β-D-ribofuranosyl) guanine (19).

FIG. 5 is a non-limiting illustration of the synthesis of a 4'-modified purine nucleoside of the present invention, 9-(4-C-methyl-β-D-ribofuranosyl) adenine (21).

DETAILED DESCRIPTION OF THE INVENTION

The invention as disclosed herein is a compound, method and composition for the treatment of hepatitis C in humans or other host animals, that includes administering an effective HCV treatment amount of a β-D- or β-L-nucleoside as described herein or a pharmaceutically acceptable salt or prodrug thereof, optionally in a pharmaceutically acceptable carrier. The compounds of this invention either possess antiviral (i.e., anti-HCV) activity, or are metabolized to a compound that exhibits such activity. In an alternative embodiment, the compounds can be used generally to inhibit RNA-dependent RNA viral polymerase.

In summary, the present invention includes the following features:

(a) β-D- and β-L-nucleosides, as described herein, and pharmaceutically acceptable salts and prodrugs thereof;

(b) β-D- and β-L-nucleosides as described herein, and pharmaceutically acceptable salts and prodrugs thereof for use in the treatment or prophylaxis of an HCV infection, especially in individuals diagnosed as having an HCV infection or being at risk for becoming infected by HCV;

(c) use of these β-D- and β-L-nucleosides, and pharmaceutically acceptable salts and prodrugs thereof in the manufacture of a medicament for treatment of an HCV infection;

(d) pharmaceutical formulations comprising the β-D- or β-L-nucleosides or pharmaceutically acceptable salts or prodrugs thereof together with a pharmaceutically acceptable carrier or diluent;

(e) β-D- and β-L-nucleosides as described herein substantially in the absence of enantiomers of the described nucleoside, or substantially isolated from other chemical entities;

(f) processes for the preparation of β-D- and β-L-nucleosides, as described in more detail below; and (g) processes for the preparation of β-D- and β-L-nucleosides substantially in the absence of enantiomers of the described nucleoside, or substantially isolated from other chemical entities.

I. Active Compound, and Physiologically Acceptable Salts and Prodrugs Thereof

In a first principal embodiment, a compound of Formula I, or a pharmaceutically acceptable salt or prodrug thereof, is provided:

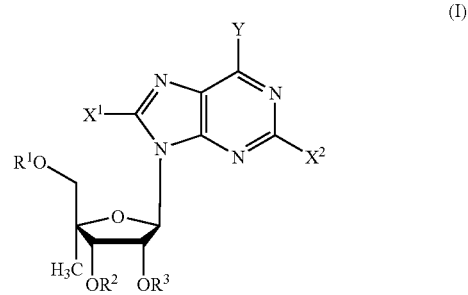

(I)

wherein:

$R^1$, $R^2$ and $R^3$ are independently H, phosphate (including mono-, di- or triphosphate and a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

Y is hydrogen, bromo, chloro, fluoro, iodo, $OR^4$, $NR^4R^5$ or $SR^4$;

$X^1$ and $X^2$ are independently selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a preferred subembodiment, a compound of Formula I, or a pharmaceutically acceptable salt or prodrug thereof, is provided wherein:

$R^1$, $R^2$ and $R^3$ are independently H or phosphate (preferably H);

$X^1$ is H;

$X^2$ is H or $NH_2$; and

Y is hydrogen, bromo, chloro, fluoro, iodo, $NH_2$ or OH.

In a second principal embodiment, a compound of Formula II, or a pharmaceutically acceptable salt or prodrug thereof, is provided:

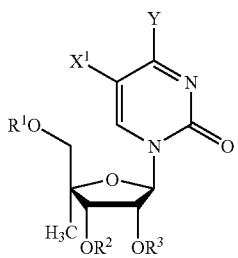

(II)

wherein:

$R^1$, $R^2$ and $R^3$ are independently H, phosphate (including mono-, di- or triphosphate and a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

Y is hydrogen, bromo, chloro, fluoro, iodo, $OR^4$, $NR^4R^5$ or $SR^4$;

$X^1$ is selected from the group consisting of H, straight chained, branched or cyclic alkyl, CO-alkyl, CO-aryl, CO-alkoxyalkyl, chloro, bromo, fluoro, iodo, $OR^4$, $NR^4NR^5$ or $SR^5$; and $R^4$ and $R^5$ are independently hydrogen, acyl (including lower acyl), or alkyl (including but not limited to methyl, ethyl, propyl and cyclopropyl).

In a preferred subembodiment, a compound of Formula II, or a pharmaceutically acceptable salt or prodrug thereof, is provided wherein:

$R^1$, $R^2$ and $R^3$ are independently H or phosphate (preferably H);

$X^1$ is H or $CH_3$; and

Y is hydrogen, bromo, chloro, fluoro, iodo, $NH_2$ or OH.

In a third principal embodiment, a compound selected from Formulas III, IV and V, or a pharmaceutically acceptable salt or prodrug thereof, is provided:

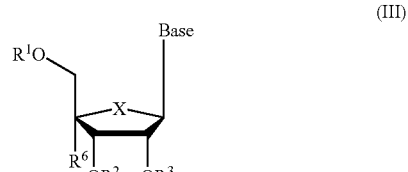

(III)

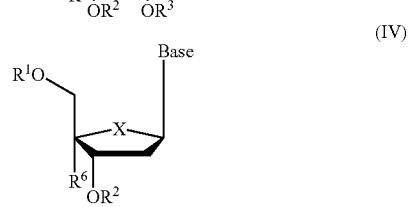

(IV)

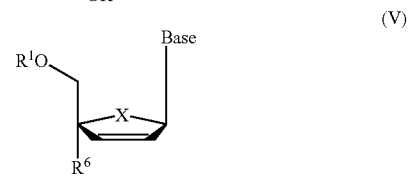

(V)

wherein:

Base is a purine or pyrimidine base as defined herein;

$R^1$, $R^2$ and $R^3$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$, $R^2$ or $R^3$ is independently H or phosphate;

$R^6$ is hydroxy, alkyl (including lower alkyl), azido, cyano, alkenyl, alkynyl, Br-vinyl, 2-Br-ethyl, —C(O)O(alkyl), —C(O)O(lower alkyl), —O(acyl), —O(lower acyl), —O(alkyl), —O(lower alkyl), —O(alkenyl), $CF_3$, chloro, bromo, fluoro, iodo, $NO_2$, $NH_2$, —NH(lower alkyl), —NH(acyl), —N(lower alkyl)$_2$, —N(acyl)$_2$; and X is O, S, $SO_2$ or $CH_2$.

In a first preferred subembodiment, a compound of Formula III, IV or V, or a pharmaceutically acceptable salt or prodrug thereof, is provided wherein:

Base is a purine or pyrimidine base as defined herein;

$R^1$, $R^2$ and $R^3$ are independently hydrogen or phosphate;

$R^6$ is alkyl; and

X is O, S, $SO_2$ or $CH_2$.

In a second preferred subembodiment, a compound of Formula III, IV or V, or a pharmaceutically acceptable salt or prodrug thereof, is provided wherein:

Base is a purine or pyrimidine base as defined herein;

$R^1$, $R^2$ and $R^3$ are hydrogens;

$R^6$ is alkyl; and

X is O, S, $SO_2$ or $CH_2$.

In a third preferred subembodiment, a compound of Formula III, IV or V, or a pharmaceutically acceptable salt or prodrug thereof, is provided wherein:
Base is a purine or pyrimidine base as defined herein;
$R^1$, $R^2$ and $R^3$ are independently hydrogen or phosphate;
$R^6$ is alkyl; and
X is O.

In even more preferred subembodiments, a compound of Formula IV, or its pharmaceutically acceptable salt or prodrug, is provided:

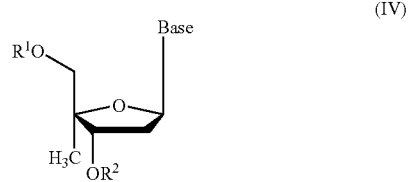

(IV)

wherein:
Base is a purine or pyrimidine base as defined herein; optionally substituted with an amine or cyclopropyl (e.g., 2-amino, 2,6-diamino or cyclopropyl guanosine); and
$R^1$ and $R^2$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ or $R^2$ is independently H or phosphate.

In a fourth principal embodiment the invention provides a compound of Formula VI, or a pharmaceutically acceptable salt or prodrug thereof:

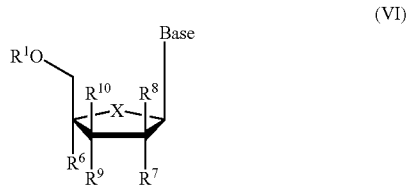

(VI)

wherein:
Base is a purine or pyrimidine base as defined herein;
$R^1$ and $R^2$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ or $R^2$ is independently H or phosphate;

$R^6$ is hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;
$R^7$ and $R^9$ are independently hydrogen, $OR^2$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$;
$R^8$ and $R^{10}$ are independently H, alkyl (including lower alkyl), chlorine, bromine or iodine;
alternatively, $R^7$ and $R^9$, $R^7$ and $R^{10}$, $R^8$ and $R^9$, or $R^8$ and $R^{10}$ can come together to form a pi bond; and
X is O, S, $SO_2$ or $CH_2$.

In a first preferred subembodiment, a compound of Formula VI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl; (4) $R^7$ and $R^9$ are independently $OR^2$, alkyl, alkenyl, alkynyl, Br-vinyl, O-alkenyl, chlorine, bromine, iodine, $NO_2$, amino, loweralkylamino or di(loweralkyl)amino; (5) $R^8$ and $R^{10}$ are independently H, alkyl (including lower alkyl), chlorine, bromine, or iodine; and (6) X is O, S, $SO_2$ or $CH_2$.

In a second preferred subembodiment, a compound of Formula VI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl, alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently $OR^2$; (5) $R^8$ and $R^{10}$ are independently H, alkyl (including lower alkyl), chlorine, bromine, or iodine; and (6) X is O, S, $SO_2$ or $CH_2$.

In a third preferred subembodiment, a compound of Formula VI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl, alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$, alkyl, alkenyl, alkynyl, Br-vinyl, O-alkenyl, chlorine, bromine, iodine, $NO_2$, amino, loweralkylamino or di(loweralkyl)amino; (5) $R^8$ and $R^{10}$ are H; and (6) X is O, S, $SO_2$ or $CH_2$.

In a fourth preferred subembodiment, a compound of Formula VI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl, alkenyl, alkynyl, Br-vinyl, hydroxy, O-alkyl, O-alkenyl, chloro, bromo, fluoro, iodo, $NO_2$, amino, loweralkylamino, or di(loweralkyl)amino; (4) $R^7$ and $R^9$ are independently $OR^2$, alkyl, alkenyl, alkynyl, Br-vinyl, O-alkenyl, chlorine, bromine, iodine, $NO_2$, amino, loweralkylamino, or di(loweralkyl)amino; (5) $R^8$ and $R^{10}$ are independently H, alkyl (including lower alkyl), chlorine, bromine, or iodine; and (6) X is O.

In a fifth preferred subembodiment, a compound of Formula VI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl; (4) $R^7$ and $R^9$ are independently $OR^1$; (5) $R^8$ and $R^{10}$ are independently H, alkyl (including lower alkyl), chlorine, bromine or iodine; and (6) X is O, S, $SO_2$ or $CH_2$.

In a sixth preferred subembodiment, a compound of Formula VI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl; (4) $R^7$ and $R^9$ are independently $OR^2$, alkyl (including lower alkyl), alkenyl, alkynyl, Br-vinyl, O-alkenyl, chlorine, bromine, iodine, $NO_2$, amino, loweralkylamino, or di(loweralkyl)amino; (5) $R^8$ and $R^{10}$ are H; and (6) X is O, S, $SO_2$, or $CH_2$.

In a seventh preferred subembodiment, a compound of Formula VI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl; (4) $R^7$ and $R^9$ are independently $OR^2$, alkyl (including lower alkyl), alkenyl, alkynyl, Br-vinyl, O-alkenyl, chlorine, bromine, iodine, $NO_2$, amino, loweralkylamino or di(loweralkyl)amino; (5) $R^8$ and $R^{10}$ are independently H, alkyl (including lower alkyl), chlorine, bromine or iodine; and (6) X is O.

In a eighth preferred subembodiment, a compound of Formula VI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^8$ and $R^{10}$ are hydrogen; and (6) X is O, S, $SO_2$ or $CH_2$.

In a ninth preferred subembodiment, a compound of Formula VI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^8$ and $R^{10}$ are independently H, alkyl (including lower alkyl), chlorine, bromine or iodine; and (6) X is O.

In a tenth preferred subembodiment, a compound of Formula VI, or its pharmaceutically acceptable salt or prodrug, is provided in which: (1) Base is a purine or pyrimidine base as defined herein; (2) $R^1$ is independently H or phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$, alkyl (including lower alkyl), alkenyl, alkynyl, Br-vinyl, O-alkenyl, chlorine, bromine, iodine, $NO_2$, amino, loweralkylamino, or di(loweralkyl) amino; (5) $R^8$ and $R^{10}$ are hydrogen; and (6) X is O.

In an eleventh preferred subembodiment, a compound of Formula VI, or its pharmaceutically acceptable salt or prodrug, is provided in which: (1) Base is a purine or pyrimidine base as defined herein; (2) $R^1$ is independently H or phosphate; (3) $R^6$ is alkyl (including lower alkyl), alkenyl, alkynyl, Br-vinyl, hydroxy, O-alkyl, O-alkenyl, chloro, bromo, fluoro, iodo, $NO_2$, amino, loweralkylamino or di(loweralkyl)amino; (4) $R^7$ and $R^9$ are independently $OR^2$; (5) $R^8$ and $R^{10}$ are hydrogen; and (6) X is O, S, $SO_2$ or $CH_2$.

In a twelfth preferred subembodiment, a compound of Formula VI, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently $OR^2$; (5) $R^8$ and $R^{10}$ are hydrogen; and (6) X is O, S, $SO_2$, or $CH_2$.

In a thirteenth preferred subembodiment, a compound of Formula VI, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently $OR^2$; (5) $R^1$ and $R^{10}$ are independently H, alkyl (including lower alkyl), chlorine, bromine, or iodine; and (6) X is O.

In a fourteenth preferred subembodiment, a compound of Formula VI, or its pharmaceutically acceptable salt or prodrug, is provided in which: (1) Base is a purine or pyrimidine base as defined herein; (2) $R^1$ is independently H or phosphate; (3) $R^6$ is alkyl; (4) $R^7$ and $R^9$ are independently $OR^2$, alkyl (including lower alkyl), alkenyl, alkynyl, Br-vinyl, O-alkenyl, chlorine, bromine, iodine, $NO_2$, amino, loweralkylamino or di(loweralkyl)amino; (5) $R^8$ and $R^{10}$ are hydrogen; and (6) X is O.

In even more preferred subembodiments, a compound of Formula VI, or its pharmaceutically acceptable salt or prodrug, is provided in which:

(1) Base is adenine; (2) $R^1$ is hydrogen; (3) $R^6$ is methyl; (4) $R^7$ and $R^9$ are hydroxyl; (5) $R^8$ and $R^{10}$ are hydrogen; and (6) X is O;

(1) Base is guanine; (2) $R^1$ is hydrogen; (3) $R^6$ is methyl; (4) $R^7$ and $R^9$ are hydroxyl; (5) $R^8$ and $R^{10}$ are hydrogen; and (6) X is O;

(1) Base is cytosine; (2) $R^1$ is hydrogen; (3) $R^6$ is methyl; (4) $R^7$ and $R^9$ are hydroxyl; (5) $R^8$ and $R^{10}$ are hydrogen; and (6) X is O;

(1) Base is thymine; (2) $R^1$ is hydrogen; (3) $R^6$ is methyl; (4) $R^7$ and $R^9$ are hydroxyl; (5) $R^8$ and $R^{10}$ are hydrogen; and (6) X is O;

(1) Base is uracil; (2) $R^1$ is hydrogen; (3) $R^6$ is methyl; (4) $R^7$ and $R^9$ are hydroxyl; (5) $R^8$ and $R^{10}$ are hydrogen; and (6) X is O;

(1) Base is adenine; (2) $R^1$ is phosphate; (3) $R^6$ is methyl; (4) $R^7$ and $R^9$ are hydroxyl; (5) $R^8$ and $R^{10}$ are hydrogen; and (6) X is O;

(1) Base is adenine; (2) $R^1$ is hydrogen; (3) $R^6$ is ethyl; (4) $R^7$ and $R^9$ are hydroxyl; (5) $R^8$ and $R^{10}$ are hydrogen; and (6) X is O;

(1) Base is adenine; (2) $R^1$ is hydrogen; (3) $R^6$ is propyl; (4) $R^7$ and $R^9$ are hydroxyl; (5) $R^8$ and $R^{10}$ are hydrogen; and (6) X is O;

(1) Base is adenine; (2) $R^1$ is hydrogen; (3) $R^6$ is butyl; (4) $R^7$ and $R^9$ are hydroxyl; (5) $R^8$ and $R^{10}$ are hydrogen; and (6) X is O;

(1) Base is adenine; (2) $R^1$ is hydrogen; (3) $R^6$ is methyl; (4) $R^7$ is hydrogen and $R^9$ is hydroxyl; (5) $R^8$ and $R^{10}$ are hydrogen; and (6) X is O;

(1) Base is adenine; (2) $R^1$ is hydrogen; (3) $R^6$ is methyl; (4) $R^7$ and $R^9$ are hydroxyl; (5) $R^8$ and $R^{10}$ are hydrogen; and (6) X is S;

(1) Base is adenine; (2) $R^1$ is hydrogen; (3) $R^6$ is methyl; (4) $R^7$ and $R^9$ are hydroxyl; (5) $R^8$ and $R^{10}$ are hydrogen; and (6) X is $SO_2$; or (1) Base is adenine; (2) $R^1$ is hydrogen; (3) $R^6$ is methyl; (4) $R^7$ and $R^9$ are hydroxyl; (5) $R^8$ and $R^{10}$ are hydrogen; and (6) X is $CH_2$.

The β-D- and β-L-nucleosides of this invention may inhibit HCV polymerase activity. Nucleosides can be screened for their ability to inhibit HCV polymerase activity in vitro according to screening methods set forth more particularly herein. One can readily determine the spectrum of activity by evaluating the compound in the assays described herein or with another confirmatory assay.

In one embodiment the efficacy of the anti-HCV compound is measured according to the concentration of compound necessary to reduce the plaque number of the virus in vitro, according to methods set forth more particularly herein, by 50% (i.e. the compound's $EC_{50}$). In preferred embodiments the compound exhibits an $EC_{50}$ of less than 15 or 10 micromolar, when measured according to the polymerase assay described in Ferrari et al., *Jnl. of Vir.*, 73:1649–1654, 1999; Ishii et al., *Hepatology*, 29:1227–1235,1999; Lohmann et al., *Jnl. of Bio. Chem.*, 274:10807–10815, 1999; or Yamashita et al, *Jnl. of Bio. Chem.*, 273:15479–15486, 1998.

The active compound can be administered as any salt or prodrug that upon administration to the recipient is capable of providing directly or indirectly the parent compound, or that exhibits activity itself. Nonlimiting examples are the pharmaceutically acceptable salts (alternatively referred to as "physiologically acceptable salts"), and a compound that has been alkylated or acylated at the 5'-position or on the purine or pyrimidine base (a type of "pharmaceutically acceptable prodrug"). Further, the modifications can affect the biological activity of the compound, in some cases increasing the activity over the parent compound. This can easily be assessed by preparing the salt or prodrug and testing its antiviral activity according to the methods described herein, or other methods known to those skilled in the art.

II. Definitions

The term alkyl, as used herein, unless otherwise specified, refers to a saturated straight, branched, or cyclic, primary, secondary, or tertiary hydrocarbon of typically $C_1$ to $C_{10}$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The term includes both substituted and unsubstituted alkyl groups. Moieties with which the alkyl group can be substituted are selected from the group consisting of hydroxyl, halo (including independently F, Cl, Br, and I), amino, alkylamino, arylamino, alkoxy, aryloxy, nitro, cyano, carboxamido, carboxylate, thio, alkylthio, azido, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference. In one embodiment, the alkyl can be, for example, $CF_3$, $CH_2CF_3$, $CCl_3$, or cyclopropyl. In the text, whenever the term C(alkyl range) is used, the term independently includes each member of that class as if specifically and separately set out.

The term lower alkyl, as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The term alkylamino or arylamino refers to an amino group that has one or two alkyl or aryl substituents, respectively.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term aryl, as used herein, and unless otherwise specified, refers to phenyl, biphenyl, or naphthyl, and preferably phenyl. The term includes both substituted and unsubstituted moieties. The aryl group can be substituted with one or more moieties selected from the group consisting of alkyl, halo (independently F, Cl, Br, or I), hydroxyl, amino, alkylamino, arylamino, alkoxy, aryloxy, nitro, cyano, carboxamido, carboxylate, thio, alkylthio, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term alkaryl or alkylaryl refers to an alkyl group with an aryl substituent. The term aralkyl or arylalkyl refers to an aryl group with an alkyl substituent.

The term halo, as used herein, includes chloro, bromo, iodo, and fluoro.

The term purine or pyrimidine base includes, but is not limited to, adenine, $N^6$-alkylpurines, $N^6$-acylpurines (wherein acyl is C(O)(alkyl, aryl, alkylaryl, or arylalkyl), $N^6$-benzylpurine, $N^6$-halopurine, $N^6$-vinylpurine, $N^6$-acetylenic purine, $N^6$-acyl purine, $N^6$-hydroxyalkyl purine, $N^6$-thioalkyl purine, $N^2$-alkylpurines, $N^2$-alkyl-6-thiopurines, thymine, cytosine, 5-fluorocytosine, 5-methylcytosine, 6-azapyrimidine, including 6-azacytosine, 2- and/or 4-mercaptopyrmidine, uracil, 5-halouracil, including 5-fluorouracil, $C^5$-alkylpyrimidines, $C^5$-benzylpyrimidines, $C^5$-halopyrimidines, $C^5$-vinylpyrimidine, $C^5$-acetylenic pyrimidine, $C^5$-acyl pyrimidine, $C^5$-hydroxyalkyl purine, $C^5$-amidopyrimidine, $C^5$-cyanopyrimidine, $C^5$-nitropyrimidine, $C^5$-aminopyrimidine, $N^2$-alkylpurines, $N^2$-alkyl-6-thiopurines, 5-azacytidinyl, 5-azauracilyl, triazolopyridinyl, imidazolopyridinyl, pyrrolopyrimidinyl, pyrazolopyrimidinyl,

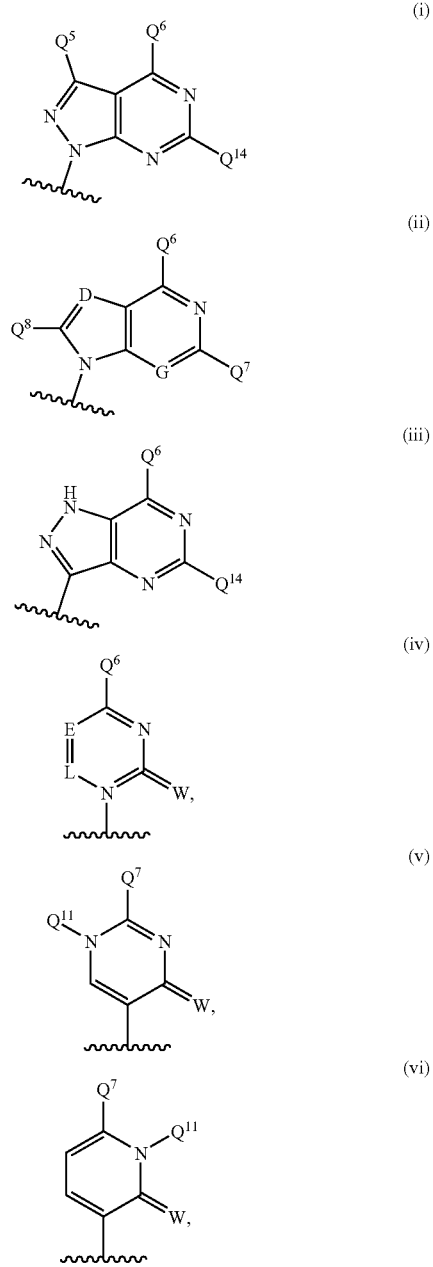

wherein A, G, and L are each independently CH or N;

D is N, CH, C—CN, C—$NO_2$, C—$C_{1-3}$ alkyl, C—NH-CONH$_2$, C—CONQ$^{11}$Q$^{11}$, C—CSNQ$^{11}$Q$^{11}$, CCOOQ$^{11}$, C—C(=NH)NH$_2$, C-hydroxy, C—$C_{1-3}$alkoxy, C-amino, C—$C_{1-4}$ alkylamino, C-di($C_{1-4}$ alkyl)amino, C-halogen, C-(1,3-oxazol-2-yl), C-(1,3-thiazol-2-yl), or C-(imidazol- 2-yl); wherein alkyl is unsubstituted or substituted with one to three groups independently selected from halogen, amino, hydroxy, carboxy, and $C_{1-3}$ alkoxy;

E is N or $CQ^5$;

W is O, S, or NR;

R is H, OH, alkyl;

$Q^6$ is H, OH, SH, $NH^2$, $C_{1-4}$ alkylamino, di($C_{1-4}$ alkyl) amino, $C_{3-6}$ cycloalkylamino, halogen, $C_{1-4}$ alkyl, $C_{1-4}$ alkoxy, or $CF_3$;

$Q^5$ is H, $C_{1-6}$ alkyl, $C_{2-6}$ alkenyl, $C_{2-6}$ alkynyl, $C_{1-4}$ alkylamino, $CF_3$, halogen, N, CN, $NO_2$, $NHCONH_2$, $CONQ^{11}Q^{11}$, $CSNQ^{11}Q^{11}$, $COOQ^{11}$, $C(=NH)NH_2$, hydroxy, $C_{1-3}$ alkoxy, amino, $C_{1-4}$ alkylamino, di($C_{1-4}$ alkyl)amino, halogen, 1,3-oxazol-2-yl, 1,3-thiazol-2-yl, or imidazol-2-yl; wherein alkyl is unsubstituted or substituted with one to three groups independently selected from halogen, amino, hydroxy, carboxy, and $C_{1-3}$ alkoxy;

$Q^7$ and $Q^{14}$ are each independently selected from the group consisting of H, $CF_3$, OH, SH, OR, SR $C_{1-4}$ alkyl, amino, $C_{1-4}$ alkylamino, $C_{3-6}$ cycloalkylamino, and di($C_{1-4}$ alkyl) amino;

$Q^{11}$ is independently H or $C_{1-6}$ alkyl;

$Q^8$ is H, halogen, CN, carboxy, $C_{1-4}$ alkyloxycarbonyl, $N_3$, amino, $C_{1-4}$ alkylamino, di($C_{1-4}$ alkyl)amino, hydroxy, $C_{1-6}$ alkoxy, $C_{1-6}$ alkylthio, $C_{1-6}$ alkylsulfonyl, ($C_{1-4}$ alkyl)$_{0-2}$ aminomethyl, N, CN, $NO_2$, $C_{1-3}$ alkyl, $NHCONH_2$, $CONQ^{11}Q^{11}$, $CSNQ^{11}Q^{11}$, $COOQ^{11}$, $C(=NH)NH_2$, 1,3-oxazol-2-yl, 1,3-thiazol-2-yl, or imidazol-2-yl, wherein alkyl is unsubstituted or substituted with one to three groups independently selected from halogen, amino, hydroxy, carboxy, and $C_{1-3}$ alkoxy;

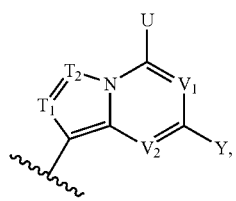

(A)

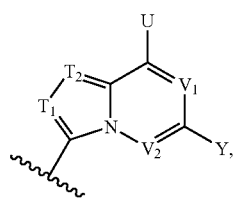

(B)

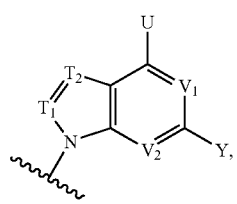

(C)

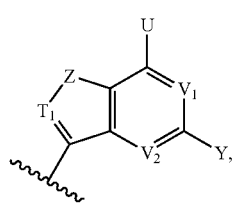

(D)

-continued

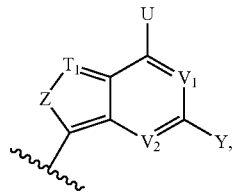

(E)

wherein:

$T_1$ and $T_2$ are independently selected from N, CH, or C-$Q^{16}$;

$Q^{16}$, U, and Y are independently selected from is H, OH, substituted or unsubstituted alkyl, substituted or unsubstituted alkenyl, substituted or unsubstituted alkynyl, cycloalkyl, CO-alkyl, CO-aryl, CO-alkoxyalkyl, chloro, bromo, fluoro, iodo, $OR^4$, $NR^4R^5$ or $SR^5$, Br-vinyl, —O-alkyl, —O-alkenyl, —O-alkynyl, —O-aryl, —O-aralkyl, —O-acyl, —O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, CN, $N_3$, COOH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mCOOH$, $(CH_2)_mCN$, $(CH_2)_mNO_2$, $(CH_2)_mCONH_2$, $C_{1-4}$ alkylamino, di($C_{1-4}$ alkyl)amino, $C_{3-6}$ cycloalkylamino, $C_{1-4}$ alkoxy, $C_{1-4}$ alkoxycarbonyl, $C_{1-6}$ alkylthio, $C_{1-6}$ alkylsulfonyl, ($C_{1-4}$ alkyl)$_{0-2}$ aminomethyl, or —NHC(=NH)$NH_2$;

$R^4$ and $R^5$ are independently selected from hydrogen, acyl (including lower acyl), or alkyl (including but not limited to methyl, ethyl, propyl and cyclopropyl);

m is 0, 1, 2, 3, 4, 5, 6, 7, 8, 9, or 10;

Z is S, SO, $SO_2$, C=O, or $NQ^{20}$;

$Q^{20}$ is H or alkyl; and $V_1$ and $V_2$ are independently selected from CH or N;

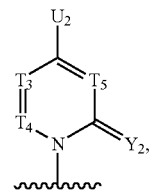

(F)

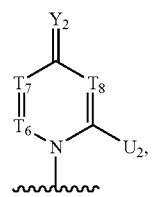

(G)

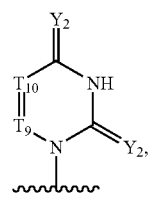

(H)

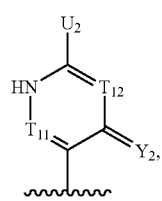

(I)

wherein:

$T_3$ and $T_4$ are independently selected from N or $CQ^{22}$;

$Q^{22}$ is independently selected from H, OH, substituted or unsubstituted alkyl, substituted or unsubstituted alkenyl, substituted or unsubstituted alkynyl, cycloalkyl, CO-alkyl, CO-aryl, CO-alkoxyalkyl, chloro, bromo, fluoro, iodo, $OR^4$, $NR^4R^5$ or $SR^5$, Br-vinyl, —O-alkyl, —O-alkenyl, —O-alkynyl, —O-aryl, —O-aralkyl, —O-acyl, —O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, CN, $N_3$, COOH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mCOOH$, $(CH_2)_mCN$, $(CH_2)_mNO_2$, $(CH_2)_mCONH_2$, $C_{1-4}$ alkylamino, di($C_{1-4}$alkyl)amino, $C_{3-6}$ cycloalkylamino, $C_{1-4}$ alkoxy, $C_{1-4}$ alkoxycarbonyl, $C_{1-6}$ alkylthio, $C_{1-6}$ alkylsulfonyl, $(C_{1-4}$ alkyl$)_{0-2}$ aminomethyl, or —NHC(=NH)$NH_2$;

$R^4$ and $R^5$ are independently selected from hydrogen, acyl (including lower acyl), or alkyl (including but not limited to methyl, ethyl, propyl and cyclopropyl);

m is 0, 1, 2, 3, 4, 5, 6, 7, 8, 9, or 10;

$T_6$, $T_7$, $T_8$, $T_9$, $T_{10}$, $T_{11}$, and $T_{12}$ are independently selected from N or CH;

$U_2$ is H, straight chained, branched or cyclic alkyl, CO-alkyl, CO-aryl, CO-alkoxyalkyl, chloro, bromo, fluoro, iodo, $OR^4$, $NR^4R^5$ or $SR^5$;

$Y_2$ is O, S, NH, NR or $CQ^{24}Q^{26}$ where R is H, OH, or alkyl;

$Q^{24}$ and $Q^{26}$ are independently selected from H, alkyl, straight chained, branched or cyclic alkyl, CO-alkyl, CO-aryl, CO-alkoxyalkyl, chloro, bromo, fluoro, iodo, $OR^4$, $NR^4R^5$ or $SR^5$;

Further examples of purine bases include, but are not limited to, guanine, adenine, hypoxanthine, 2,6-diaminopurine, and 6-chloropurine. Functional oxygen and nitrogen groups on the base can be protected as necessary or desired. Suitable protecting groups are well known to those skilled in the art, and include trimethylsilyl, dimethylhexylsilyl, t-butyldimethylsilyl, and t-butyldiphenylsilyl, trityl, alkyl groups, and acyl groups such as acetyl and propionyl, methanesulfonyl, and p-toluenesulfonyl.

The term acyl refers to a carboxylic acid ester in which the non-carbonyl moiety of the ester group is selected from straight, branched, or cyclic alkyl or lower alkyl, optionally substituted amido, alkoxyalkyl including methoxymethyl, aralkyl including benzyl, aryloxyalkyl such as phenoxymethyl, aryl including phenyl optionally substituted with chloro, bromo, fluoro, iodo, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group.

The term "lower acyl" refers to an acyl group in which the non-carbonyl moiety is a lower alkyl.

As used herein, the term "substantially free of" or "substantially in the absence of" refers to a nucleoside composition that includes at least 95% to 98% by weight, and even more preferably 99% to 100% by weight, of the designated enantiomer of that nucleoside. In a preferred embodiment, in the methods and compounds of this invention, the compounds are substantially free of enantiomers.

Similarly, the term "isolated" refers to a nucleoside composition that includes at least 95% to 98% by weight, and even more preferably 99% to 100% by weight, of the nucleoside, the remainder comprising other chemical species or enantiomers.

The term "independently" is used herein to indicate that the variable which is independently applied varies independently from application to application. Thus, in a compound such as R"XYR", wherein R" is "independently carbon or nitrogen," both R" can be carbon, both R" can be nitrogen, or one R" can be carbon and the other R" nitrogen.

The term host, as used herein, refers to an unicellular or multicellular organism in which the virus can replicate, including cell lines and animals, and preferably a human. Alternatively, the host can be carrying a part of the hepatitis C viral genome, whose replication or function can be altered by the compounds of the present invention. The term host specifically refers to infected cells, cells transfected with all or part of the HCV genome and animals, in particular, primates (including chimpanzees) and humans. In most animal applications of the present invention, the host is a human patient. Veterinary applications, in certain indications, however, are included in the present invention (such as chimpanzees).

The term "pharmaceutically acceptable salt or prodrug" is used throughout the specification to describe any pharmaceutically acceptable form (such as an ester, phosphate ester, salt of an ester or a related group) of a nucleoside compound which, upon administration to a patient, provides the nucleoside compound. Pharmaceutically acceptable salts include those derived from pharmaceutically acceptable inorganic or organic bases and acids. Suitable salts include those derived from alkali metals such as potassium and sodium, alkaline earth metals such as calcium and magnesium, among numerous other acids well known in the pharmaceutical art. Pharmaceutically acceptable prodrugs refer to a compound that is metabolized, for example hydrolyzed or oxidized, in the host to form the compound of the present invention. Typical examples of prodrugs include compounds that have biologically labile protecting groups on a functional moiety of the active compound. Prodrugs include compounds that can be oxidized, reduced, aminated, deaminated, hydroxylated, dehydroxylated, hydrolyzed, dehydrolyzed, alkylated, dealkylated, acylated, deacylated, phosphorylated, dephosphorylated to produce the active compound. The compounds of this invention possess antiviral activity against HCV, or are metabolized to a compound that exhibits such activity.

III. Nucleotide Salt or Prodrug Formulations

In cases where compounds are sufficiently basic or acidic to form stable nontoxic acid or base salts, administration of the compound as a pharmaceutically acceptable salt may be appropriate. Examples of pharmaceutically acceptable salts are organic acid addition salts formed with acids, which form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including, sulfate, nitrate, bicarbonate, and carbonate salts.

Pharmaceutically acceptable salts may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Any of the nucleosides described herein can be administered as a nucleotide prodrug to increase the activity, bioavailability, stability or otherwise alter the properties of the nucleoside. A number of nucleotide prodrug ligands are known. In general, alkylation, acylation or other lipophilic modification of the mono, di or triphosphate of the nucleoside will increase the stability of the nucleotide. Examples of substituent groups that can replace one or more hydrogens on the phosphate moiety are alkyl, aryl, steroids, carbohydrates, including sugars, 1,2-diacylglycerol and alcohols. Many are described in R. Jones and N. Bischofberger, *Antiviral Research*, 27 (1995) 1–17. Any of these can be used in combination with the disclosed nucleosides to achieve a desired effect.

The active nucleoside can also be provided as a 5'-phosphoether lipid or a 5'-ether lipid, as disclosed in the following references, which are incorporated by reference herein: Kucera, L. S., N. Iyer, E. Leake, A. Raben, Modest E. K., D. L. W., and C. Piantadosi. 1990. "Novel membrane-interactive ether lipid analogs that inhibit infectious HIV-1 production and induce defective virus formation." *AIDS Res. Hum. Retro Viruses*. 6:491–501; Piantadosi, C., J. Marasco C. J., S. L. Morris-Natschke, K. L. Meyer, F. Gumus, J. R. Surles, K. S. Ishaq, L. S. Kucera, N. Iyer, C. A. Wallen, S. Piantadosi, and E. J. Modest. 1991. "Synthesis and evaluation of novel ether lipid nucleoside conjugates for anti-HIV activity." *J. Med. Chem.* 34:1408.1414; Hosteller, K. Y., D. D. Richman, D. A. Carson, L. M. Stuhmiller, G. M. T. van Wijk, and H. van den Bosch. 1992. "Greatly enhanced inhibition of human immunodeficiency virus type 1 replication in CEM and HT4-6C cells by 3'-deoxythymidine diphosphate dimyristoylglycerol, a lipid prodrug of 3,-deoxythymidine." *Antimicrob. Agents Chemother.* 36:2025.2029; Hosetler, K. Y., L. M. Stuhmiller, H. B. Lenting, H. van den Bosch, and D. D. Richman, 1990. "Synthesis and antiretroviral activity of phospholipid analogs of azidothymidine and other antiviral nucleosides." *J. Biol. Chem.* 265:61127.

Nonlimiting examples of U.S. patents that disclose suitable lipophilic substituents that can be covalently incorporated into the nucleoside, preferably at the 5'-OH position of the nucleoside or lipophilic preparations, include U.S. Pat. Nos. 5,149,794 (Sep. 22, 1992, Yatvin et al.); 5,194,654 (Mar. 16, 1993, Hostetler et al., 5,223,263 (Jun. 29, 1993, Hostetler et al.); 5,256,641 (Oct. 26, 1993, Yatvin et al.); 5,411,947 (May 2, 1995, Hostetler et al.); 5,463,092 (Oct. 31, 1995, Hostetler et al.); 5,543,389 (Aug. 6, 1996, Yatvin et al.); 5,543,390 (Aug. 6, 1996, Yatvin et al.); 5,543,391 (Aug. 6, 1996, Yatvin et al.); and 5,554,728 (Sep. 10, 1996; Basava et al.), all of which are incorporated herein by reference. Foreign patent applications that disclose lipophilic substituents that can be attached to the nucleosides of the present invention, or lipophilic preparations, include WO 89/02733, WO 90/00555, WO 91/16920, WO 91/18914, WO 93/00910, WO 94/26273, WO 96/15132, EP 0 350 287, EP 93917054.4, and WO 91/19721.

IV. Combination and Alternation Therapy

It has been recognized that drug-resistant variants of HCV can emerge after prolonged treatment with an antiviral agent. Drug resistance most typically occurs by mutation of a gene that encodes for an enzyme used in viral replication. The efficacy of a drug against HCV infection can be prolonged, augmented, or restored by administering the compound in combination or alternation with a second, and perhaps third, antiviral compound that induces a different mutation from that caused by the principle drug. Alternatively, the pharmacokinetics, biodistribution or other parameter of the drug can be altered by such combination or alternation therapy. In general, combination therapy is typically preferred over alternation therapy because it induces multiple simultaneous stresses on the virus.

Any of the HCV treatments described in the Background of the Invention can be used in combination or alternation with the compounds described in this specification. Non-limiting examples include:

(1) an interferon and/or ribavirin (Battaglia, A. M. et al., *Ann. Pharmacother.* 34:487–494, 2000); Berenguer, M. et al. *Antivir. Ther.* 3(Suppl. 3):125–136, 1998);

(2) Substrate-based NS3 protease inhibitors (Attwood et al., *Antiviral peptide derivatives, PCT WO* 98/22496, 1998; Attwood et al., *Antiviral Chemistry and Chemotherapy* 10.259–273, 1999; Attwood et al., Preparation and use of amino acid derivatives as anti-viral agents, German Patent Publication DE 19914474; Tung et al. Inhibitors of serine proteases, particularly hepatitis C virus NS3protease, PCT WO 98/17679), including alphaketoamides and hydrazinoureas, and inhibitors that terminate in an electrophile such as a boronic acid or phosphonate. Llinas-Brunet et al, Hepatitis C inhibitor peptide analogues, PCT WO 99/07734.

(3) Non-substrate-based inhibitors such as 2,4,6-trihydroxy-3-nitro-benzamide derivatives(Sudo K. et al., *Biochemical and Biophysical Research Communications*, 238: 643–647, 1997; Sudo K. et al. *Antiviral Chemistry and Chemotherapy* 9:186, 1998), including RD3–4082 and RD3–4078, the former substituted on the amide with a 14 carbon chain and the latter processing a para-phenoxyphenyl group;

(4) Thiazolidine derivatives which show relevant inhibition in a reverse-phase HPLC assay with an NS3/4A fusion protein and NS5A/5B substrate (Sudo K. et al., *Antiviral Research* 32:9–18, 1996), especially compound RD-1-6250, possessing a fused cinnamoyl moiety substituted with a long alkyl chain, RD4 6205 and RD4 6193;

(5) Thiazolidines and benzanilides identified in Kakiuchi N. et al. *J. EBS Letters* 421:217–220; Takeshita N. et al. *Analytical Biochemistry* 247:242–246, 1997;

(6) A phenanthrenequinone possessing activity against HCV protease in a SDS-PAGE and autoradiography assay isolated from the fermentation culture broth of *Streptomyces* sp., Sch 68631 (Chu M. et al., *Tetrahedron Letters* 37:7229–7232, 1996), and Sch 351633, isolated from the fungus *Penicillium griscofuluum*, which demonstrates activity in a scintillation proximity assay (Chu M. et al., *Bioorganic and Medicinal Chemistry Letters* 9:1949–1952);

(7) Selective NS3 inhibitors based on the macromolecule elgin c, isolated from leech (Qasim M. A. et al., *Biochemistry* 36:1598–1607, 1997);

(8) HCV helicase inhibitors (Diana G. D. et al., Compounds, compositions and methods for treatment of hepatitis C, U.S. Pat. No. 5,633,358; Diana G. D. et al., Piperidine derivatives, pharmaceutical compositions thereof and their use in the treatment of hepatitis C, PCT WO 97/36554);

(9) HCV polymerase inhibitors such as nucleotide analogues, gliotoxin (Ferrari R. et al. *Journal of Virology* 73:1649–1654, 1999), and the natural product cerulenin (Lohmann V. et al., *Virology* 249:108–118, 1998);

(10) Antisense phosphorothioate oligodeoxynucleotides (S-ODN) complementary to sequence stretches in the 5' non-coding region (NCR) of the HCV (Alt M. et al., *Hepatology* 22:707–717, 1995), or nucleotides 326–348 comprising the 3' end of the NCR and nucleotides 371–388 located in the core coding region of the IICV RNA (Alt M. et al., *Archives of Virology* 142:589–599, 1997; Galderisi U. et al., *Journal of Cellular Physiology* 181:251–257, 1999);

(11) Inhibitors of IRES-dependent translation (Ikeda N et al., Agent for the prevention and treatment of hepatitis C, Japanese Patent Publication JP-08268890; Kai Y. et al. *Prevention and treatment of viral diseases*, Japanese Patent Publication JP-10101591);

(12) Nuclease-resistant ribozymes. (Maccjak D. J. et al., *Hepatology* 30 abstract 995, 1999); and

(13) Other miscellaneous compounds including 1-aminoalkylcyclohexanes (U.S. Pat. No. 6,034,134 to Gold et al.), alkyl lipids (U.S. Pat. No. 5,922,757 to Chojkier et al.), vitamin E and other antioxidants (U.S. Pat. No. 5,922,757 to Chojkier et al.), squalene, amantadine, bile acids (U.S. Pat. No. 5,846,964 to Ozeki et al.), N-(phosphonoacetyl)-L-aspartic acid, (U.S. Pat. No. 5,830,905 to Diana et al.), benzenedicarboxamides (U.S. Pat. No. 5,633,388 to Diana et al.), polyadenylic acid derivatives (U.S. Pat. No. 5,496,546 to Wang et al.), 2',3'-dideoxylnosine (U.S. Pat. No. 5,026,687 to Yarchoan et al.), and benzimidazoles (U.S. Pat. No. 5,891,874 to Colacino et al.); and

(14) PEGASYS (pegylated interferon alfa-2a) by Roche, INFERGEN (interferon alfacon-1) by InterMune, OMNIFERON (natural interferon) by Viragen, ALBUFERON by Human Genome Sciences, REBIF (interferon beta-1a) by Ares-Serono, Omega Interferon by BioMedicine, Oral Interferon Alpha by Amarillo Biosciences, Interferon gamma-1b by InterMune, Interleukin-10 by Schering-Plough, IP-501 by Interneuron, Merimebodib VX-497 by Vertex, AMANTADINE (Symmetrel) by Endo Labs Solvay, HEPTAZYME by RPI, IDN-6556 by Idun Pharma., XTL-002 by XTL., HCV/MF59 by Chiron, CIVACIR by NABI, LEVOVIRIN by ICN, VIRAMIDINE by ICN, ZADAXIN (thymosin alfa-1) by Sci Clone, CEPLENE (histamine dihydrochloride) by Maxim, VX 950/LY 570310 by Vertex/Eli Lilly, ISIS 14803 by Isis Pharmaceutical/Elan, IDN-6556 by Idun Pharmaceuticals, Inc. and JTK 003 by AKROS Pharma.

V. Pharmaceutical Compositions

Hosts, including humans, infected with HCV or another organism replicating through a RNA-dependent RNA viral polymerase, can be treated by administering to the patient an effective amount of the active compound or a pharmaceutically acceptable prodrug or salt thereof in the presence of a pharmaceutically acceptable carrier or diluent. The active materials can be administered by any appropriate route, for example, orally, parenterally, intravenously, intradermally, subcutaneously, or topically, in liquid or solid form.

A preferred dose of the compound for HCV will be in the range from about 1 to 50 mg/kg, preferably 1 to 20 mg/kg, of body weight per day, more generally 0.1 to about 100 mg per kilogram body weight of the recipient per day. The effective dosage range of the pharmaceutically acceptable salts and prodrugs can be calculated based on the weight of the parent nucleoside to be delivered. If the salt or prodrug exhibits activity in itself, the effective dosage can be estimated as above using the weight of the salt or prodrug, or by other means known to those skilled in the art.

The compound is conveniently administered in unit any suitable dosage form, including but not limited to one containing 7 to 3000 mg, preferably 70 to 1400 mg of active ingredient per unit dosage form. A oral dosage of 50–1000 mg is usually convenient.

Ideally the active ingredient should be administered to achieve peak plasma concentrations of the active compound of from about 0.2 to 70 μM, preferably about 1.0 to 10 μM. This may be achieved, for example, by the intravenous injection of a 0.1 to 5% solution of the active ingredient, optionally in saline, or administered as a bolus of the active ingredient.

The concentration of active compound in the drug composition will depend on absorption, inactivation and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound can be administered as a component of an elixir, suspension, syrup, wafer, chewing gum or the like. A syrup may contain, in addition to the active compounds, sucrose as a sweetening agent and certain preservatives, dyes and colorings and flavors.

The compound or a pharmaceutically acceptable prodrug or salts thereof can also be mixed with other active materials that do not impair the desired action, or with materials that supplement the desired action, such as antibiotics, antifungals, anti-inflammatories, or other antivirals, including other nucleoside compounds. Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters and polylactic acid. Methods for preparation of such formulations will be apparent to those skilled in the art. The materials can also be obtained commercially from Alza Corporation.

Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound or its monophosphate, diphosphate, and/or triphosphate derivatives is then introduced into the container. The container is then swirled by hand to free lipid material from the sides of the container and to disperse lipid aggregates, thereby forming the liposomal suspension.

VI. Processes for the Preparation of Active Compounds

The nucleosides of the present invention can be synthesized by any means known in the art. In particular, the synthesis of the present nucleosides can be achieved by either alkylating the appropriately modified sugar, followed by glycosylation or glycosylation followed by alkylation of the nucleoside, though preferably alkylating the appropriately modified sugar, followed by glycosylation. The following non-limiting embodiments illustrate some general methodology to obtain the nucleosides of the present invention.

General Synthesis of 4'-C-Branched Nucleosicles

4'-C-Branched ribonucleosides of the following structure:

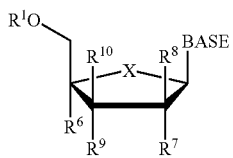

wherein BASE is a purine or pyrimidine base as defined herein;

$R^7$ and $R^9$ are independently hydrogen, $OR^2$, hydroxy, alkyl (including lower alkyl), azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$;

$R^8$ and $R^{10}$ are independently H, alkyl (including lower alkyl), chlorine, bromine or iodine;

alternatively, $R^7$ and $R^9$, $R^7$ and $R^{10}$, $R^8$ and $R^9$, or $R^8$ and $R^{10}$ can come together to form a pi bond;

$R^1$ and $R^2$ are independently H; phosphate (including monophosphate, diphosphate, triphosphate, or a stabilized phosphate prodrug); acyl (including lower acyl); alkyl (including lower alkyl); sulfonate ester including alkyl or arylalkyl sulfonyl including methanesulfonyl and benzyl, wherein the phenyl group is optionally substituted with one or more substituents as described in the definition of aryl given herein; a lipid, including a phospholipid; an amino acid; a carbohydrate; a peptide; a cholesterol; or other pharmaceutically acceptable leaving group which when administered in vivo is capable of providing a compound wherein $R^1$ is independently H or phosphate;

$R^6$ is an alkyl, halogeno-alkyl (i.e. $CF_3$), alkenyl, or alkynyl (i.e. allyl); and X is OS, $SO_2$ or $CH_2$ can be prepared by the following general method.

Modification from the Pentodialdo-furanose

The key starting material for this process is an appropriately substituted pentodialdo-furanose. The pentodialdo-furanose can be purchased or can be prepared by any known means including standard epimerization, substitution and cyclization techniques.

In a preferred embodiment, the pentodialdo-furanose is prepared from the appropriately substituted hexose. The hexose can be purchased or can be prepared by any known means including standard epimerization (e.g. via alkaline treatment), substitution and coupling techniques. The hexose can be either in the furanose form, or cyclized via any means known in the art, such as methodology taught by Townsend *Chemistry of Nucleosides and Nucleotides*, Plenum Press, 1994, preferably by selectively protecting the hexose, to give the appropriate hexafuranose.

The 4'-hydroxymethylene of the hexafuranose then can be oxidized with the appropriate oxidizing agent in a compatible solvent at a suitable temperature to yield the 4'-aldo-modified sugar. Possible oxidizing agents are Swern reagents, Jones reagent (a mixture of chromic acid and sulfuric acid), Collins's reagent (dipyridine Cr(VI) oxide, Corey's reagent (pyridinium chlorochromate), pyridinium dichromate, acid dichromate, potassium permanganate, $MnO_2$, ruthenium tetroxide, phase transfer catalysts such as chromic acid or permanganate supported on a polymer, $Cl_2$-pyridine, $H_2O_2$-ammonium molybdate, $NaBrO_2$-CAN, NaOCl in HOAc, copper chromite, copper oxide, Raney nickel, palladium acetate, Meerwin-Pondorf-Verley reagent (aluminum t-butoxide with another ketone) and N-bromosuccinimide, though preferably using $H_3PO_4$, DMSO and DCC in a mixture of benzene/pyridine at room temperature.

Then, the pentodialdo-furanose can be optionally protected with a suitable protecting group, preferably with an acyl or silyl group, by methods well known to those skilled in the art, as taught by Greene et al. Protective Groups in Organic Synthesis, John Wiley and Sons, Second Edition, 1991. In the presence of a base, such as sodium hydroxide, the protected pentodialdo-furanose can then be coupled with a suitable electrophilic alkyl, halogeno-alkyl (i.e. $CF_3$), alkenyl or alkynyl (i.e. allyl), to obtain the 4'-alkylated sugar. Alternatively, the protected pentodialdo-furanose can be coupled with the corresponding carbonyl, such as formaldehyde, in the presence of a base, such as sodium hydroxide, with the appropriate polar solvent, such as dioxane, at a suitable temperature, which can then be reduced with an appropriate reducing agent to give the 4'-alkylated sugar. In one embodiment, the reduction is carried out using PhOC(S)Cl, DMAP, preferably in acetonitrile at room temperature, followed by treatment of ACCN and TMSS refluxed in toluene.

The optionally activated sugar can then be coupled to the BASE by methods well known to those skilled in the art, as taught by Townsend *Chemistry of Nucleosides and Nucleotides*, Plenum Press, 1994. For example, an acylated sugar can be coupled to a silylated base with a lewis acid, such as tin tetrachloride, titanium tetrachloride or trimethylsilyltriflate in the appropriate solvent at a suitable temperature.

Subsequently, the nucleoside can be deprotected by methods well known to those skilled in the art, as taught by Greene et al. *Protective Groups in Organic Synthesis*, John Wiley and Sons, Second Edition, 1991.

In a particular embodiment, the 4'-C-branched ribonucleoside is desired. Alternatively, deoxyribo-nucleosides is desired. To obtain these deoxyribo-nucleosides, a formed ribo-nucleoside can optionally be protected by methods well known to those skilled in the art, as taught by Greene et al. *Protective Groups in Organic Synthesis*, John Wiley and Sons, Second Edition, 1991, and then the 2'-OH can be reduced with a suitable reducing agent. Optionally, the 2'-hydroxyl can be activated to facilitate reduction; i.e. via the Barton reduction.

In another embodiment of the invention, the L-enantiomers are desired. Therefore, the L-enantiomers can be corresponding to the compounds of the invention can be prepared following the same foregoing general methods, beginning with the corresponding L-pentodialdo-furanose as starting material.

The present invention is described by way of illustration, in the following examples. It will be understood by one of ordinary skill in the art that these examples are in no way limiting and that variations of detail can be made without departing from the spirit and scope of the present invention.

VII. EXAMPLES

Melting points were determined in open capillary tubes on a Büchi B-545 apparatus and are uncorrected. The UV absorption spectra were recorded on an Uvikon XS spectrophotometer (99–9089). $^1$H-NMR spectra were run at room temperature in DMSO-$d_6$ or CDCl$_3$ with a Bruker AC 200, 250 or 400 spectrometer. Chemical shifts are given in ppm, DMSO-$d_6$ or CDCl$_3$ being set at 2.49 or 7.26 ppm as reference. Deuterium exchange, decoupling experiments or 2D-COSY spectra were performed in order to confirm proton assignments. Signal multiplicities are represented by s (singlet), d (doublet), dd (doublet of doublets), t (triplet), q (quadruplet), br (broad), m (multiplet). All J-values are in Hz. FAB mass spectra were recorded in the positive–(FAB>0) or negative–(FAB>0) ion mode on a JEOL JMS DX 300 mass spectrometer; the matrix was a mixture (50:50, v/v) of glycerol and thioglycerol (GT). Thin layer chromatography was performed on precoated aluminum sheets of Silica Gel 60 F$_{254}$ (Merck, Art. 5554), visualization of products being accomplished by UV absorbency followed by charring with 10% ethanolic sulfuric acid and heating. Column chromatography was carried out on Silica Gel 60 (Merck, Art. 9385) at atmospheric pressure.

Example 1

Preparation of 1-O-Methyl-2,3-O-isopropylidene-β-D-ribofuranose (1)

The title compound can be prepared according to a published procedure (Leonard, N. J.; Carraway, K. L. "5-Amino-5-deoxyribose derivatives. Synthesis and use in the preparation of "reversed" nucleosides" *J. Heterocycl. Chem.* 1966, 3, 485–489).

A solution of 50.0 g (0.34 mole) of dry D-ribose in 1.0 L of acetone, 100 mL of 2,2-dimethoxypropane, 200 mL of methanol containing 20 mL of methanol saturated with hydrogen chloride at 0° C. was stirred overnight at room temperature. The resulting solution was neutralized with pyridine and evaporated under reduced pressure. The resulting oil was partitioned between 400 mL of water and 400 mL of methylene chloride. The water layer was extracted twice with methylene chloride (400 mL). The combined organic extracts were dried over sodium sulfate and evaporated under reduced pressure. The residue was purified by silica gel column chromatography [eluent: stepwise gradient of methanol (1–2%) in methylene chloride] to give pure 1 (52.1 g, 75%) as a yellow syrup. $^1$H-NMR (CDCl$_3$): δ 5.00 (s, 1H, H-1), 4.86 (d, 1H, H-2, $J_{2-3}$=5.9 Hz), 4.61 (d, 1H, H-3, $J_{3-2}$=5.9 Hz), 4.46 (t, 1H, H-4, $J_{4-5}$=2.7 Hz), 3.77–3.61 (m, 2H, H-5 and H-5'), 3.46 (s, 1H, OCH$_3$), 3.0–2.4 (br s, 1H, OH-5), 1.51 (s, 3H CH$_3$), 1.34 (s, 3H CH$_3$); MS (matrix GT): FAB>0 m/z 173 (M−OCH3)$^+$.

Example 2

Preparation of 1-O-Methyl-2,3-O-isopropylidene-β-D-pentodialdo-ribofuranose (2)

The title compound can be prepared according to a published procedure (Jones, G. H.; Moffatt, J. G. Oxidation of carbohydrates by the sulfoxide-carbodiimide and related methods. Oxidation with dicyclohexylcarbodiimide-DMSO, diisopropylcarbodiimide-DMSO, acetic anhydride-DMSO, and phosphorus pentoxide-DMSO: in *Methods in Carbohydrate Chemistry*; Whisler, R. L. and Moffatt, J. L. Eds; Academic Press: New York, 1972; 315–322).

Compound 1 was co-evaporated twice with anhydrous pyridine. Dicyclohexylcarbodi-imide (DCC, 137.8 g, 0.67 mol) was added to a solution of 1 (68.2 g, 0.33 mole) in anhydrous benzene (670 mL), DMSO (500 mL) and pyridine (13.4 mL). To the resulting solution, cooled to 0° C., was added a solution of anhydrous crystalline orthophosphoric acid (16.4 g, 0.167 mmol) in anhydrous DMSO (30 mL). The mixture was stirred for 1.5 hours at 0° C. and 18 hours at room temperature under argon atmosphere, diluted with ethyl acetate (1000 mL). A solution of oxalic acid dihydrate (63.1 g, 038 mol) in DMSO (30 mL) was added and the reaction mixture was stirred at room temperature during 1 hour and then filtered to eliminate precipitated dicyclohexylurea (DCU). The filtrate was concentrated to a volume of about 600 mL under reduced pressure and neutralized with a saturated aqueous sodium hydrogen carbonate solution (400 mL). Brine (200 mL) was added and the organic layer was extracted with ethyl acetate (4×1000 mL). The combined organic layers were concentrated to a volume of about 2000 mL, washed with a saturated aqueous sodium hydrogen carbonate solution (2×700 mL), and with brine (2×700 mL) before being dried over sodium sulfate and evaporated under reduced pressure. A small fraction of the crude residue was purified on silica gel chromatography

[eluent: chloroform/ethyl ether, 8:2] in order to confirm the structure of 2 which was obtained as a pale yellow solid. $^1$H-NMR (CDCl$_3$): δ 9.61 (s, 1H, H-5), 5.12 (s, 1H, H-1), 5.08 (d, 1H, H-2, J$_{2-3}$=5.9 Hz), 4.53 (d, 1H, H-3, J$_{3-2}$=6.0 Hz), 4.51 (s, 1H, H-4), 3.48 (s, 1H, OCH$_3$), 1.56 (s, 3H CH$_3$), 1.36 (s, 3H CH$_3$); MS (matrix GT): FAB>0 m/z 203 (M+H)$^+$, 171 M–OCH$_3$)$^+$.

Example 3

Preparation of 4-C-Hydroxymethyl-1-O-methyl-2,3-O-isopropylidene-β-D-ribofuranose (3)

The title compound can be prepared according to a published procedure (Leland, D. L.; Kotick, M. P. "Studies on 4-C-(hydroxymethyl)pentofuranoses. Synthesis of 9-[4-C-(hydroxymethyl)-a-L-threo-pentofuranosyl]adenine" *Carbohydr. Res.* 1974, 38, C9-C11; Jones, G. H.; Taniguchi, M.; Tegg, D.; Moffatt, J. G. "4'-substituted nucleosides. 5. Hydroxylation of nucleoside 5'-aldehydes" *J. Org. Chem.* 1979, 44, 1309–1317; Gunic, E.; Girardet, J.-L.; Pietrzkowski, Z.; Esler, C.; Wang, G. "Synthesis and cytotoxicity of 4'-C- and 5'-C-substituted Toyocamycins" *Bioorg. Med. Chem.* 2001, 9, 163–170).

To a solution of the crude material (2) obtained above and 37% aqueous formaldehyde (167 mL) in dioxane (830 mL) was added aqueous sodium hydroxyde (2N, 300 mL). The mixture was stirred at room temperature for 4 hours and neutralized by addition of Dowex 50 W×2 (H$^+$ form). The resin was filtered, washed with methanol, and the combined filtrates were concentrated to dryness and coevaporated several times with absolute ethanol. Sodium formate which was precipitated from absolute ethanol was removed by filtration, the filtrate was concentrated to dryness and the residue was purified by silica gel column chromatography [eluent: stepwise gradient of methanol (0–4%) in chloroform] to give pure 3 (42.2 g, 54% from 1), which was recrystallized from cyclohexane. Mp=94–95 (dec.) (lit.94–96.5; 97–98: Refs: 3,4), $^1$H-NMR (DMSO-d$_6$): δ 4.65 (s, 1H, H-1), 4.44–4.37 (m, 3H, H-2, H-3 and OH-6), 4.27 (t, 1H, OH-5, J=5.6 Hz, J=6.0 Hz), 3.42–3.34 (m, 2H, H-5 and H-6) 3.29 (dd, 1H, H-5', J$_{5'-OH}$=5.4 Hz, J5-5'=11.4 Hz), 3.11 (dd, 1H, H-6', J$_{6'-OH}$=5.7 Hz, J6-6'=10.9 Hz), 3.03 (s, 3H, OCH$_3$), 1.48 (s, 3H CH$_3$), 1.05 (s, 3H CH$_3$); MS (matrix GT): FAB>0 m/z 469 (2M+H)$^+$, 235 (M+H)$^+$, 203 (M–OCH$_3$)+ FAB<0 m/z 233 (M–H)$^-$.

Example 4

Preparation of 6-O-Monomethoxytrityl-4-C-hydroxymethyl-1-O-methyl-2,3-O-isopropylidene-β-D-ribofuranose (4)

The title compound can be prepared according to a published procedure (Gunic, E.; Girardet, J.-L.; Pietrzkowski, Z.; Esler, C.; Wang, G. "Synthesis and cytotoxicity of 4'-C- and 5'-C-substituted Toyocamycins" *Bioorg. Med. Chem.* 2001, 9, 163–170).

To a solution of 3 (41.0 g, 175 mmol) in pyridine (700 ml) was added by portions dimethoxytrityl chloride (60.5 g, 178 mmol) at +4° C. The reaction mixture was stirred for 3 hours at room temperature. After addition of methanol, the reaction mixture was concentrated (200 ml) and then dissolved with ethyl acetate (2 L). The organic layer was washed with a 5% aqueous sodium hydrogen carbonate solution, with water and dried over sodium sulfate and then evaporated to dryness. Purification by silica gel column chromatography [eluent: ethyl acetate/hexane 15/85] afforded pure 4 (63.0 g, 68%) as a syrup. $^1$H-NMR (CDCl$_3$): δ 7.5–6.9 (m, 13H, MMTr), 4.89 (s, 1H, H-1), 4.72–4.62 (m, 3H, H-2, H-3 and OH-5), 3.82 (dd, 1H, H-5, J$_{5-OH}$=5.5 Hz, J5-5'=10.5 Hz), 3.79 (s, 6H, OCH3), 3.54 (dd, 1H, H-5', J$_{5'-OH}$=4.9 Hz, J$_{5'-5}$=10.5 Hz), 3.31 (s, 3H, OCH$_3$), 3.24 (d, 1H, H-6, J$_{6-6'}$=9.2 Hz), 3.13 (d, 1H, H-6', J$_{6'-6}$=9.2 Hz), 1.24 (s, 3H CH$_3$), 1.15 (s, 3H CH$_3$); MS (matrix GT): FAB>0 m/z 303 (DMTr)$^+$.

Example 5

Preparation of 5-O-Benzoyl-4-C-hydroxymethyl-1-O-methyl-2,3-O-isopropylidene-β-D-ribo-furanose (5)

The title compound can be prepared according to a published procedure (Gunic, E.; Girardet, J.-L.; Pietrzkowski, Z.; Esler, C.; Wang, G. "Synthesis and cytotoxicity of 4'-C- and 5'-C-substituted Toyocamycins" *Bioorg. Med. Chem.* 2001, 9, 163–170).

To a solution of 4 (2.51 g, 4.68 mmol) in anhydrous pyridine (37 mL) was added under argon benzoyl chloride (1.09 mL, 9.36 mmol) and the reaction mixture was stirred for 13 hours at to room temperature. Then the reaction was cooled to 0° C. and stopped with ice-cold water (100 mL). The water layer was extracted with methylene chloride (3□ 200 mL). The combined organic layers were washed with a saturated aqueous sodium hydrogen carbonate solution (2×150 mL), with water (1×150 mL) and then dried over sodium sulfate and evaporated under reduced pressure. The residue was dissolved in 80% acetic acid (70.2 mL) and the mixture was stirred at room temperature for 3 hr and concentrated to dryness. Purification by silica gel column chromatography [eluent: chloroform] afforded pure 5 (1.40 g, 88%) as a syrup. $^1$H-NMR (CDCl$_3$): δ 8.1–7.4 (m, 5H, C$_6$H$_5$CO), 5.08 (s, 1H, H-1), 4.77 (dd, 2H, H-2 and H-3, J=6.1 Hz, J=8.2 Hz), 4.51 (q, 2H, H-5 and H-5', J=11.5 Hz, J$_{5-5'}$=23.8 Hz), 3.91 (t, 2H, H-6 and H-6', J=12.3 Hz), 4.38 (s, 1H, OCH$_3$), 2.2–1.8 (brs, 1H, OH-6), 1.57 (s, 3H CH$_3$), 1.38 (s, 3H CH$_3$); MS (matrix GT): FAB>0 m/z 677 (2M+H)$^+$, 339 (M+H)$^+$, 307 (M–OCH$_3$)$^+$, 105 (C$_6$H$_5$CO)$^+$ FAB<0 m/z 121 (C$_6$H$_5$CO$_2$)$^-$.

Example 6

Preparation of 5-O-Benzoyl-4-C-methyl-1-O-methyl-2,3-O-isopropylidene-β-D-ribofuranose (6)

The title compound can be prepared according to a published procedure (Gunic, E.; Girardet, J.-L.; Pietrzkowski, Z.; Esler, C.; Wang, G. "Synthesis and cytotoxicity of 4'-C- and 5'-C-substituted Toyocamycins" *Bioorg. Med. Chem.* 2001, 9, 163–170).

A solution of 5 (37.6 g, 0.111 mol), 4-dimethylaminopyridine (DMAP, 40.7 g, 0.333 mol) and phenoxythiocarbonyle chloride in anhydrous acetonitrile (1000 mL) was stirred at room temperature for 1 hour and concentrated to dryness. The residue was dissolved in methylene chloride (500 mL) and successively washed with 0.2 M hydrochloric acid (2×500 mL) and water (500 mL) before being dried over sodium sulfate, evaporated under reduced pressure and coevaporated several times with anhydrous toluene. The crude material was dissolved in anhydrous toluene (880 mL) and tris(trimethylsilyl)silane (TMSS, 42.9 mL, 0.139 mol), and 1,1'-azobis(cyclohexanecarbonitrile) (ACCN, 6.8 g, 27.8 mmol) were added. The reaction mixture was stirred under reflux for 45 minutes, cooled to room temperature and concentrated under reduced pressure. The resulting residue was purified by silica gel column chromatography [eluent: stepwise gradient of diethyl ether (5–20%) in petroleum ether] to give pure 6 (26.4 g, 74%) as a pale yellow syrup. $^1$H-NMR (DMSO-d$_6$): δ 8.0–7.5 (m, 5H, C$_6$H$_5$CO), 4.85 (s, 1H, H-1), 4.63 (dd, 2H, H-2 and H-3, J=6.1 Hz, J=11.6 Hz), 4.24 (d, 1H, H-5, J$_{5\text{-}5'}$=11.1 Hz), 4.10 (d, 1H, H-5', J$_{5'\text{-}5}$=11.1 Hz), 3.17 (s, 1H, OCH$_3$), 1.38 (s, 3H CH$_3$), 1.30 (s, 3H CH$_3$), 1.25 (s, 3H CH$_3$); MS (matrix GT): FAB>0 m/z 291 (M–OCH$_3$)$^+$, 105 (C$_6$H$_5$CO)$^+$ FAB<0 m/z 121 (C$_6$H$_5$CO$_2$)$^-$.

Example 7

Preparation of 5-O-Benzoyl-4-C-methyl-1,2,3-O-acetyl-α,β-D-ribofuranose (7)

Compound 6 (22.5 g, 70 mmol) was suspended in a 80% aqueous acetic acid solution (250 mL). The solution was heated at 100° C. for 3 hours. The volume was then reduced by half and coevaporated with absolute ethanol and pyridine. The oily residue was dissolved in pyridine (280 mL) and then cooled at 0° C. Acetic anhydride (80 mL) and 4-dimethylamino-pyridine (500 mg) were added. The reaction mixture was stirred at room temperature for 3 hours and then concentrated under reduced pressure. The residue was dissolved with ethyl acetate (1 L) and successively washed with a saturated aqueous sodium hydrogen carbonate solution, a 1 M hydrochloric acid and water. The organic layer was dried over sodium sulfate and evaporated under reduced pressure. The resulting residue was purified by silica gel column chromatography [eluent: stepwise gradient of diethyl ether (30–40%) in petroleum ether] to give pure 7 (16.2 g, 60%) as a pale yellow syrup. A small fraction of the material was re-purified on silica gel chromatography [same eluent: system] in order separate the α and the β anomers.

α anomer: $^1$H-NMR (DMSO-d$_6$): δ 8.1–7.5 (m, 5H, C$_6$H$_5$CO), 6.34 (pt, 1H, H-1, J=2.4 Hz, J=2.1 Hz), 5.49 (m, 2H, H-2 and H-3), 4.33 (q, 2H, H-5 and H-5', J=11.6 Hz, J=18.7 Hz), 2.15 (s, 3H, CH$_3$CO$_2$), 2.11 (s, 3H, CH$_3$CO$_2$), 2.07 (S, 3H, CH$_3$CO$_2$), 1.37 (s, 3H, CH$_3$); MS (matrix GT): FAB>0 m/z 335 (M–CH$_3$CO$_2^-$)$^+$, 275 (M–CH$_3$CO$_2^-$+H)$^+$, 105 (C$_6$H$_5$CO)$^+$, 43 (CH$_3$CO)$^+$ FAB<0 m/z 121 (C$_6$H$_5$CO$_2$)$^-$, 59 (CH$_3$CO$_2$)$^-$.

β anomer: $^1$H-NMR (DMSO-d$_6$): δ 8.1–7.5 (m, 5H, C$_6$H$_5$CO), 5.99 (s, 1H, H-1), 5.46 (d, 1H, H-2, J$_{2\text{-}3}$=5.3 HZ), 5.30 (d, 1H, H-2, J$_{2\text{-}3}$=5.3 Hz), 4.39 (d, 1H, H-5, J$_{5\text{-}5'}$=11.7 Hz), 4.19 (d, 1H, H-5', J$_{5'\text{-}5}$=11.7 Hz), 2.10 (s, 3H, CH$_3$CO$_2$), 2.06 (s, 3H, CH$_3$CO$_2$), 2.02 (s, 3H, CH$_3$CO$_2$), 1.30 (s, 3H, CH$_3$); MS (matrix GT): FAB>0 m/z 335 (M–CH$_3$CO$_2^-$)$^+$, 275 (M–CH$_3$CO$_2^-$+H)$^+$, 105 (C$_6$H$_5$CO)$^+$, 43 (CH$_3$CO)$^+$ FAB<0 m/z 121 (C$_6$H$_5$CO$_2$)$^-$, 59 (CH$_3$CO$_2$)$^-$.

Example 8

Preparation of 1-(5-O-Benzoyl-4-C-methyl-2,3-O-acetyl-β-D-ribofuranosyl)uracil (8)

A suspension of uracil (422 mg, 3.76 mmol) was treated with hexamethyldisilazane (HMDS, 21 mL) and a catalytic amount of ammonium sulfate during 17 hours under reflux. After cooling to room temperature, the mixture was evaporated under reduced pressure, and the residue, obtained as a colorless oil, was diluted with anhydrous 1,2-dichloroethane (7.5 mL). To the resulting solution was added 7 (0.99 g, 2.51 mmol) in anhydrous 1,2-dichloroethane (14 mL), followed by addition of trimethylsilyl trifluoromethanesulfonate (TM-STf, 0.97 mL, 5.02 mmol). The solution was stirred for 2.5 hours at room temperature under argon atmosphere, then diluted with chloroform (150 mL), washed with the same volume of a saturated aqueous sodium hydrogen carbonate solution and finally with water (2×100 mL). The organic phase was dried over sodium sulfate, then evaporated under reduced pressure. The resulting crude material was purified by silica gel column chromatography [eluent: stepwise gradient of methanol (0–2%) in chloroform] to afford pure 8 (1.07 g, 95%) as a foam. $^1$H-NMR (DMSO-d6): δ 11.48 (s, 1H, NH), 8.1–7.5 (m, 6H, C$_6$H$_5$CO and H-6), 5.94 (d, 1H, H-1', J$_{1'\text{-}2'}$=3.3 Hz), 5.61 (m, 3H, H-5, H-2' and H-3'), 4.47 (d, 1H, H-5', J$_{5'\text{-}5''}$=11.7 Hz), 4.35 (d, 1H, H-5'', J$_{5''\text{-}5}$=11.7 Hz), 2.12 (s, 3H, CH$_3$CO$_2$), 2.09 (s, 3H, CH$_3$CO$_2$), 1.38 (s, 3H, CH$_3$); MS (matrix GT): FAB>0 m/z 893 (2M+H)$^+$, 447 (M+H)$^+$, 335 (S)$^+$, 113 (BH$_2$)$^+$, 105 (C$_6$H$_5$CO)$^+$, 43 (CH$_3$CO)$^+$ FAB<0 m/z 891 (2M–H)$^-$, 445 (M–H)$^-$, 121 (C$_6$H$_5$CO$_2$)$^-$, 111 (B)$^-$, 59 (CH$_3$CO$_2$)$^-$.

Example 9

Preparation of 1-(4-C-methyl-β-D-ribofuranosyl)uracil (9)

The title compound can be prepared according to a published procedure from 8 (Waga, T.; Nishizaki, T.; Miyakawa, I.; Orhui, H.; Meguro, H. "Synthesis of 4'-C-methylnucleosides" *Biosci. Biotechnol. Biochem.* 1993, 57, 1433–1438).

A solution of 8 (610 mg, 1.37 mmol) in methanolic ammonia (previously saturated at –10° C.) (27 mL) was stirred at room temperature overnight. The solvent was evaporated under reduced pressure and the residue was partitioned between methylene chloride (40 mL) and water (40 mL). The aqueous layer was washed with methylene chloride (2×40 mL), concentrated under reduced pressure and coevaporated several times with absolute ethanol. Recrystallization from a mixture absolute ethanol/methanol gave 9 (215 mg, 61%) as a colorless and crystalline solid. Mp: 226–227 (dec.) (lit. 227: Ref.6); UV (H$_2$O); λ$_{max}$=259 nm (ε=10100), λ$_{min}$=228 nm (ε=2200); HPLC 99.56%, $^1$H-NMR (DMSO-d$_6$): δ 11.28 (s, 1H, NH), 7.89 (d, 1H, H-6, J$_{6\text{-}5}$=8.1 Hz), 5.80 (d, 1H, H-1', J$_{1'\text{-}2'}$=7.1 Hz), 5.64 (d, 1H, H-5, J$_{5\text{-}6}$=8.1 Hz), 5.24 (d, 1H, OH-2', J$_{OH\text{-}2'}$=6.5 Hz), 5.18 (t, 1H, OH-5' J$_{OH\text{-}5'}$=J$_{OH\text{-}5''}$=5.2 Hz), 5.01 (d, 1H, OH-3', J$_{OH\text{-}3'}$=5.0 Hz), 4.28 (dd, 1H, H-2', J=6.5 Hz, J=12.2 Hz), 3.90 (t, 1H, H-3', J$_{3'\text{-}2'}$=J$_{3'\text{-}OH}$=5.1 Hz), 3.30 (m, 2H, H-5' and H-5''), 1.06 (s, 3H, CH$_3$); MS (matrix GT): FAB>0 m/z 517 (2M+H)$^+$, 259 (M+H)$^+$, 147 (S)$^+$ FAB<0 m/z 515 (2M–H)$^-$, 257 (M–H)$^-$.

Example 10

Preparation of 1-(5-O-Benzoyl-4-C-methyl-2,3-O-acetyl-β-D-ribofuranosyl)4-thio-uracil (10)

Lawesson's reagent (926 mg, 2.29 mmol) was added under argon to a solution of 8 (1.46 g, 3.27 mmol) in anhydrous 1,2-dichloroethane (65 mL) and the reaction mixture was stirred overnight under reflux. The solvent was evaporated under reduced pressure and the residue was purified by silica gel column chromatography [eluent: stepwise gradient of methanol (1–2%) in chloroform] to give pure 10 (1.43 g, 95%) as a yellow foam. $^1$H-NMR (DMSO-d$_6$): δ 12.88 (s, 1H, NH), 8.1–7.5 (m, 6H, C$_6$H$_5$CO and H-6), 6.27 (d, 1H, H-1', J$_{1'\text{-}2'}$=7.51 Hz), 5.91 (br s, 1H, H-5) 5.64 (m, 2H, H-2' and H-3'), 4.47 (d, 1H, H-5', J$_{5'\text{-}5''}$=11.7 Hz), 4.36 (d, 1H, H-5', $J_{5'-5'}$=11.7 Hz), 2.11 (s, 3H, $CH_3CO_2$), 2.09 (s, 3H, $CH_3CO_2$), 1.39 (s, 3H, $CH_3$); MS (matrix GT): FAB>0 nm/z 925 $(2M+H)^+$, 463 $(M+H)^+$, 335 $(S)^+$, 129 $(BH_2)^+$, 105 $(C_6H_5CO)^+$, 43 $(CH_3CO)^+$ FAB<0 m/z 461 $(M-H)^-$, 127 $(B)^-$, 121 $(C_6H_5CO_2)^-$, 59 $(CH_3CO_2)^-$.

Example 11

Preparation of 1-(4-C-methyl-β-D-ribofuranosyl)4-thio-uracil (11)

A solution of 10 (500 mg, 1.08 mmol) in methanolic ammonia (previously saturated at −10° C.) (27 mL) was stirred at room temperature overnight. The solvent was evaporated under reduced pressure and the residue was partitioned between methylene chloride (40 ml) and water (40 mL). The aqueous layer was washed with methylene chloride (2×40 mL), concentrated under reduced pressure. The crude material was purified by silica gel column chromatography [eluent: stepwise gradient of methanol (5–7%) in methylene chloride] to give pure 11 (188 mg, 63%), which was lyophilized. Mp: 65–70 (dec.); UV (methanol): $\lambda_{max}$=330 nm ($\epsilon$=20000) 246 nm ($\epsilon$=4200), $\lambda_{min}$=275 nm ($\epsilon$=1500); $^1$H-NMR (DMSO-$d_6$): δ 12.51 (brs, 1H, NH), 7.81 (d, 1H, H-6, $J_{6-5}$=7.6 Hz), 6.30 (d, 1H, H-5, $J_{5-6}$=7.5 Hz), 5.77, (d, 1H, H-1', $J_{1'-2'}$=6.7 Hz), 5.32 (d, 1H, OH-2', $J_{OH-2'}$=6.1 Hz), 5.20 (t, 1H, OH-5' $J_{OH-5'}$=$J_{OH-5''}$=5.2 Hz), 5.03 (d, 1H, OH-3', $J_{OH-3'}$=5.2 Hz), 4.17 (dd, 1H, H-2', J=6.2 Hz, J=12.0 Hz), 3.89 (t, 1H, H-3', $J_{3'-2'}$=$J_{3'-OH'}$=5.1 Hz), 3.35 (m, 2H, H-5' and H-5''), 1.02 (s, 3H, $CH_3$); MS (matrix GT): FAB>0 m/z 275 $(M+H)^+$, 147 $(S)^+$, 129$(BH_2)^+$ FAB<0 m/z 547 $(2M-H)^-$, 273 $(M-H)^-$, 127 $(B)^-$.

Example 12

Preparation of 1-(4-C-methyl-β-D-ribofuranosyl)cytosine, hydrochloric form (12)

Compound 11 (890 mg, 1.93 mmol) was treated with methanolic ammonia (previously saturated at −10° C.), (12 mL) at 100° C. in a stainless-steel bomb for 3 hours, then cooled to room temperature. The solvent was evaporated under reduced pressure and the residue was partitioned between methylene chloride (40 mL) and water (40 mL). The aqueous layer was washed with methylene chloride (2×40 mL), concentrated under reduced pressure. The crude material was purified by silica gel column chromatography [eluent: methylene chloride/methanol/ammonium hydroxide 65:30:5]. The collected fractions were evaporated under reduced pressure and in absolute ethanol (6.3 mL). To the solution was added a 2N hydrochloric acid solution (1.5 mL) and the mixture was stirred before being concentrated under reduced pressure. The procedure was repeated twice and 12 was precipitated from absolute ethanol. Mp: 213–214 (dec.); UV (methanol): $\lambda_{max}$=280 nm ($\epsilon$=9800), $\lambda_{min}$=245 nm ($\epsilon$=3600); $^1$H-NMR (DMSO-$d_6$): δ 9.82 (s, 1H, $NH_2$), 8.72 (s, 1H, $NH_2$), 8.34 (d, 1H, H-6, $J_{6-5}$=7.8 Hz), 6.21 (d, 1H, H-5, $J_{5-6}$=7.8 Hz), 5.83 (d, 1H, H-1', $J_{1'-2'}$=5.8 Hz), 4.22 (d, 1H, OH-2', $J_{OH-2'}$=6.5 Hz), 5.6–4.7 (m, 3H, OH-2', OH-3' and OH-5'), 4.28 (t, 1H, H-2', J=5.6 Hz), 3.99 (d, 1H, H-3', J=5.3 Hz), 3.43 (m, 2H, H-5' and H-5''), 1.14 (s, 3H, $CH_3$); MS (matrix GT): FAB>0 m/z 515 $(2M+H)^+$, 258 $(M+H)^+$, 147 $(S)^+$, 112 $(BH_2)^+$ FAB<0 m/z 256 $(M-H)^-$.

Example 13

Preparation of 1-(5-O-Benzoyl-4-C-methyl-2,3-O-acetyl-β-D-ribofuranosyl)thymine (13)

A suspension of thymine (384 mg, 3.04 mmol) was treated with hexamethyldisilazane (HMDS, 17 mL) and a catalytic amount of ammonium sulfate overnight under reflux. After cooling to room temperature, the mixture was evaporated under reduced pressure, and the residue, obtained as a colorless oil, was diluted with anhydrous 1,2-dichloroethane (6 mL). To the resulting solution was added 7 (1.0 g, 2.53 mmol) in anhydrous 1,2-dichloroethane (14 mL), followed by addition of trimethylsilyl trifluoromethanesulfonate (TMSTf, 0.98 mL, 5.06 mmol). The solution was stirred for 5 hours at room temperature under argon atmosphere, then diluted with chloroform (150 mL), washed with the same volume of a saturated aqueous sodium hydrogen carbonate solution and finally with water (2×100 mL). The organic phase was dried over sodium sulfate, then evaporated under reduced pressure. The resulting crude material was purified by silica gel column chromatography [eluent: 2% of methanol in chloroform] to afford pure 13 (1.09 g, 94%) as a foam. $^1$H-NMR (DMSO-$d_6$): δ 11.47 (s, 1H, NH), 8.1–7.4 (m, 6H, $C_6H_5CO$ and H-6), 5.98 (d, 1H, H-1', J=5.0 Hz), 5.5–5.7 (m, 2H, H-2' and H-3'), 4.42 (dd, 2H, H-5' and H-5'', J=11.6 Hz, J=31.6 Hz), 2.12 (s, 3H, $CH_3CO_2$), 2.09 (s, 3H, $CH_3CO_2$), 1.60 (s, 1H, $CH_3$), 1.37 (s, 3H, $CH_3$); MS (matrix GT): FAB>0 m/z 461 $(M+H)^+$, 335 $(S)^+$, 105 $(C_6H_5CO)^+$, 43 $(CH_3CO)^+$ FAB<0 m/z 459 $(M-H)^-$, 125 $(B)^-$, 121 $(C_6H_5CO_2)^-$, 59 $(CH_3CO_2)^-$.

Example 14

Preparation of 1-(4-C-methyl-β-D-ribofuranosyl)thymine (14)

The title compound can be prepared according to a published procedure from 13 (Waga, T.; Nishizaki, T.; Miyakawa, I.; Orhui, H.; Meguro, H. "Synthesis of 4'-C-methylnucleosides" *Biosci. Biotechnol. Biochem.* 1993, 57, 1433–1438).

A solution of 13 (1.09 g, 2.37 mmol) in methanolic ammonia (previously saturated at −10° C.) (60 mL) was stirred at room temperature overnight. The solvent was evaporated under reduced pressure and the residue was partitioned between methylene chloride (60 mL) and water (60 mL). The aqueous layer was washed with methylene chloride (2×60 mL), concentrated under reduced pressure and coevaporated several times with absolute ethanol. Recrystallization from methanol gave 14 (450 mg, 70%) as a colorless and crystalline solid. Mp: 258–260 (dec.) (lit. 264: Ref.6); UV ($H_2O$): $\lambda_{max}$=264.4 nm ($\epsilon$=8800), $\lambda_{min}$=232.0 nm ($\epsilon$=2200); $^1$H-NMR (DMSO-$d_6$): δ 11.29 (s, 1H, NH), 7.75 (s, 1H, H-6), 5.82 (d, 1H, H-1', $J_{1'-2'}$=7.2 Hz), 5.19 (m, 2H, OH-2', OH-5'), 5.02 (d, 1H, OH-3', $J_{OH-3'}$=5.0 Hz), 4.21 (dd, 1H, H-2', J=6.4 Hz, J=12.3 Hz), 3.92 (t, 1H, H-3', $J_{3'-2'}$=$J_{3'-OH'}$=5.0 Hz), 3.30 (m, 2H, H-5' and H-5''), 1.78 (s, 3H, $CH_3$), 1.09 (s, 3H, $CH_3$); MS (matrix GT): FAB>0 m/z 545 $(2M+H)^+$, 365 $(M+G+H)^+$, 273 $(M+H)^+$, 147 $(S)^+$, 127 $(B+2H)^+$, FAB<0 m/z 543 $(2M-H)^-$, 271 $(M-H)^-$, 125 $(B)^-$, $[\alpha]_D^{20}$ −32.0 (c=0.5 in $H_2O$, litt. −26.4).

Example 15

Preparation of 1-(5,2,3-Tri-O-acetyl-4-C-methyl-β-D-ribofuranosyl)thymine (15)

A solution of 14 (200 mg, 0.735 mmol) in anhydrous pyridine (7.4 ml) was treated with acetic anhydride (1.2 mL) and stirred at room temperature for 3 hours. The solvent was evaporated under reduced pressure, and the residue was purified by silica gel column chromatography [eluent: stepwise gradient of methanol (0–5%) in methylene chloride] to afford pure 15 (0.400 g, quantitative yield) as a foam. $^1$H-NMR (DMSO-$d_6$): δ 11.45 (s, 1H, NH), 7.56 (s, 1H, H-6), 5.90 (d, 1H, H-1', $J_{1'-2'}$=4.8 Hz), 5.5–5.4 (m, 2H, H-2' and H-3'), 4.3–4.0 (m, 2H, H-5' and H-5"), 2.1–2.0 (m, 9H, 3 $CH_3CO_2$), 1.78 (s, 1H, $CH_3$), 1.20 (s, 3H, $CH_3$); MS (matrix GT): FAB>0 m/z 797 (2M+H)$^+$, 399 (M+H)$^+$, 339 (M−$CH_3CO_2$)$^+$, 273 (S)$^+$, 127 ($BH_2$)$^+$, 43 ($CH_3CO$)$^+$ FAB<0 m/z 795 (2M−H)$^-$, 397 (M−H)$^-$, 355 (M−$CH_3CO$)$^-$, 125 (B)$^-$, 59 ($CH_3CO_2$)$^-$.

Example 16

Preparation of 1-(5,2,3-Tri-O-acetyl-4-C-methyl-β-D-ribofuranosyl)-4-thio-thymine (16)

Lawesson's reagent (119 mg, 0.29 mmol) was added under argon to a solution of 15 (0.167 g, 4.19 mmol) in anhydrous 1,2-dichloroethane (11 mL) and the reaction mixture was stirred overnight under reflux. The solvent was evaporated under reduced pressure and the residue was purified by silica gel column chromatography [eluent: stepwise gradient of methanol (1–2%) in chloroform] to give pure 16 (0.165 g, 95%) as a yellow foam. $^1$H-NMR (DMSO-$d_6$): δ 12.81 (s, 1H, NH), 7.64 (s, 1H, H-6), 5.84 (d, 1H, H-1', $J_{1'-2'}$=4.66 Hz), 5.5–5.4 (m, 2H, H-2' and H-3'), 4.11 (dd, 2H, H-5' and H-5", J=11.7 Hz, J=31.3 Hz), 2.0–1.8 (m, 12H, 3 $CH_3CO_2$ and $CH_3$), 1.33 (s, 3H, $CH_3$); MS (matrix GT): FAB>0 m/z 829 (2M+H)$^+$, 415 (M+H)$^+$, 273 (S)$^+$, 143 ($BH_2$)$^+$, 43 ($CH_3CO$)$^+$ FAB<0 m/z 827 (2M−H)$^-$, 413 (M−H)$^-$, 141 (B)$^{31}$, 59 ($CH_3CO_2$)$^-$.

In a similar manner, the following nucleosides of Formula II are prepared, using the appropriate sugar and pyrimidine bases.

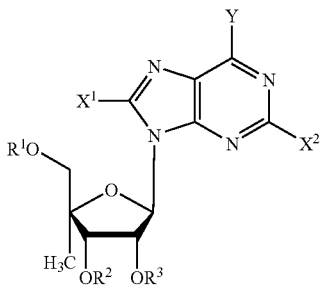

(II)

wherein:

| $R^1$ | $R^2$ | $R^3$ | $X^1$ | Y |
|---|---|---|---|---|
| H | H | H | H | H |
| H | H | H | H | $NH_2$ |
| H | H | H | H | NH-cyclopropyl |
| H | H | H | H | NH-methyl |
| H | H | H | H | NH-ethyl |
| H | H | H | H | NH-acetyl |
| H | H | H | H | OH |
| H | H | H | H | OMe |
| H | H | H | H | OEt |
| H | H | H | H | O-cyclopropyl |
| H | H | H | H | O-acetyl |
| H | H | H | H | SH |
| H | H | H | H | SMe |
| H | H | H | H | SEt |
| H | H | H | H | S-cyclopropyl |
| monophosphate | H | H | H | $NH_2$ |
| monophosphate | H | H | H | NH-acetyl |
| monophosphate | H | H | H | NH-cyclopropyl |
| monophosphate | H | H | H | NH-methyl |
| monophosphate | H | H | H | NH-ethyl |
| monophosphate | H | H | H | OH |
| monophosphate | H | H | H | O-acetyl |
| monophosphate | H | H | H | OMe |
| monophosphate | H | H | H | OEt |
| monophosphate | H | H | H | O-cyclopropyl |
| monophosphate | H | H | H | SH |
| monophosphate | H | H | H | SMe |
| monophosphate | H | H | H | SEt |
| monophosphate | H | H | H | S-cyclopropyl |
| diphosphate | H | H | H | $NH_2$ |
| diphosphate | H | H | H | NH-acetyl |

-continued

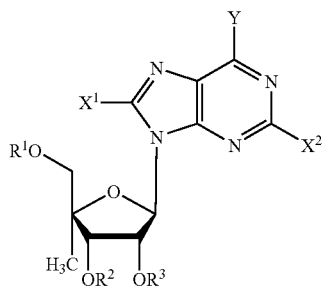
(II)

wherein:

| R¹ | R² | R³ | X¹ | Y |
|---|---|---|---|---|
| diphosphate | H | H | H | NH-cyclopropyl |
| diphosphate | H | H | H | NH-methyl |
| diphosphate | H | H | H | NH-ethyl |
| diphosphate | H | H | H | OH |
| diphosphate | H | H | H | O-acetyl |
| diphosphate | H | H | H | OMe |
| diphosphate | H | H | H | OEt |
| diphosphate | H | H | H | O-cyclopropyl |
| diphosphate | H | H | H | SH |
| diphosphate | H | H | H | SMe |
| diphosphate | H | H | H | SEt |
| diphosphate | H | H | H | S-cyclopropyl |
| triphosphate | H | H | H | $NH_2$ |
| triphosphate | H | H | H | NH-acetyl |
| triphosphate | H | H | H | NH-cyclopropyl |
| triphosphate | H | H | H | NH-methyl |
| triphosphate | H | H | H | NH-ethyl |
| triphosphate | H | H | H | OH |
| triphosphate | H | H | H | OMe |
| triphosphate | H | H | H | OEt |
| triphosphate | H | H | H | O-cyclopropyl |
| triphosphate | H | H | H | O-acetyl |
| triphosphate | H | H | H | SH |
| triphosphate | H | H | H | SMe |
| triphosphate | H | H | H | SEt |
| triphosphate | H | H | H | S-cyclopropyl |
| monophosphate | monophosphate | monophosphate | H | $NH_2$ |
| monophosphate | monophosphate | monophosphate | H | NH-cyclopropyl |
| monophosphate | monophosphate | monophosphate | H | OH |
| diphosphate | diphosphate | diphosphate | H | $NH_2$ |
| diphosphate | diphosphate | diphosphate | H | NH-cyclopropyl |
| diphosphate | diphosphate | diphosphate | H | OH |
| triphosphate | triphosphate | triphosphate | H | $NH_2$ |
| triphosphate | triphosphate | triphosphate | H | NH-cyclopropyl |
| triphosphate | triphosphate | triphosphate | H | OH |
| H | H | H | F | $NH_2$ |
| H | H | H | F | NH-cyclopropyl |
| H | H | H | F | OH |
| H | H | H | Cl | $NH_2$ |
| H | H | H | Cl | NH-cyclopropyl |
| H | H | H | Cl | OH |
| H | H | H | Br | $NH_2$ |
| H | H | H | Br | NH-cyclopropyl |
| H | H | H | Br | OH |
| H | H | H | $NH_2$ | $NH_2$ |
| H | H | H | $NH_2$ | NH-cyclopropyl |
| H | H | H | $NH_2$ | OH |
| H | H | H | SH | $NH_2$ |
| H | H | H | SH | NH-cyclopropyl |
| H | H | H | SH | OH |
| acetyl | H | H | H | $NH_2$ |
| acetyl | H | H | H | NH-cyclopropyL |
| acetyl | H | H | H | OH |
| acetyl | H | H | F | $NH_2$ |
| acetyl | H | H | F | NH-cyclopropyl |
| acetyl | H | H | F | OH |
| H | acetyl | acetyl | H | $NH_2$ |
| H | acetyl | acetyl | H | NH-cyclopropyl |
| H | acetyl | acetyl | H | OH |
| acetyl | acetyl | acetyl | H | $NH_2$ |

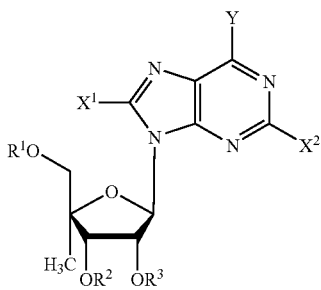

(II)

wherein:

| R¹ | R² | R³ | X¹ | Y |
|---|---|---|---|---|
| acetyl | acetyl | acetyl | H | NH-cyclopropyl |
| acetyl | acetyl | acetyl | H | OH |
| monophosphate | acetyl | acetyl | H | NH$_2$ |
| monophosphate | acetyl | acetyl | H | NH-cyclopropyl |
| monophosphate | acetyl | acetyl | H | OH |
| diphosphate | acetyl | acetyl | H | NH$_2$ |
| diphosphate | acetyl | acetyl | H | NH-cyclopropyl |
| diphosphate | acetyl | acetyl | H | OH |
| triphosphate | acetyl | acetyl | H | NH$_2$ |
| triphosphate | acetyl | acetyl | H | NH-cyclopropyl |
| triphosphate | acetyl | acetyl | H | OH |

Example 17

Preparation of 1-(4-C-methyl-β-D-ribofuranosyl)-5-methyl-cytosine (17), hydrochloride form Compound 16 (0.160 g, 0.386 mmol) was treated with methanolic ammonia (previously saturated at −10° C.), (10 mL) at 100° C. in a stainless-steel bomb for 3 hours, then cooled to room temperature. The solvent was evaporated under reduced pressure and the residue was partitioned between methylene chloride (30 mL) and water (30 mL). The aqueous layer was washed with methylene chloride (2×30 mL), concentrated under reduced pressure. The crude material was purified by silica gel column chromatography [eluent: 20% methanol in methylene chloride] to afford 1-(4-C-methyl-β-D-ribofuranosyl)-5-methyl-cytosine (60 mg, 57%). This compound was dissolved in EtOH 100 (1.5 mL), treated with a 2N hydrochloric acid solution (0.3 mL), and the mixture was stirred before being concentrated under reduced pressure. The procedure was repeated twice and 17 was precipitated from absolute ethanol. Mp: 194–200 (dec.); UV (H$_2$O): $\lambda_{max}$=275.6 nm ($\epsilon$=7300), $\lambda_{min}$=255 nm ($\epsilon$=4700); HPLC 100%, $^1$H-NMR (DMSO-d$_6$): δ 9.34 and 9.10 (2s, 2H, NH$_2$), 8.21 (s, 1H, H-6), 5.80 (d, 1H, H-1', J$_{1'-2'}$=6.0 Hz), 5.3–4.3 (m, 3H, OH-2', OH-3' and OH-5'), 4.21 (t, 1H, H-2', J=5.7 Hz), 3.98 (d, 1H, H-3', J=5.3 Hz), 3.5–3.3 (m, 2H, H-5' and H-5"), 1.97 (s, 3H, CH$_3$), 1.12 (s, 3H, CH$_3$).

Example 18

Preparation of O-6-Diphenylcarbamoyl-N$^2$-isobutyryl-9-(2,3-di-O-acetyl-5-O-benzoyl-4-C-methyl-β-D-ribofuranosyl)guanine (18)

To a suspension of O-6-diphenylcarbamoyl-N$^2$-isobutyrylguanine (1.80 g, 4.33 mmol) in anhydrous toluene (20 mL) was added N,O-bis(trimethylsilyl)acetamide (1.92 mL, 7.9 mmol). The reaction mixture was allowed to warm under reflux for 1 hour. Compound 7 (1.55 g, 3.93 mmol) was dissolved in toluene (10 mL) and trimethylsilyltrifluoromethanesulfonate (TMSTF) (915 mL, 4.72 mmol) was added. The mixture was heated under reflux for 30 minutes. The solution was then cooled to room temperature and neutralized with a 5% aqueous sodium hydrogen carbonate solution. The reaction mixture was diluted with ethyl acetate (200 mL). The organic phase was washed with a 5% aqueous sodium hydrogen carbonate solution (150 mL) and with water (2×150 mL). The organic layer was dried over Na$_2$SO$_4$ and evaporated to dryness. The residue was purified by silica gel column chromatography [eluent: stepwise gradient of diethyl ether (70–90%) in petroleum ether] to afford pure 18 (1.62 g, 55%) as a foam.

Example 19

Preparation of 9-(4-C-methyl-β-D-ribofuranosyl) guanine (19)

The title compound can be prepared according to a published procedure from 18 (Waga, T.; Nishizaki, T.; Miyakawa, I.; Orhui, H.; Meguro, H. "Synthesis of 4'-C-methylnucleosides" Biosci. Biotechnol. Biochem. 1993, 57, 1433–1438).

A solution of 18 (1.50 g, mmol) in methanolic ammonia (previously saturated at −10° C.) (20 mL) was stirred at room temperature overnight. The solvent was evaporated under reduced pressure and the residue was partitioned between methylene chloride (60 mL) and water (60 mL). The aqueous layer was washed with methylene chloride (2×60 mL), concentrated under reduced pressure. The residue was purified by an RP18 column chromatography [eluent water/acetonitrile 95/5] to afford pure 19 (380 mg, 60%). Recrystallization from water gave 19 as a crystalline solid. Mp>300 (dec.), UV (H$_2$O): $\lambda_{max}$=252 nm ($\epsilon$=14500), $^1$H-NMR (DMSO-d$_6$): δ 10.64 (s, 1H, NH), 7.95 (s, 1H, H-8), 6.45 (sl, 2H, NH$_2$), 5.68 (d, 1H, H-1', J$_{1'-2'}$=7.45 Hz), 5.31 (d, 1H, OH, OH-2',J$_{OH-2'}$=6.8 Hz), 5.17 (t, 1H, OH, OH-5', J=5.5 Hz), 5.07 (d, 1H, OH-3', J$_{OH-3'}$=4.5 Hz), 4.65 (dd, 1H, H-2', J=7.1 Hz, J=12.2 Hz), 4.00 (t, 1H, H-3', J$_{3'-2'}$=J$_{3'-OH'}$=4.8 Hz), 3.41 (m, 2H, H-5' and H-5"), 1.12 (s, 3H, CH$_3$); MS (matrix GT): FAB>0 m/z 595 (2M+H)$^+$, 390 (M+G+H)$^+$, 298 (M+H)$^+$, 152 (B+2H)$^+$, FAB<0 m/z 593 (2M−H)$^−$, 296 (M−H)$^−$, 150 (B)$^−$.

Example 20

9-(2,3-di-O-acetyl-5-O-benzoyl-4-C-methyl-β-D-ribofuranosyl)adenine (20)

A solution of 7 (1.10 g, 2.79 mmol) in anhydrous acetonitrile (50 ml) was treated with adenine (452.4 mg, 3.35 mmol) and stannic chloride (SnCl$_4$, 660 μL, 5.58 mmol) and stirred at room temperature overnight. The solution was concentrated under reduced pressure, diluted with chloroform (100 mL) and treated with a cold saturated aqueous solution of NaHCO$_3$ (100 ml). The mixture was filtered on celite, and the precipitate was washed with hot chloroform. The filtrates were combined, washed with water (100 ml) and brine (100 ml), dried (Na$_2$SO$_4$), and evaporated under reduced pressure. The residue was purified by silica gel column chromatography [eluent: stepwise gradient of methanol (3–5%) in dichloromethane] to afford pure 20 (977 mg, 77%) as a white foam. $^1$H-NMR (DMSO-d$_6$): δ 8.31–7.49 (m, 7H, C$_6$H$_5$CO, H-2 and H-8), 7.37 (ls, 2H, NH$_2$) 6.27 (m, 2H, H-1' and H-3'), 5.90 (m, 1H, H-2'), 4.60 (d, 1H, H-5', J=11.7 Hz), 4.35 (d, 1H, H-5'), 2.17 (s, 3H, CH$_3$CO$_2$), 2.06 (s, 3H, CH$_3$CO$_2$), 1.42 (s, 3H, CH$_3$).

Example 21

Preparation of 9-(4-C-methyl-β-D-ribofuranosyl)adenine (21)

The title compound can be prepared according to a published procedure from 20 (Waga, T.; Nishizaki, T.; Miyakawa, I.; Orhui, H.; Meguro, H. "Synthesis of 4'-C-methylnucleosides" *Biosci. Biotechnol. Biochem.* 1993, 57, 1433–1438).

A solution of 20 (970 mg, 2.08 mmol) in methanolic ammonia (previously saturated at −10° C.) (50 mL) was stirred at room temperature overnight. The solvent was evaporated under reduced pressure and the residue was partitioned between methylene chloride (100 ml) and water (100 ml). The aqueous layer was washed with methylene chloride (2×100 mL), and concentrated under reduced pressure. The residue was purified by silica gel column chromatography [eluent: stepwise gradient of methanol (10–30%) in ethyl acetate] to afford pure 21 (554 mg, 95%). Crystallization from methanol/ethyl acetate gave 21 as a white solid. Mp: 96–97 (dec.); $^1$H-NMR (DMSO-d$_6$): δ 8.33 (s, 1H, H-2), 8.13 (s, 1H, H-8), 7.36 (brs, 2H, NH2), 5.84 (d, 1H, H-1', J$_{1'-2'}$=7.4 Hz), 5.69 (dd, 1H, OH-5', J=4.2 Hz and J=7.8 Hz), 5.33 (d, 1H, OH-2', J=6.6 Hz), 5.13 (d, 1H, OH-3', J=4.4 Hz), 4.86 (m, 1H, H-2'), 4.04 (t, 1H, H-3'), 3.58–3.32 (m, 2H, H-5' and H-5"), 1.15 (s, 3H, CH$_3$); MS (matrix GT): FAB>0 m/z 563 (2M+H)$^+$, 374 (M+G+H)$^+$, 282 (M+H)$^+$, 136 (B+2H)$^+$, FAB<0 m/z 561 (2M−H)$^−$, 280 (M−H)$^−$, 134 (B)$^−$.

In a similar manner, the following nucleosides of Formula I are prepared, using the appropriate sugar and purine bases.

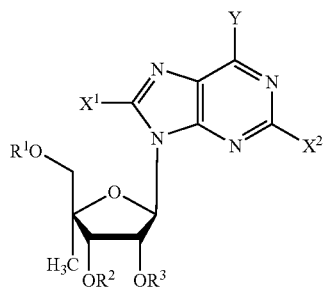

(I)

wherein:

| R | R$^2$ | R$^3$ | X$^1$ | X$^2$ | Y |
|---|---|---|---|---|---|
| H | H | H | H | H | H |
| H | H | H | H | H | NH$_2$ |
| H | H | H | H | H | NH-cyclopropyl |
| H | H | H | H | H | NH-methyl |
| H | H | H | H | H | NH-ethyl |
| H | H | H | H | H | NH-acetyl |
| H | H | H | H | H | OH |
| H | H | H | H | H | OMe |
| H | H | H | H | H | OEt |
| H | H | H | H | H | O-cyclopropyl |
| H | H | H | H | H | O-acetyl |
| H | H | H | H | H | SH |
| H | H | H | H | H | SMe |
| H | H | H | H | H | SEt |
| H | H | H | H | H | S-cyclopropyl |
| H | H | H | H | H | F |
| H | H | H | H | H | Cl |
| H | H | H | H | H | Br |
| H | H | H | H | H | I |

-continued

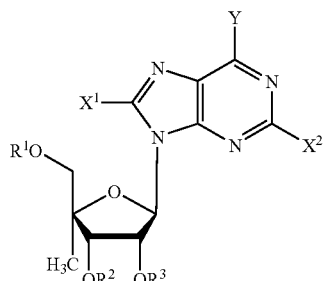

(I)

wherein:

| R | R² | R³ | X¹ | X² | Y |
|---|----|----|----|----|---|
| monophosphate | H | H | H | H | NH₂ |
| monophosphate | H | H | H | H | NH-acetyl |
| monophosphate | H | H | H | H | NH-cyclopropyl |
| monophosphate | H | H | H | H | NH-methyl |
| monophosphate | H | H | H | H | NH-ethyl |
| monophosphate | H | H | H | H | OH |
| monophosphate | H | H | H | H | O-acetyl |
| monophosphate | H | H | H | H | OMe |
| monophosphate | H | H | H | H | OEt |
| monophosphate | H | H | H | H | O-cyclopropyl |
| monophosphate | H | H | H | H | SH |
| monophosphate | H | H | H | H | SMe |
| monophosphate | H | H | H | H | SEt |
| monophosphate | H | H | H | H | S-cyclopropyl |
| monophosphate | H | H | H | H | F |
| monophosphate | H | H | H | H | Cl |
| monophosphate | H | H | H | H | Br |
| monophosphate | H | H | H | H | I |
| diphosphate | H | H | H | H | NH₂ |
| diphosphate | H | H | H | H | NH-acetyl |
| diphosphate | H | H | H | H | NH-cyclopropyl |
| diphosphate | H | H | H | H | NH-methyl |
| diphosphate | H | H | H | H | NH-ethyl |
| diphosphate | H | H | H | H | OH |
| diphosphate | H | H | H | H | O-acetyl |
| diphosphate | H | H | H | H | OMe |
| diphosphate | H | H | H | H | OEt |
| diphosphate | H | H | H | H | O-cyclopropyl |
| diphosphate | H | H | H | H | SH |
| diphosphate | H | H | H | H | SMe |
| diphosphate | H | H | H | H | SEt |
| diphosphate | H | H | H | H | S-cyclopropyl |
| diphosphate | H | H | H | H | F |
| diphosphate | H | H | H | H | Cl |
| diphosphate | H | H | H | H | Br |
| diphosphate | H | H | H | H | I |
| triphosphate | H | H | H | H | NH₂ |
| triphosphate | H | H | H | H | NH-acetyl |
| triphosphate | H | H | H | H | NH-cyclopropyl |
| triphosphate | H | H | H | H | NH-methyl |
| triphosphate | H | H | H | H | NH-ethyl |
| triphosphate | H | H | H | H | OH |
| triphosphate | H | H | H | H | OMe |
| triphosphate | H | H | H | H | OEt |
| triphosphate | H | H | H | H | O-cyclopropyl |
| triphosphate | H | H | H | H | O-acetyl |
| triphosphate | H | H | H | H | SH |
| triphosphate | H | H | H | H | SMe |
| triphosphate | H | H | H | H | SEt |
| triphosphate | H | H | H | H | S-cyclopropyl |
| triphosphate | H | H | H | H | F |
| triphosphate | H | H | H | H | Cl |
| triphosphate | H | H | H | H | Br |
| triphosphate | H | H | H | H | I |
| monophosphate | monophosphate | monophosphate | H | H | NH₂ |
| monophosphate | monophosphate | monophosphate | H | H | NH-cyclopropyl |
| monophosphate | monophosphate | monophosphate | H | H | OH |
| monophosphate | monophosphate | monophosphate | H | H | F |
| monophosphate | monophosphate | monophosphate | H | H | Cl |
| diphosphate | diphosphate | diphosphate | H | H | NH₂ |

-continued

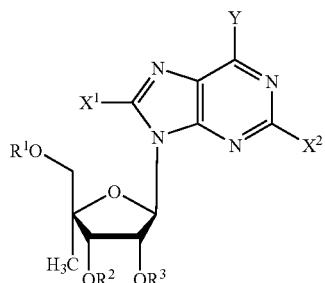

(I)

wherein:

| R | $R^2$ | $R^3$ | $X^1$ | $X^2$ | Y |
|---|---|---|---|---|---|
| diphosphate | diphosphate | diphosphate | H | H | NH-cyclopropyl |
| diphosphate | diphosphate | diphosphate | H | H | OH |
| diphosphate | diphosphate | diphosphate | H | H | F |
| diphosphate | diphosphate | diphosphate | H | H | Cl |
| triphosphate | triphosphate | triphosphate | H | H | $NH_2$ |
| triphosphate | triphosphate | triphosphate | H | H | NH-cyclopropyl |
| triphosphate | triphosphate | triphosphate | H | H | OH |
| triphosphate | triphosphate | triphosphate | H | H | F |
| triphosphate | triphosphate | triphosphate | H | H | Cl |
| H | H | H | F | H | $NH_2$ |
| H | H | H | F | H | NH-cyclopropyl |
| H | H | H | F | H | OH |
| H | H | H | F | H | F |
| H | H | H | F | H | Cl |
| H | H | H | Cl | H | $NH_2$ |
| H | H | H | Cl | H | NH-cyclopropyl |
| H | H | H | Cl | H | OH |
| H | H | H | Cl | H | F |
| H | H | H | Cl | H | Cl |
| H | H | H | Br | H | $NH_2$ |
| H | H | H | Br | H | NH-cyclopropyl |
| H | H | H | Br | H | OH |
| H | H | H | Br | H | F |
| H | H | H | Br | H | Cl |
| H | H | H | $NH_2$ | H | $NH_2$ |
| H | H | H | $NH_2$ | H | NH-cyclopropyl |
| H | H | H | $NH_2$ | H | OH |
| H | H | H | $NH_2$ | H | F |
| H | H | H | $NH_2$ | H | Cl |
| H | H | H | SH | H | $NH_2$ |
| H | H | H | SH | H | NH-cyclopropyl |
| H | H | H | SH | H | OH |
| H | H | H | SH | H | F |
| H | H | H | SH | H | Cl |
| acetyl | H | H | H | H | $NH_2$ |
| acetyl | H | H | H | H | NH-cyclopropyl |
| acetyl | H | H | H | H | OH |
| acetyl | H | H | H | H | F |
| acetyl | H | H | H | H | Cl |
| acetyl | H | H | F | H | $NH_2$ |
| acetyl | H | H | F | H | NH-cyclopropyl |
| acetyl | H | H | F | H | OH |
| acetyl | H | H | F | H | F |
| acetyl | H | H | F | H | Cl |
| H | acetyl | acetyl | H | H | $NH_2$ |
| H | acetyl | acetyl | H | H | NH-cyclopropyl |
| H | acetyl | acetyl | H | H | OH |
| H | acetyl | acetyl | H | H | F |
| H | acetyl | acetyl | H | H | Cl |
| acetyl | acetyl | acetyl | H | H | $NH_2$ |
| acetyl | acetyl | acetyl | H | H | NH-cyclopropyl |
| acetyl | acetyl | acetyl | H | H | OH |
| acetyl | acetyl | acetyl | H | H | F |
| acetyl | acetyl | acetyl | H | H | Cl |
| monophosphate | acetyl | acetyl | H | H | $NH_2$ |
| monophosphate | acetyl | acetyl | H | H | NH-cyclopropyl |
| monophosphate | acetyl | acetyl | H | H | OH |
| monophosphate | acetyl | acetyl | H | H | F |
| monophosphate | acetyl | acetyl | H | H | Cl |
| diphosphate | acetyl | acetyl | H | H | $NH_2$ |

-continued

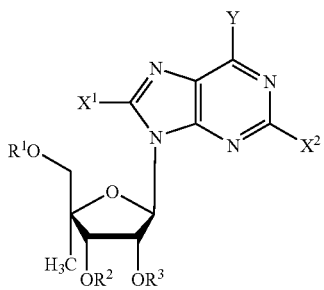
(I)

wherein:

| R | R² | R³ | X¹ | X² | Y |
|---|---|---|---|---|---|
| diphosphate | acetyl | acetyl | H | H | NH-cyclopropyl |
| diphosphate | acetyl | acetyl | H | H | OH |
| diphosphate | acetyl | acetyl | H | H | F |
| diphosphate | acetyl | acetyl | H | H | Cl |
| triphosphate | acetyl | acetyl | H | H | $NH_2$ |
| triphosphate | acetyl | acetyl | H | H | NH-cyclopropyl |
| triphosphate | acetyl | acetyl | H | H | OH |
| triphosphate | acetyl | acetyl | H | H | F |
| triphosphate | acetyl | acetyl | H | H | Cl |
| H | H | H | H | $NH_2$ | H |
| H | H | H | H | $NH_2$ | $NH_2$ |
| H | H | H | H | $NH_2$ | NH-cyclopropyl |
| H | H | H | H | $NH_2$ | NH-methyl |
| H | H | H | H | $NH_2$ | NH-ethyl |
| H | H | H | H | $NH_2$ | NH-acetyl |
| H | H | H | H | $NH_2$ | OH |
| H | H | H | H | $NH_2$ | OMe |
| H | H | H | H | $NH_2$ | OEt |
| H | H | H | H | $NH_2$ | O-cyclopropyl |
| H | H | H | H | $NH_2$ | O-acetyl |
| H | H | H | H | $NH_2$ | SH |
| H | H | H | H | $NH_2$ | SMe |
| H | H | H | H | $NH_2$ | SEt |
| H | H | H | H | $NH_2$ | S-cyclopropyl |
| H | H | H | H | $NH_2$ | F |
| H | H | H | H | $NH_2$ | Cl |
| H | H | H | H | $NH_2$ | Br |
| H | H | H | H | $NH_2$ | I |
| monophosphate | H | H | H | $NH_2$ | $NH_2$ |
| monophosphate | H | H | H | $NH_2$ | NH-acetyl |
| monophosphate | H | H | H | $NH_2$ | NH-cyclopropyl |
| monophosphate | H | H | H | $NH_2$ | NH-methyl |
| monophosphate | H | H | H | $NH_2$ | NH-ethyl |
| monophosphate | H | H | H | $NH_2$ | OH |
| monophosphate | H | H | H | $NH_2$ | O-acetyl |
| monophosphate | H | H | H | $NH_2$ | OMe |
| monophosphate | H | H | H | $NH_2$ | OEt |
| monophosphate | H | H | H | $NH_2$ | O-cyclopropyl |
| monophosphate | H | H | H | $NH_2$ | SH |
| monophosphate | H | H | H | $NH_2$ | SMe |
| monophosphate | H | H | H | $NH_2$ | SEt |
| monophosphate | H | H | H | $NH_2$ | S-cyclopropyl |
| monophosphate | H | H | H | $NH_2$ | F |
| monophosphate | H | H | H | $NH_2$ | Cl |
| monophosphate | H | H | H | $NH_2$ | Br |
| monophosphate | H | H | H | $NH_2$ | I |
| diphosphate | H | H | H | $NH_2$ | $NH_2$ |
| diphosphate | H | H | H | $NH_2$ | NH-acetyl |
| diphosphate | H | H | H | $NH_2$ | NH-cyclopropyl |
| diphosphate | H | H | H | $NH_2$ | NH-methyl |
| diphosphate | H | H | H | $NH_2$ | NH-ethyl |
| diphosphate | H | H | H | $NH_2$ | OH |
| diphosphate | H | H | H | $NH_2$ | O-acetyl |
| diphosphate | H | H | H | $NH_2$ | OMe |
| diphosphate | H | H | H | $NH_2$ | OEt |
| diphosphate | H | H | H | $NH_2$ | O-cyclopropyl |
| diphosphate | H | H | H | $NH_2$ | SH |
| diphosphate | H | H | H | $NH_2$ | SMe |
| diphosphate | H | H | H | $NH_2$ | SEt |
| diphosphate | H | H | H | $NH_2$ | S-cyclopropyl |

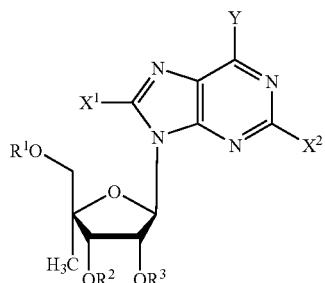

(I)

wherein:

| R | R² | R³ | X¹ | X² | Y |
|---|---|---|---|---|---|
| diphosphate | H | H | H | NH₂ | F |
| diphosphate | H | H | H | NH₂ | Cl |
| diphosphate | H | H | H | NH₂ | Br |
| diphosphate | H | H | H | NH₂ | I |
| triphosphate | H | H | H | NH₂ | NH₂ |
| triphosphate | H | H | H | NH₂ | NH-acetyl |
| triphosphate | H | H | H | NH₂ | NH-cyclopropyl |
| tnphosphate | H | H | H | NH₂ | NH-methyl |
| triphosphate | H | H | H | NH₂ | NH-ethyl |
| triphosphate | H | H | H | NH₂ | OH |
| triphosphate | H | H | H | NH₂ | OMe |
| triphosphate | H | H | H | NH₂ | OEt |
| triphosphate | H | H | H | NH₂ | O-cyclopropyl |
| triphosphate | H | H | H | NH₂ | O-acetyl |
| triphosphate | H | H | H | NH₂ | SH |
| triphosphate | H | H | H | NH₂ | SMe |
| triphosphate | H | H | H | NH₂ | SEt |
| triphosphate | H | H | H | NH₂ | S-cyclopropyl |
| triphosphate | H | H | H | NH₂ | F |
| triphosphate | H | H | H | NH₂ | Cl |
| triphosphate | H | H | H | NH₂ | Br |
| triphosphate | H | H | H | NH₂ | I |
| monophosphate | monophosphate | monophosphate | H | NH₂ | NH₂ |
| monophosphate | monophosphate | monophosphate | H | NH₂ | NH-cyclopropyl |
| monophosphate | monophosphate | monophosphate | H | NH₂ | OH |
| monophosphate | monophosphate | monophosphate | H | NH₂ | F |
| monophosphate | monophosphate | monophosphate | H | NH₂ | Cl |
| diphosphate | diphosphate | diphosphate | H | NH₂ | NH₂ |
| diphosphate | diphosphate | diphosphate | H | NH₂ | NH-cyclopropyl |
| diphosphate | diphosphate | diphosphate | H | NH₂ | OH |
| diphosphate | diphosphate | diphosphate | H | NH₂ | F |
| diphosphate | diphosphate | diphosphate | H | NH₂ | Cl |
| triphosphate | triphosphate | triphosphate | H | NH₂ | NH₂ |
| triphosphate | triphosphate | triphosphate | H | NH₂ | NH-cyclopropyl |
| triphosphate | triphosphate | triphosphate | H | NH₂ | OH |
| triphosphate | triphosphate | triphosphate | H | NH₂ | F |
| triphosphate | triphosphate | triphosphate | H | NH₂ | Cl |
| H | H | H | F | NH₂ | NH₂ |
| H | H | H | F | NH₂ | NH-cyclopropyl |
| H | H | H | F | NH₂ | OH |
| H | H | H | F | NH₂ | F |
| H | H | H | F | NH₂ | Cl |
| H | H | H | Cl | NH₂ | NH₂ |
| H | H | H | Cl | NH₂ | NH-cyclopropyl |
| H | H | H | Cl | NH₂ | OH |
| H | H | H | Cl | NH₂ | F |
| H | H | H | Cl | NH₂ | Cl |
| H | H | H | Br | NH₂ | NH₂ |
| H | H | H | Br | NH₂ | NH-cyclopropyl |
| H | H | H | Br | NH₂ | OH |
| H | H | H | Br | NH₂ | F |
| H | H | H | Br | NH₂ | Cl |
| H | H | H | NH₂ | NH₂ | NH₂ |
| H | H | H | NH₂ | NH₂ | NH-cyclopropyl |
| H | H | H | NH₂ | NH₂ | OH |
| H | H | H | NH₂ | NH₂ | F |
| H | H | H | NH₂ | NH₂ | Cl |
| H | H | H | SH | NH₂ | NH₂ |
| H | H | H | SH | NH₂ | NH-cyclopropyl |
| H | H | H | SH | NH₂ | OH |

-continued

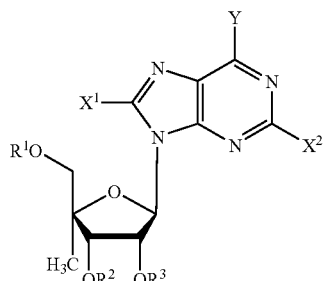

(I)

wherein:

| R | R² | R³ | X¹ | X² | Y |
|---|---|---|---|---|---|
| H | H | H | SH | NH₂ | F |
| H | H | H | SH | NH₂ | Cl |
| acetyl | H | H | H | NH₂ | NH₂ |
| acetyl | H | H | H | NH₂ | NH-cyclopropyl |
| acetyl | H | H | H | NH₂ | OH |
| acetyl | H | H | H | NH₂ | F |
| acetyl | H | H | H | NH₂ | Cl |
| acetyl | H | H | F | NH₂ | NH₂ |
| acetyl | H | H | F | NH₂ | NH-cyclopropyl |
| acetyl | H | H | F | NH₂ | OH |
| acetyl | H | H | F | NH₂ | F |
| acetyl | H | H | F | NH₂ | Cl |
| H | acetyl | acetyl | H | NH₂ | NH₂ |
| H | acetyl | acetyl | H | NH₂ | NH-cyclopropyl |
| H | acetyl | acetyl | H | NH₂ | OH |
| H | acetyl | acetyl | H | NH₂ | F |
| H | acetyl | acetyl | H | NH₂ | Cl |
| acetyl | acetyl | acetyl | H | NH₂ | NH₂ |
| acetyl | acetyl | acetyl | H | NH₂ | NH-cyclopropyl |
| acetyl | acetyl | acetyl | H | NH₂ | OH |
| acetyl | acetyl | acetyl | H | NH₂ | F |
| acetyl | acetyl | acetyl | H | NH₂ | Cl |
| monophosphate | acetyl | acetyl | H | NH₂ | NH₂ |
| monophosphate | acetyl | acetyl | H | NH₂ | NH-cyclopropyl |
| monophosphate | acetyl | acetyl | H | NH₂ | OH |
| monophosphate | acetyl | acetyl | H | NH₂ | F |
| monophosphate | acetyl | acetyl | H | NH₂ | Cl |
| diphosphate | acetyl | acetyl | H | NH₂ | NH₂ |
| diphosphate | acetyl | acetyl | H | NH₂ | NH-cyclopropyl |
| diphosphate | acetyl | acetyl | H | NH₂ | OH |
| diphosphate | acetyl | acetyl | H | NH₂ | F |
| diphosphate | acetyl | acetyl | H | NH₂ | Cl |
| triphosphate | acetyl | acetyl | H | NH₂ | NH₂ |
| triphosphate | acetyl | acetyl | H | NH₂ | NH-cyclopropyl |
| triphosphate | acetyl | acetyl | H | NH₂ | OH |
| triphosphate | acetyl | acetyl | H | NH₂ | F |
| triphosphate | acetyl | acetyl | H | NH₂ | Cl |
| H | H | H | H | Cl | H |
| H | H | H | H | Cl | H |
| H | H | H | H | Cl | NH₂ |
| H | H | H | H | Cl | NH-cyclopropyl |
| H | H | H | H | Cl | NH-methyl |
| H | H | H | H | Cl | NH-ethyl |
| H | H | H | H | Cl | NH-acetyl |
| H | H | H | H | Cl | OH |
| H | H | H | H | Cl | OMe |
| H | H | H | H | Cl | OEt |
| H | H | H | H | Cl | O-cyclopropyl |
| H | H | H | H | Cl | O-acetyl |
| H | H | H | H | Cl | SH |
| H | H | H | H | Cl | SMe |
| H | H | H | H | Cl | SEt |
| H | H | H | H | Cl | S-cyclopropyl |
| monophosphate | H | H | H | Cl | NH₂ |
| monophosphate | H | H | H | Cl | NH-acetyl |
| monophosphate | H | H | H | Cl | NH-cyclopropyl |
| monophosphate | H | H | H | Cl | NH-methyl |
| monophosphate | H | H | H | Cl | NH-ethyl |
| monophosphate | H | H | H | Cl | OH |
| monophosphate | H | H | H | Cl | O-acetyl |

-continued

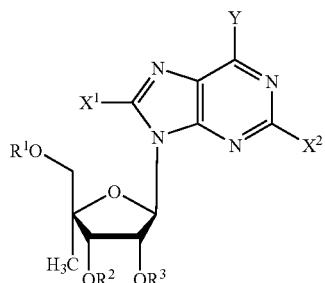

(I)

wherein:

| R | $R^2$ | $R^3$ | $X^1$ | $X^2$ | Y |
|---|---|---|---|---|---|
| monophosphate | H | H | H | Cl | OMe |
| monophosphate | H | H | H | Cl | OEt |
| monophosphate | H | H | H | Cl | O-cyclopropyl |
| monophosphate | H | H | H | Cl | SH |
| monophosphate | H | H | H | Cl | SMe |
| monophosphate | H | H | H | Cl | SEt |
| monophosphate | H | H | H | Cl | S-cyclopropyl |
| diphosphate | H | H | H | Cl | $NH_2$ |
| diphosphate | H | H | H | Cl | NH-acetyl |
| diphosphate | H | H | H | Cl | NH-cyclopropyl |
| diphosphate | H | H | H | Cl | NH-methyl |
| diphosphate | H | H | H | Cl | NH-ethyl |
| diphosphate | H | H | H | Cl | OH |
| diphosphate | H | H | H | Cl | O-acetyl |
| diphosphate | H | H | H | Cl | OMe |
| diphosphate | H | H | H | Cl | OEt |
| diphosphate | H | H | H | Cl | O-cyclopropyl |
| diphosphate | H | H | H | Cl | SH |
| diphosphate | H | H | H | Cl | SMe |
| diphosphate | H | H | H | Cl | SEt |
| diphosphate | H | H | H | Cl | S-cyclopropyl |
| triphosphate | H | H | H | Cl | $NH_2$ |
| triphosphate | H | H | H | Cl | NH-acetyl |
| triphosphate | H | H | H | Cl | NH-cyclopropyl |
| triphosphate | H | H | H | Cl | NH-methyl |
| triphosphate | H | H | H | Cl | NH-ethyl |
| triphosphate | H | H | H | Cl | OH |
| triphosphate | H | H | H | Cl | OMe |
| triphosphate | H | H | H | Cl | OEt |
| triphosphate | H | H | H | Cl | O-cyclopropyl |
| triphosphate | H | H | H | Cl | O-acetyl |
| triphosphate | H | H | H | Cl | SH |
| triphosphate | H | H | H | Cl | SMe |
| triphosphate | H | H | H | Cl | SEt |
| triphosphate | H | H | H | Cl | S-cyclopropyl |
| monophosphate | monophosphate | monophosphate | H | Cl | $NH_2$ |
| monophosphate | monophosphate | monophosphate | H | Cl | NH-cyclopropyl |
| monophosphate | monophosphate | monophosphate | H | Cl | OH |
| diphosphate | diphosphate | diphosphate | H | Cl | $NH_2$ |
| diphosphate | diphosphate | diphosphate | H | Cl | NH-cyclopropyl |
| diphosphate | diphosphate | diphosphate | H | Cl | OH |
| triphosphate | triphosphate | triphosphate | H | Cl | $NH_2$ |
| triphosphate | triphosphate | triphosphate | H | Cl | NH-cyclopropyl |
| triphosphate | triphosphate | triphosphate | H | Cl | OH |
| H | H | H | F | Cl | $NH_2$ |
| H | H | H | F | Cl | NH-cyclopropyl |
| H | H | H | F | Cl | OH |
| H | H | H | Cl | Cl | $NH_2$ |
| H | H | H | Cl | Cl | NH-cyclopropyl |
| H | H | H | Cl | Cl | OH |
| H | H | H | Br | Cl | $NH_2$ |
| H | H | H | Br | Cl | NH-cyclopropyl |
| H | H | H | Br | Cl | OH |
| H | H | H | $NH_2$ | Cl | $NH_2$ |
| H | H | H | $NH_2$ | Cl | NH-cyclopropyl |
| H | H | H | $NH_2$ | Cl | OH |
| H | H | H | SH | Cl | $NH_2$ |
| H | H | H | SH | Cl | NH-cyclopropyl |
| H | H | H | SH | Cl | OH |
| acetyl | H | H | H | Cl | $NH_2$ |

-continued

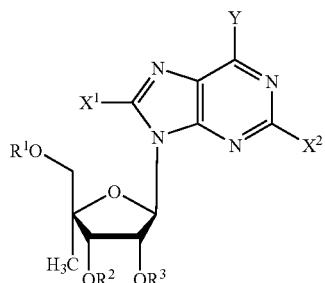

(I)

wherein:

| R | R² | R³ | X¹ | X² | Y |
|---|---|---|---|---|---|
| acetyl | H | H | H | Cl | NH-cyclopropyl |
| acetyl | H | H | H | Cl | OH |
| acetyl | H | H | F | Cl | NH₂ |
| acetyl | H | H | F | Cl | NH-cyclopropyl |
| acetyl | H | H | F | Cl | OH |
| H | acetyl | acetyl | H | Cl | NH₂ |
| H | acetyl | acetyl | H | Cl | NH-cyclopropyl |
| H | acetyl | acetyl | H | Cl | OH |
| acetyl | acetyl | acetyl | H | Cl | NH₂ |
| acetyl | acetyl | acetyl | H | Cl | NH-cyclopropyl |
| acetyl | acetyl | acetyl | H | Cl | OH |
| monophosphate | acetyl | acetyl | H | Cl | NH₂ |
| monophosphate | acetyl | acetyl | H | Cl | NH-cyclopropyl |
| monophosphate | acetyl | acetyl | H | Cl | OH |
| diphosphate | acetyl | acetyl | H | Cl | NH₂ |
| diphosphate | acetyl | acetyl | H | Cl | NH-cyclopropyl |
| diphosphate | acetyl | acetyl | H | Cl | OH |
| triphosphate | acetyl | acetyl | H | Cl | NH₂ |
| triphosphate | acetyl | acetyl | H | Cl | NH-cyclopropyl |
| triphosphate | acetyl | acetyl | H | Cl | OH |
| H | H | H | H | Cl | NH₂ |
| H | H | H | H | Cl | NH-cyclopropyl |
| H | H | H | H | Cl | OH |
| H | H | H | H | Br | NH₂ |
| H | H | H | H | Br | NH-cyclopropyl |
| H | H | H | H | Br | OH |

40

Alternatively, the following nucleosides of Formula III are prepared, using the appropriate sugar and pyrimidine or purine bases.

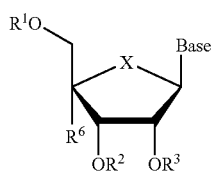

(III)

wherein:

| R¹ | R² | R³ | R⁶ | X | Base |
|---|---|---|---|---|---|
| H | H | H | CH₃ | O | 2,4-O-Diacetyluracil |
| H | H | H | CH₃ | O | Hypoxanthine |
| H | H | H | CH₃ | O | 2,4-O-Diacetylthymine |
| H | H | H | CH₃ | O | Thymine |
| H | H | H | CH₃ | O | Cytosine |
| H | H | H | CH₃ | O | 4-(N-mono-acetyl)cytosine |
| H | H | H | CH₃ | O | 4-(N,N-diacetyl)cytosine |

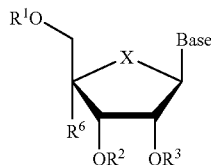

(III)

wherein:

| R¹ | R² | R³ | R⁶ | X | Base |
|---|---|---|---|---|---|
| H | H | H | CH₃ | O | Uracil |
| H | H | H | CH₃ | O | 5-Fluorouracil |
| H | H | H | CH₃ | S | 2,4-O-Diacetyluraci |
| H | H | H | CH₃ | S | Hypoxanthine |
| H | H | H | CH₃ | S | 2,4-O-Diacetylthymine |
| H | H | H | CH₃ | S | Thymine |
| H | H | H | CH₃ | S | Cytosine |
| H | H | H | CH₃ | S | 4-(N-mono-acetyl)cytosine |
| H | H | H | CH₃ | S | 4-(N,N-diacetyl)cytosine |
| H | H | H | CH₃ | S | Uracil |
| H | H | H | CH₃ | S | 5-Fluorouracil |
| monophosphate | H | H | CH₃ | O | 2,4-O-Diacetyluracil |
| monophosphate | H | H | CH₃ | O | Hypoxanthine |
| monophosphate | H | H | CH₃ | O | 2,4-O-Diacetylthym |
| monophosphate | H | H | CH₃ | O | Thymine |
| monophosphate | H | H | CH₃ | O | Cytosine |
| monophosphate | H | H | CH₃ | O | 4-(N-mono-acetyl)cytosine |
| monophosphate | H | H | CH₃ | O | 4-(N,N-diacetyl)cytosine |
| monophosphate | H | H | CH₃ | O | Uracil |
| monophosphate | H | H | CH₃ | O | 5-Fluorouracil |
| monophosphate | H | H | CH₃ | S | 2,4-O-Diacetyluracil |
| monophosphate | H | H | CH₃ | S | Hypoxanthine |
| monophosphate | H | H | CH₃ | S | 2,4-O-Diacetylthym |
| monophosphate | H | H | CH₃ | S | Thymine |
| monophosphate | H | H | CH₃ | S | Cytosine |
| monophosphate | H | H | CH₃ | S | 4-(N-mono-acetyl)cytosine |
| monophosphate | H | H | CH₃ | S | 4-(N,N-diacetyl)cytosine |
| monophosphate | H | H | CH₃ | S | Uracil |
| monophosphate | H | H | CH₃ | S | 5-Fluorouracil |
| diphosphate | H | H | CH₃ | O | 2,4-O-Diacetyluracil |
| diphosphate | H | H | CH₃ | O | Hypoxanthine |
| diphosphate | H | H | CH₃ | O | 2,4-O-Diacetylthymine |
| diphosphate | H | H | CH₃ | O | Thymine |
| diphosphate | H | H | CH₃ | O | Cytosine |
| diphosphate | H | H | CH₃ | O | 4-(N-mono-acetyl)cytosine |
| diphosphate | H | H | CH₃ | O | 4-(N,N-diacetyl)cytosine |
| diphosphate | H | H | CH₃ | O | Uracil |
| diphosphate | H | H | CH₃ | O | 5-Fluorouracil |
| diphosphate | H | H | CH₃ | S | 2,4-O-Diacetyluracil |
| diphosphate | H | H | CH₃ | S | Hypoxanthine |
| diphosphate | H | H | CH₃ | S | 2,4-O-Diacetylthym |
| diphosphate | H | H | CH₃ | S | Thymine |
| diphosphate | H | H | CH₃ | S | Cytosine |
| triphosphate | H | H | CH₃ | O | 2,4-O-Diacetyluracil |
| triphosphate | H | H | CH₃ | O | Hypoxanthine |
| triphosphate | H | H | CH₃ | O | 2,4-O-Diacetylthymine |

-continued

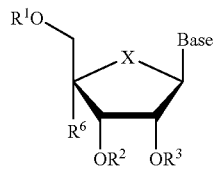

(III)

wherein:

| R¹ | R² | R³ | R⁶ | X | Base |
|---|---|---|---|---|---|
| triphosphate | H | H | CH₃ | O | Thymine |
| triphosphate | H | H | CH₃ | O | Cytosine |
| triphosphate | H | H | CH₃ | O | 4-(N-mono-acetyl)cytosine |
| triphosphate | H | H | CH₃ | O | 4-(N,N-diacetyl)cytosine |
| triphosphate | H | H | CH₃ | O | Uracil |
| triphosphate | H | H | CH₃ | O | 5-Fluorouracil |
| triphosphate | H | H | CH₃ | S | 2,4-O-Diacetyluracil |
| triphosphate | H | H | CH₃ | S | Hypoxanthine |
| triphosphate | H | H | CH₃ | S | 2,4-O-Diacetylthymine |
| triphosphate | H | H | CH₃ | S | Thymine |
| triphosphate | H | H | CH₃ | S | Cytosine |
| monophosphate | monophosphate | monophosphate | CF₃ | O | 2,4-O-Diacetyluracil |
| monophosphate | monophosphate | monophosphate | CF₃ | O | Hypoxanthine |
| monophosphate | monophosphate | monophosphate | CF₃ | O | 2,4-O-Diacetylthymine |
| monophosphate | monophosphate | monophosphate | CF₃ | O | Thymine |
| monophosphate | monophosphate | monophosphate | CF₃ | O | Cytosine |
| monophosphate | monophosphate | monophosphate | CF₃ | O | 4-(N-mono-acetyl)cytosine |
| monophosphate | monophosphate | monophosphate | CF₃ | O | 4-(N,N-diacetyl)cytosine |
| monophosphate | monophosphate | monophosphate | CF₃ | O | Uracil |
| monophosphate | monophosphate | monophosphate | CF₃ | O | 5-Fluorouracil |
| monophosphate | monophosphate | monophosphate | CF₃ | S | 2,4-O-Diacetyluracil |
| monophosphate | monophosphate | monophosphate | CF₃ | S | Hypoxanthine |
| monophosphate | monophosphate | monophosphate | CF₃ | S | 2,4-O-Diacetylthymine |
| monophosphate | monophosphate | monophosphate | CF₃ | S | Thymine |
| monophosphate | monophosphate | monophosphate | CF₃ | S | Cytosine |
| monophosphate | monophosphate | monophosphate | CF₃ | S | 4-(N-mono-acetyl)cytosine |
| monophosphate | monophosphate | monophosphate | CF₃ | S | 4-(N,N-diacetyl)cytosine |
| monophosphate | monophosphate | monophosphate | CF₃ | S | Uracil |
| monophosphate | monophosphate | monophosphate | CF₃ | S | 5-Fluorouracil |
| acetyl | acetyl | acetyl | CF₃ | O | 4-(N,N-diacetyl)cytosine |
| acetyl | acetyl | acetyl | CF₃ | S | 4-(N,N-diacetyl)cytosine |
| acetyl | acetyl | acetyl | 2-bromo-vinyl | O | 4-(N,N-diacetyl)cytosine |
| acetyl | acetyl | acetyl | 2-bromo-vinyl | S | 4-(N,N-diacetyl)cytosine |
| H | H | H | CH₃ | O | 2-(N,N-diacetyl)-guanine |
| H | H | H | CH₃ | O | 6-O-acetyl guanine |
| H | H | H | CH₃ | O | 8-fluoroguanine |
| H | H | H | CH₃ | O | guanine |
| H | H | H | CH₃ | O | 6-(N,N-diacetyl)-adenine |
| H | H | H | CH₃ | O | 2-fluoroadenine |
| H | H | H | CH₃ | O | 8-fluoroadenine |
| H | H | H | CH₃ | O | 2,8-difluoro-adenine |
| H | H | H | CH₃ | O | adenine |
| H | H | H | CH₃ | S | 2-(N,N-diacetyl)-guanine |
| H | H | H | CH₃ | S | 6-O-acetyl guanine |

-continued

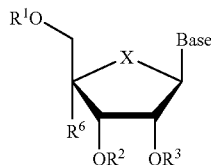
(III)

wherein:

| R¹ | R² | R³ | R⁶ | X | Base |
|---|---|---|---|---|---|
| H | H | H | CH₃ | S | 8-fluoroguanine |
| H | H | H | CH₃ | S | guanine |
| H | H | H | CH₃ | S | 6-(N,N-diacetyl)-adenine |
| H | H | H | CH₃ | S | 2-fluoroadenine |
| H | H | H | CH₃ | S | 8-fluoroadenine |
| H | H | H | CH₃ | S | 2,8-difluoro-adenine |
| H | H | H | CH₃ | S | adenine |
| monophosphate | H | H | CH₃ | O | 2-(N,N-diacetyl)-guanine |
| monophosphate | H | H | CH₃ | O | 6-O-acetyl guanine |
| monophosphate | H | H | CH₃ | O | 8-fluoroguanine |
| monophosphate | H | H | CH₃ | O | guanine |
| monophosphate | H | H | CH₃ | O | 6-(N,N-diacetyl)-adenine |
| monophosphate | H | H | CH₃ | O | 2-fluoroadenine |
| monophosphate | H | H | CH₃ | O | 8-fluoroadenine |
| monophosphate | H | H | CH₃ | O | 2,8-difluoro-adenine |
| monophosphate | H | H | CH₃ | O | adenine |
| monophosphate | H | H | CH₃ | S | 2-(N,N-diacetyl)-guanine |
| monophosphate | H | H | CH₃ | S | 6-O-acetyl guanine |
| monophosphate | H | H | CH₃ | S | 8-fluoroguanine |
| monophosphate | H | H | CH₃ | S | guanine |
| monophosphate | H | H | CH₃ | S | 6-(N,N-diacetyl)-adenine |
| monophosphate | H | H | CH₃ | S | 2-fluoroadenine |
| monophosphate | H | H | CH₃ | S | 8-fluoroadenine |
| monophosphate | H | H | CH₃ | S | 2,8-difluoro-adenine |
| monophosphate | H | H | CH₃ | S | adenine |
| diphosphate | H | H | CH₃ | O | 2-(N,N-diacetyl)-guanine |
| diphosphate | H | H | CH₃ | O | 6-O-acetyl guanine |
| diphosphate | H | H | CH₃ | O | 8-fluoroguanine |
| diphosphate | H | H | CH₃ | O | guanine |
| diphosphate | H | H | CH₃ | O | 6-(N,N-diacetyl)-adenine |
| diphosphate | H | H | CH₃ | O | 2-fluoroadenine |
| diphosphate | H | H | CH₃ | O | 8-fluoroadenine |
| diphosphate | H | H | CH₃ | O | 2,8-difluoro-adenine |
| diphosphate | H | H | CH₃ | O | adenine |
| diphosphate | H | H | CH₃ | S | 2-(N,N-diacetyl)-guanine |
| diphosphate | H | H | CH₃ | S | 6-O-acetyl guanine |
| diphosphate | H | H | CH₃ | S | 8-fluoroguanine |
| diphosphate | H | H | CH₃ | S | guanine |
| diphosphate | H | H | CH₃ | S | 6-(N,N-diacetyl)-adenine |
| diphosphate | H | H | CH₃ | S | 2-fluoroadenine |
| diphosphate | H | H | CH₃ | S | 8-fluoroadenine |
| diphosphate | H | H | CH₃ | S | 2,8-difluoro-adenine |
| diphosphate | H | H | CH₃ | S | adenine |
| triphosphate | H | H | CH₃ | O | 2-(N,N-diacetyl)-guanine |
| triphosphate | H | H | CH₃ | O | 6-O-acetyl guanine |
| triphosphate | H | H | CH₃ | O | 8-fluoroguanine |

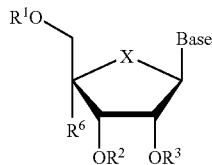

(III)

wherein:

| R¹ | R² | R³ | R⁶ | X | Base |
|---|---|---|---|---|---|
| triphosphate | H | H | CH₃ | O | guanine |
| triphosphate | H | H | CH₃ | O | 6-(N,N-diacetyl)-adenine |
| triphosphate | H | H | CH₃ | O | 2-fluoroadenine |
| triphosphate | H | H | CH₃ | O | 8-fluoroadenine |
| triphosphate | H | H | CH₃ | O | 2,8-difluoro-adenine |
| triphosphate | H | H | CH₃ | O | 2-(N,N-diacetyl)-guanine |
| triphosphate | H | H | CH₃ | S | 6-O-acetyl guanine |
| triphosphate | H | H | CH₃ | S | 8-fluoroguanine |
| triphosphate | H | H | CH₃ | S | guanine |
| triphosphate | H | H | CH₃ | S | 6-(N,N-diacetyl)-adenine |
| triphosphate | H | H | CH₃ | S | 2-fluoroadenine |
| triphosphate | H | H | CH₃ | S | 8-fluoroadenine |
| triphosphate | H | H | CH₃ | S | 2,8-difluoro-adenine |
| triphosphate | H | H | CH₃ | S | adenine |
| monophosphate | monophosphate | monophosphate | CF₃ | O | 2-(N,N-diacetyl)-guanine |
| monophosphate | monophosphate | monophosphate | CF₃ | O | 6-O-acetyl guanine |
| monophosphate | monophosphate | monophosphate | CF₃ | O | 8-fluoroguanine |
| monophosphate | monophosphate | monophosphate | CF₃ | O | guanine |
| monophosphate | monophosphate | monophosphate | CF₃ | O | 6-(N,N-diacetyl)-adenine |
| monophosphate | monophosphate | monophosphate | CF₃ | O | 2-fluoroadenine |
| monophosphate | monophosphate | monophosphate | CF₃ | O | 8-fluoroadenine |
| monophosphate | monophosphate | monophosphate | CF₃ | O | 2,8-difluoro-adenine |
| monophosphate | monophosphate | monophosphate | CF₃ | O | adenine |
| monophosphate | monophosphate | monophosphate | CF₃ | S | 2-(N,N-diacetyl)-guanine |
| monophosphate | monophosphate | monophosphate | CF₃ | S | 6-O-acetyl guanine |
| monophosphate | monophosphate | monophosphate | CF₃ | S | 8-fluoroguanine |
| monophosphate | monophosphate | monophosphate | CF₃ | S | guanine |
| monophosphate | monophosphate | monophosphate | CF₃ | S | 6-(N,N-diacetyl)-adenine |
| monophosphate | monophosphate | monophosphate | CF₃ | S | 2-fluoroadenine |
| monophosphate | monophosphate | monophosphate | CF₃ | S | 8-fluoroadenine |
| monophosphate | monophosphate | monophosphate | CF₃ | S | 2,8-difluoro-adenine |
| monophosphate | monophosphate | monophosphate | CF₃ | S | adenine |
| acetyl | acetyl | acetyl | CF₃ | O | guanine |
| acetyl | acetyl | acetyl | CF₃ | S | guanine |
| acetyl | acetyl | acetyl | 2-bromo-vinyl | O | guanine |
| acetyl | acetyl | acetyl | 2-bromo-vinyl | S | guanine |

Alternatively, the following nucleosides of Formula IV are prepared, using the appropriate sugar and pyrimidine or purine bases.

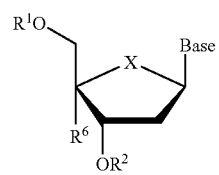

(IV)

| R¹ | R² | R⁶ | X | Base |
|---|---|---|---|---|
| wherein | | | | |
| H | H | CH₃ | O | 2,4-O-Diacetyluracil |
| H | H | CH₃ | O | Hypoxanthine |
| H | H | CH₃ | O | 2,4-O-Diacetylthymine |
| H | H | CH₃ | O | Thymine |
| H | H | CH₃ | O | Cytosine |
| H | H | CH₃ | O | 4-(N-mono-acetyl)cytosine |
| H | H | CH₃ | O | 4-(N,N-diacetyl)cytosine |
| H | H | CH₃ | O | Uracil |
| H | H | CH₃ | O | 5-Fluorouracil |
| H | H | CH₃ | S | 2,4-O-Diacetyluracil |
| H | H | CH₃ | S | Hypoxanthine |
| H | H | CH₃ | S | 2,4-O-Diacetylthymine |
| H | H | CH₃ | S | Thymine |
| H | H | CH₃ | S | Cytosine |
| H | H | CH₃ | S | 4-(N-mono-acetyl)cytosine |
| H | H | CH₃ | S | 4-(N,N-diacetyl)cytosine |
| H | H | CH₃ | S | Uracil |
| H | H | CH₃ | S | 5-Fluorouracil |
| mono-phosphate | H | CH₃ | O | 2,4-O-Diacetyluracil |
| mono-phosphate | H | CH₃ | O | Hypoxanthine |
| mono-phosphate | H | CH₃ | O | 2,4-O-Diacetylthymine |
| mono-phosphate | H | CH₃ | O | Thymine |
| mono-phosphate | H | CH₃ | O | Cytosine |
| mono-phosphate | H | CH₃ | O | 4-(N-mono-acetyl)cytosine |
| mono-phosphate | H | CH₃ | O | 4-(N,N-diacetyl)cytosine |
| mono-phosphate | H | CH₃ | O | Uracil |
| mono-phosphate | H | CH₃ | O | 5-Fluorouracil |
| mono-phosphate | H | CH₃ | S | 2,4-O-Diacetyluracil |
| mono-phosphate | H | CH₃ | S | Hypoxanthine |
| mono-phosphate | H | CH₃ | S | 2,4-O-Diacetylthymine |
| mono-phosphate | H | CH₃ | S | Thymine |
| mono-phosphate | H | CH₃ | S | Cytosine |
| mono-phosphate | H | CH₃ | S | 4-(N-mono-acetyl)cytosine |
| mono-phosphate | H | CH₃ | S | 4-(N,N-diacetyl)cytosine |
| mono-phosphate | H | CH₃ | S | Uracil |
| mono-phosphate | H | CH₃ | S | 5-Fluorouracil |
| diphos-phate | H | CH₃ | O | 2,4-O-Diacetyluracil |
| diphos-phate | H | CH₃ | O | Hypoxanthine |
| diphos-phate | H | CH₃ | O | 2,4-O-Diacetylthymine |
| diphos-phate | H | CH₃ | O | Thymine |

-continued

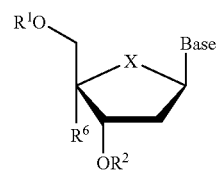

(IV)

| R¹ | R² | R⁶ | X | Base |
|---|---|---|---|---|
| wherein | | | | |
| diphos-phate | H | CH₃ | O | Cytosine |
| diphos-phate | H | CH₃ | O | 4-(N-mono-acetyl)cytosine |
| diphos-phate | H | CH₃ | O | 4-(N,N-diacetyl)cytosine |
| diphos-phate | H | CH₃ | O | Uracil |
| diphos-phate | H | CH₃ | O | 5-Fluorouracil |
| diphos-phate | H | CH₃ | S | 2,4-O-Diacetyluracil |
| diphos-phate | H | CH₃ | S | Hypoxanthine |
| diphos-phate | H | CH₃ | S | 2,4-O-Diacetylthymine |
| diphos-phate | H | CH₃ | S | Thymine |
| diphos-phate | H | CH₃ | S | Cytosine |
| diphos-phate | H | CH₃ | S | 4-(N-mono-acetyl)cytosine |
| diphos-phate | H | CH₃ | S | 4-(N,N-diacetyl)cytosine |
| diphos-phate | H | CH₃ | S | Uracil |
| diphos-phate | H | CH₃ | S | 5-Fluorouracil |
| triphos-phate | H | CH₃ | O | 2,4-O-Diacelyluracil |
| triphos-phate | H | CH₃ | O | Hypoxanthine |
| triphos-phate | H | CH₃ | O | 2,4-O-diacethylthymine |
| triphos-phate | H | CH₃ | O | Thymine |
| triphos-phate | H | CH₃ | O | Cytosine |
| triphos-phate | H | CH₃ | O | 4-(N-mono-acetyl)cytosine |
| triphos-phate | H | CH₃ | O | 4-(N,N-diacetyl)cytosine |
| triphos-phate | H | CH₃ | O | Uracil |
| triphos-phate | H | CH₃ | O | 5-Fluorouracil |
| triphos-phate | H | CH₃ | S | 2,4-O-Diacetyluracil |
| triphos-phate | H | CH₃ | S | Hypoxanthine |
| triphos-phate | H | CH₃ | S | 2,4-O-Diacetylthymine |
| triphos-phate | H | CH₃ | S | Thymine |
| triphos-phate | H | CH₃ | S | Cytosine |
| triphos-phate | H | CH₃ | S | 4-(N-mono-acetyl)cytosine |
| triphos-phate | H | CH₃ | S | 4-(N,N-diacetyl)cytosine |
| triphos-phate | H | CH₃ | S | Uracil |
| triphos-phate | H | CH₃ | S | 5-Fluorouracil |
| mono-phosphate | monophosphate | CF₃ | O | 2,4-O-Diacetyluracil |

-continued

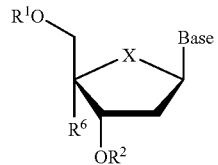

(IV)

wherein

| R¹ | R² | R⁶ | X | Base |
|---|---|---|---|---|
| monophosphate | monophosphate | CF₃ | O | Hypoxanthine |
| monophosphate | monophosphate | CF₃ | O | 2,4-O-Diacetylthymine |
| monophosphate | monophosphate | CF₃ | O | Thymine |
| monophosphate | monophosphate | CF₃ | O | Cytosine |
| monophosphate | monophosphate | CF₃ | O | 4-(N-mono-acetyl)cytosine |
| monophosphate | monophosphate | CF₃ | O | 4-(N,N-diacetyl)cytosine |
| monophosphate | monophosphate | CF₃ | O | Uracil |
| monophosphate | monophosphate | CF₃ | O | 5-Fluorouracil |
| monophosphate | monophosphate | CF₃ | S | 2,4-O-Diacetyluracil |
| monophosphate | monophosphate | CF₃ | S | Hypoxanthine |
| monophosphate | monophosphate | CF₃ | S | 2,4-O-Diacetylthymine |
| monophosphate | monophosphate | CF₃ | S | Thymine |
| monophosphate | monophosphate | CF₃ | S | Cyto sine |
| monophosphate | monophosphate | CF₃ | S | 4-(N-mono-acetyl)cytosine |
| monophosphate | monophosphate | CF₃ | S | 4-(N,N-diacetyl)cytosine |
| monophosphate | monophosphate | CF₃ | S | Uracil |
| monophosphate | monophosphate | CF₃ | S | 5-Fluorouracil |
| acetyl | acetyl | CF₃ | O | 4-(N,N-diacetyl)cytosine |
| acetyl | acetyl | CF₃ | S | 4-(N,N-diacetyl)cytosine |
| acetyl | acetyl | 2-bromo-vinyl | O | 4-(N,N-diacetyl)cytosine |
| acetyl | acetyl | 2-bromo-vinyl | S | 4-(N,N-diacetyl)cytosine |
| H | H | CH₃ | O | 2-(N,N-diacetyl)-guanine |
| H | H | CH₃ | O | 6-O-acetyl guanine |
| H | H | CH₃ | O | 8-fluoroguanine |
| H | H | CH₃ | O | guanine |
| H | H | CH₃ | O | 6-(N,N-diacetyl)-adenine |
| H | H | CH₃ | O | 2-fluoroadenine |
| H | H | CH₃ | O | 8-fluoroadenine |
| H | H | CH₃ | O | 2,6-difluoro-adenine |
| H | H | CH₃ | O | adenine |
| H | H | CH₃ | S | 2-(N,N-diacetyl)-guanine |
| H | H | CH₃ | S | 6-O-acetyl guanine |
| H | H | CH₃ | S | 8-fluoroguanine |
| H | H | CH₃ | S | guanine |
| H | H | CH₃ | S | 6-(N,N-diacetyl)-adenine |
| H | H | CH₃ | S | 2-fluoroadenine |
| H | H | CH₃ | S | 8-fluoroadenine |
| H | H | CH₃ | S | 2,6-difluoro-adenine |
| H | H | CH₃ | S | adenine |
| monophosphate | H | CH₃ | O | 2-(N,N-diacetyl)-guanine |
| monophosphate | H | CH₃ | O | 6-O-acetyl guanine |
| monophosphate | H | CH₃ | O | 8-fluoroguanine |
| monophosphate | H | CH₃ | O | guanine |
| monophosphate | H | CH₃ | O | 6-(N,N-diacetyl)-adenine |
| monophosphate | H | CH₃ | O | 2-fluoroadenine |
| monophosphate | H | CH₃ | O | 8-fluoroadenine |
| monophosphate | H | CH₃ | O | 2,6-difluoro-adenine |
| monophosphate | H | CH₃ | O | adenine |
| monophosphate | H | CH₃ | S | 2-(N,N-diacetyl)-guanine |
| monophosphate | H | CH₃ | S | 6-O-acetyl guanine |
| monophosphate | H | CH₃ | S | 8-fluoroguanine |
| monophosphate | H | CH₃ | S | guanine |
| monophosphate | H | CH₃ | S | 6-(N,N-diacetyl)-adenine |
| monophosphate | H | CH₃ | S | 2-fluoroadenine |
| monophosphate | H | CH₃ | S | 8-fluoroadenine |
| monophosphate | H | CH₃ | S | 2,6-difluoro-adenine |
| monophosphate | H | CH₃ | S | adenine |
| diphosphate | H | CH₃ | O | 2-(N,N-diacetyl)-guanine |
| diphosphate | H | CH₃ | O | 6-O-acetyl guanine |
| diphosphate | H | CH₃ | O | 8-fluoroguanine |
| diphosphate | H | CH₃ | O | guanine |
| diphosphate | H | CH₃ | O | 6-(N,N-diacetyl)-adenine |
| diphosphate | H | CH₃ | O | 2-fluoroadenine |
| diphosphate | H | CH₃ | O | 8-fluoroadenine |
| diphosphate | H | CH₃ | O | 2,6-difluoro-adenine |
| diphosphate | H | CH₃ | O | adenine |
| diphosphate | H | CH₃ | S | 2-(N,N-diacetyl)-guanine |
| diphosphate | H | CH₃ | S | 6-O-acetyl guanine |
| diphosphate | H | CH₃ | S | 8-fluoroguanine |
| diphosphate | H | CH₃ | S | guanine |
| diphosphate | H | CH₃ | S | 6-(N,N-diacetyl)-adenine |
| diphosphate | H | CH₃ | S | 2-fluoroadenine |
| diphosphate | H | CH₃ | S | 8-fluoroadenine |
| diphosphate | H | CH₃ | S | 2,6-difluoro-adenine |
| diphosphate | H | CH₃ | S | adenine |
| triphosphate | H | CH₃ | O | 2-(N,N-diacetyl)-guanine |

-continued

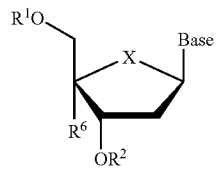

(IV)

wherein

| R$^1$ | R$^2$ | R$^6$ | X | Base |
|---|---|---|---|---|
| triphosphate | H | CH$_3$ | O | 6-O-acetyl guanine |
| triphosphate | H | CH$_3$ | O | 8-fluoroguanine |
| triphosphate | H | CH$_3$ | O | guanine |
| triphosphate | H | CH$_3$ | O | 6-(N,N-diacetyl)-adenine |
| triphosphate | H | CH$_3$ | O | 2-fluoroadenine |
| triphosphate | H | CH$_3$ | O | 8-fluoroadenine |
| triphosphate | H | CH$_3$ | O | 2,6-difluoro-adenine |
| triphosphate | H | CH$_3$ | O | adenine |
| triphosphate | H | CH$_3$ | S | 2-(N,N-diacetyl)-guanine |
| triphosphate | H | CH$_3$ | S | 6-O-acetyl guanine |
| triphosphate | H | CH$_3$ | S | 8-fluoroguanine |
| triphosphate | H | CH$_3$ | S | guanine |
| triphosphate | H | CH$_3$ | S | 6-(N,N-diacetyl)-adenine |
| triphosphate | H | CH$_3$ | S | 2-fluoroadenine |
| triphosphate | H | CH$_3$ | S | 8-fluoroadenine |
| triphosphate | H | CH$_3$ | S | 2,6-difluoro-adenine |
| triphosphate | H | CH$_3$ | S | adenine |
| monophosphate | monophosphate | CF$_3$ | O | 2-(N,N-diacetyl)-guanine |
| monophosphate | monophosphate | CF$_3$ | O | 6-O-acetyl guanine |
| monophosphate | monophosphate | CF$_3$ | O | 8-fluoroguanine |
| monophosphate | monophosphate | CF$_3$ | O | guanine |
| monophosphate | monophosphate | CF$_3$ | O | 6-(N,N-diacetyl)-adenine |
| monophosphate | monophosphate | CF$_3$ | O | 2-fluoroadenine |
| monophosphate | monophosphate | CF$_3$ | O | 8-fluoroadenine |
| monophosphate | monophosphate | CF$_3$ | O | 2,6-difluoro-adenine |
| monophosphate | monophosphate | CF$_3$ | O | adenine |
| monophosphate | monophosphate | CF$_3$ | S | 2-(N,N-diacetyl)-guanine |
| monophosphate | monophosphate | CF$_3$ | S | 6-O-acetyl guanine |
| monophosphate | monophosphate | CF$_3$ | S | 8-fluoroguanine |
| monophosphate | monophosphate | CF$_3$ | S | guanine |
| monophosphate | monophosphate | CF$_3$ | S | 6-(N,N-diacetyl)-adenine |
| monophosphate | monophosphate | CF$_3$ | S | 2-fluoroadenine |
| monophosphate | monophosphate | CF$_3$ | S | 8-fluoroadenine |
| monophosphate | monophosphate | CF$_3$ | S | 2,6-difluoro-adenine |
| monophosphate | monophosphate | CF$_3$ | S | adenine |
| acetyl | acetyl | CF$_3$ | O | guanine |
| acetyl | acetyl | CF$_3$ | S | guanine |
| acetyl | acetyl | 2-bromo-vinyl | O | guanine |
| acetyl | acetyl | 2-bromo-vinyl | S | guanine |

Alternatively, the following nucleosides of Formula V are prepared, using the appropriate sugar and pyrimidine or purine bases.

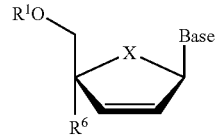

(V)

wherein:

| R$^1$ | R$^6$ | X | Base |
|---|---|---|---|
| H | CH$_3$ | O | 2,4-O-Diacetyluracil |
| H | CH$_3$ | O | Hypoxanthine |
| H | CH$_3$ | O | 2,4-O-Diacetylthymine |
| H | CH$_3$ | O | Thymine |
| H | CH$_3$ | O | Cytosine |
| H | CH$_3$ | O | 4-(N-mono-acetyl)cytosine |
| H | CH$_3$ | O | 4-(N,N-diacetyl)cytosine |
| H | CH$_3$ | O | Uracil |
| H | CH$_3$ | O | 5-Fluorouracil |
| H | CH$_3$ | S | 2,4-O-Diacetyluracil |
| H | CH$_3$ | S | Hypoxanthine |
| H | CH$_3$ | S | 2,4-O-Diacetylthymine |
| H | CH$_3$ | S | Thymine |
| H | CH$_3$ | S | Cytosine |
| H | CH$_3$ | S | 4-(N-mono-acetyl)cytosine |
| H | CH$_3$ | S | 4-(N,N-diacetyl)cytosine |
| H | CH$_3$ | S | Uracil |
| monophosphate | CH$_3$ | S | 4-(N-mono-acetyl)cytosine |
| monophosphate | CH$_3$ | S | 4-(N,N-diacetyl)cytosine |
| monophosphate | CH$_3$ | S | Uracil |
| monophosphate | CH$_3$ | S | 5-Fluorouracil |
| diphosphate | CH$_3$ | O | 2,4-O-Diacetyluracil |
| diphosphate | CH$_3$ | O | Hypoxanthine |
| diphosphate | CH$_3$ | O | 2,4-O-Diacetylthymine |
| diphosphate | CH$_3$ | O | Thymine |
| diphosphate | CH$_3$ | O | Cytosine |
| diphosphate | CH$_3$ | O | 4-(N-mono-acetyl)cytosine |
| diphosphate | CH$_3$ | O | 4-(N,N-diacetyl)cytosine |
| diphosphate | CH$_3$ | O | Uracil |
| diphosphate | CH$_3$ | O | 5-Fluorouracil |
| diphosphate | CH$_3$ | S | 2,4-O-Diacetyluracil |
| diphosphate | CH$_3$ | S | Hypoxanthine |
| diphosphate | CH$_3$ | S | 2,4-O-Diacetylthymine |
| diphosphate | CH$_3$ | S | Thymine |
| diphosphate | CH$_3$ | S | Cytosine |

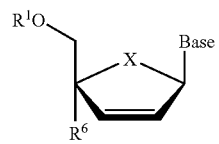

(V)

wherein:

| R¹ | R⁶ | X | Base |
|---|---|---|---|
| triphosphate | CH₃ | O | 2,4-O-Diacetyluracil |
| triphosphate | CH₃ | O | Hypoxanthine |
| triphosphate | CH₃ | O | 2,4-O-Diacetylthymine |
| triphosphate | CH₃ | O | Thymine |
| triphosphate | CH₃ | O | Cytosine |
| triphosphate | CH₃ | O | 4-(N-mono-acetyl)cytosine |
| triphosphate | CH₃ | O | 4-(N,N-diacetyl)cytosine |
| triphosphate | CH₃ | O | Uracil |
| triphosphate | CH₃ | O | 5-Fluorouracil |
| triphosphate | CH₃ | S | 2,4-O-Diacetyluracil |
| triphosphate | CH₃ | S | Hypoxanthine |
| triphosphate | CH₃ | S | 2,4-O-Diacetylthymine |
| triphosphate | CH₃ | S | Thymine |
| triphospahate | CH₃ | S | Cytosine |
| monophosphate | CF₃ | O | 2,4-O-Diacetyluracil |
| monophosphate | CF₃ | O | Hypoxanthine |
| monophosphate | CF₃ | O | 2,4-O-Diacetylthymine |
| monophosphate | CF₃ | O | Thymine |
| monophosphate | CF₃ | O | Cytosine |
| monophosphate | CF₃ | O | 4-(N-mono-acetyl)cytosine |
| monophosphate | CF₃ | O | 4-(N,N-diacetyl)cytosine |
| monophosphate | CF₃ | O | Uracil |
| monophosphate | CF₃ | O | 5-Fluorouracil |
| monophosphate | CF₃ | S | 2,4-O-Diacetyluracil |
| monophosphate | CF₃ | S | Hypoxanthine |
| monophosphate | CF₃ | S | 2,4-O-Diacetylthymine |
| monophosphate | CF₃ | S | Thymine |
| monophosphate | CF₃ | S | Cytosine |
| monophosphate | CF₃ | S | 4-(N-mono-acetyl)cytosine |
| monophosphate | CF₃ | S | 4-(N,N-diacetyl)cytosine |
| monophosphate | CF₃ | S | Uracil |
| monophosphate | CF₃ | S | 5-Fluorouracil |
| acetyl | CF₃ | O | 4-(N,N-diacetyl)cytosine |
| acetyl | CF₃ | S | 4-(N,N-diacetyl)cytosine |
| acetyl | 2-bromo-vinyl | O | 4-(N,N-diacetyl)cytosine |
| acetyl | 2-bromo-vinyl | S | 4-(N,N-diacetyl)cytosine |

Alternatively, the following nucleosides of Formula VI are prepared, using the appropriate sugar and pyrimidine or purine bases.

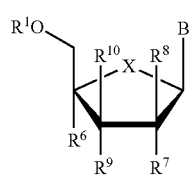

(VI)

wherein:

| R¹ | R⁶ | R⁷ | R⁸ | X | Base | R¹⁰ | R⁹ |
|---|---|---|---|---|---|---|---|
| H | CH₃ | H | H | O | 2,4-O-Diacetyluracil | OH | Me |
| H | CH₃ | H | H | O | Hypoxanthine | OH | Me |
| H | CH₃ | H | H | O | 2,4-O-Diacetylthymine | OH | Me |
| H | CH₃ | H | H | O | Thymine | OH | Me |
| H | CH₃ | H | H | O | Cytosine | OH | Me |
| H | CH₃ | H | H | O | 4-(N-mono-acetyl)cytosine | OH | Me |
| H | CH₃ | H | H | O | 4-(N,N-diacetyl)cytosine | OH | Me |
| H | CH₃ | H | H | O | Uracil | OH | Me |

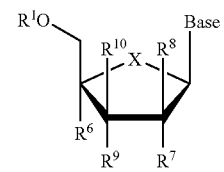

(VI)

wherein:

| R¹ | R⁶ | R⁷ | R⁸ | X | Base | R¹⁰ | R⁹ |
|---|---|---|---|---|---|---|---|
| H | CH₃ | H | H | O | 5-Fluorouracil | OH | Me |
| H | CH₃ | H | H | S | 2,4-O-Diacetyluracil | OH | Me |
| H | CH₃ | H | H | S | Hypoxanthine | OH | Me |
| H | CH₃ | H | H | S | 2,4-O-Diacetylthymine | OH | Me |
| H | CH₃ | H | H | S | Thymine | OH | Me |
| H | CH₃ | H | H | S | Cytosine | OH | Me |
| H | CH₃ | H | H | S | 4-(N-mono-acetyl)cytosine | OH | Me |
| H | CH₃ | H | H | S | 4-(N,N-diacetyl)cytosine | OH | Me |
| H | CH₃ | H | H | S | Uracil | OH | Me |
| H | CH₃ | H | H | S | 5-Fluorouracil | OH | Me |
| monophosphate | CH₃ | H | H | O | 2,4-O-Diacetyluracil | OH | Me |
| monophosphate | CH₃ | H | H | O | Hypoxanthine | OH | Me |
| monophosphate | CH₃ | H | H | O | 2,4-O-Diacetylthymine | OH | Me |
| monophosphate | CH₃ | H | H | O | Thymine | OH | Me |
| monophosphate | CH₃ | H | H | O | Cytosine | OH | Me |
| monophosphate | CH₃ | H | H | O | 4-(N-mono-acetyl)cytosine | OH | Me |
| monophosphate | CH₃ | H | H | O | 4-(N,N-diacetyl)cytosine | OH | Me |
| monophosphate | CH₃ | H | H | O | Uracil | OH | Me |
| monophosphate | CH₃ | H | H | O | 5-Fluorouracil | OH | Me |
| monophosphate | CH₃ | H | H | S | 2,4-O-Diacetyluracil | OH | Me |
| monophosphate | CH₃ | H | H | S | Hypoxanthine | OH | Me |
| monophosphate | CH₃ | H | H | S | 2,4-O-Diacetylthymine | OH | Me |
| monophosphate | CH₃ | H | H | S | Thymine | OH | Me |
| monophosphate | CH₃ | H | H | S | Cytosine | OH | Me |
| monophosphate | CH₃ | H | H | S | 4-(N-mono-acetyl)cytosine | OH | Me |
| monophosphate | CH₃ | H | H | S | 4-(N,N-diacetyl)cytosine | OH | Me |
| monophosphate | CH₃ | H | H | S | Uracil | OH | Me |
| monophosphate | CH₃ | H | H | S | 5-Fluorouracil | OH | Me |
| diphosphate | CH₃ | H | H | O | 2,4-O-Diacetyhiracil | OH | Me |
| diphosphate | CH₃ | H | H | O | Hypoxanthine | OH | Me |
| diphosphate | CH₃ | H | H | O | 2,4-O-Diacetylthymine | OH | Me |
| diphosphate | CH₃ | H | H | O | Thymine | OH | Me |
| diphosphate | CH₃ | H | H | O | Cytosine | OH | Me |
| diphosphate | CH₃ | H | H | O | 4-(N-mono-acetyl)cytosine | OH | Me |
| diphosphate | CH₃ | H | H | O | 4-(N,N-diacetyl)cytosine | OH | Me |
| diphosphate | CH₃ | H | H | O | Uracil | OH | Me |
| diphosphate | CH₃ | H | H | O | 5-Fluorouracil | OH | Me |
| diphosphate | CH₃ | H | H | S | 2,4-O-Diacetyluracil | OH | Me |

-continued

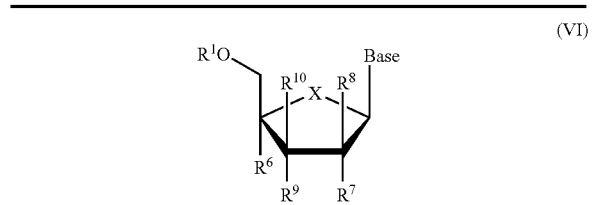

(VI)

wherein:

| R¹ | R⁶ | R⁷ | R⁸ | X | Base | R¹⁰ | R⁹ |
|---|---|---|---|---|---|---|---|
| phate diphosphate | CH₃ | H | H | S | Hypoxanthine | OH | Me |
| diphosphate | CH₃ | H | H | S | 2,4-O-Diacetylthymine | OH | Me |
| diphosphate | CH₃ | H | H | S | Thymine | OH | Me |
| diphosphate | CH₃ | H | H | S | Cytosine | OH | Me |
| triphosphate | CH₃ | H | H | O | 2,4-O-Diacetyluracil | OH | Me |
| triphosphate | CH₃ | H | H | O | Hypoxanthine | OH | Me |
| triphosphate | CH₃ | H | H | O | 2,4-O-Diacetylthymine | OH | Me |
| triphosphate | CH₃ | H | H | O | Thymine | OH | Me |
| triphosphate | CH₃ | H | H | O | Cytosine | OH | Me |
| triphosphate | CH₃ | H | H | O | 4-(N-mono-acetyl)cytosine | OH | Me |
| triphosphate | CH₃ | H | H | O | 4-(N,N-diacetyl)cytosine | OH | Me |
| triphosphate | CH₃ | H | H | O | Uracil | OH | Me |
| triphosphate | CH₃ | H | H | O | 5-Fluorouracil | OH | Me |
| triphosphate | CH₃ | H | H | S | 2,4-O-Diacetyluracil | OH | Me |
| triphosphate | CH₃ | H | H | S | Hypoxanthine | OH | Me |
| triphosphate | CH₃ | H | H | S | 2,4-O-Diacetylthymine | OH | Me |
| triphosphate | CH₃ | H | H | S | Thymine | OH | Me |
| triphosphate | CH₃ | H | H | S | Cytosine | OH | Me |
| monophosphate | CF₃ | H | H | O | 2,4-O-Diacetyluracil | OH | Me |
| monophosphate | CF₃ | H | H | O | Hypoxanthine | OH | Me |
| monophosphate | CF₃ | H | H | O | 2,4-O-Diacetylthymine | OH | Me |
| monophosphate | CF₃ | H | H | O | Thymine | OH | Me |
| monophosphate | CF₃ | H | H | O | Cytosine | OH | Me |
| monophosphate | CF₃ | H | H | O | 4-(N-mono-acetyl)cytosine | OH | Me |
| monophosphate | CF₃ | H | H | O | 4-(N,N-diacetyl)cytosine | OH | Me |
| monophosphate | CF₃ | H | H | O | Uracil | OH | Me |
| monophosphate | CF₃ | H | H | O | 5-Fluorouracil | OH | Me |
| monophosphate | CF₃ | H | H | S | 2,4-O-Diacetyluracil | OH | Me |
| monophosphate | CF₃ | H | H | S | Hypoxanthine | OH | Me |
| monophosphate | CF₃ | H | H | S | 2,4-O-Diacetylthymine | OH | Me |
| monophosphate | CF₃ | H | H | S | Thymine | OH | Me |
| monophosphate | CF₃ | H | H | S | Cytosine | OH | Me |
| monophosphate | CF₃ | H | H | S | 4-(N-mono-acetyl)cytosine | OH | Me |

-continued

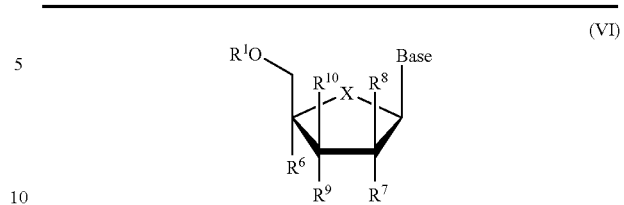

(VI)

wherein:

| R¹ | R⁶ | R⁷ | R⁸ | X | Base | R¹⁰ | R⁹ |
|---|---|---|---|---|---|---|---|
| monophosphate | CF₃ | H | H | S | 4-(N,N-diacetyl)cytosine | OH | Me |
| monophosphate | CF₃ | H | H | S | Uracil | OH | Me |
| monophosphate | CF₃ | H | H | S | 5-Fluorouracil | OH | Me |
| acetyl | CH₃ | H | H | O | 4-(N,N-diacetyl)cytosine | H | Br |
| acetyl | CH₃ | H | H | S | 4-(N,N-diacetyl)cytosine | H | Br |
| acetyl | CH₃ | OH | H | O | 4-(N,N-diacetyl)cytosine | H | Br |
| acetyl | CH₃ | OH | H | S | 4-(N,N-diacetyl)cytosine | H | Br |

VII. Anti-Hepatitis C Activity

Compounds can exhibit anti-hepatitis C activity by inhibiting HCV polymerase, by inhibiting other enzymes needed in the replication cycle, or by other pathways. A number of assays have been published to assess these activities. A general method that assesses the gross increase of HCV virus in culture is disclosed in U.S. Pat. No. 5,738,985 to Miles et al. In vitro assays have been reported in Ferrari et al., *Jnl. of Vir.*, 73:1649–1654, 1999; Ishii et al., *Hepatology*, 29:1227–1235,1999; Lohmann et al., *Jnl. of Bio. Chem.*, 274:10807–10815, 1999; and Yamashita et al, *Jnl. of Bio. Chem.*, 273:15479–15486, 1998.

WO 97/12033, filed on Sep. 27, 1996, by Emory University, listing C. Hagedorn and A. Reinoldus as inventors, and which claims priority to U.S. Ser. No. 60/004,383, filed on September 1995, describes an HCV polymerase assay that can be used to evaluate the activity of the compounds described herein. Another HCV polymerase assay has been reported by Bartholomeusz, et al., Hepatitis C virus (HCV) RNA polymerase assay using cloned HCV non-structural proteins; Antiviral Therapy 1996:1(Supp 4) 18–24.

Screens that measure reductions in kinase activity from HCV drugs are disclosed in U.S. Pat. No. 6,030,785, to Katze et al., U.S. Pat. No. 6,010,848 to Delvecchio et al, and U.S. Pat. No. 5,759,795 to Jubin et al. Screens that measure the protease inhibiting activity of proposed HCV drugs are disclosed in U.S. Pat. No. 5,861,267 to Su et al, U.S. Pat. No. 5,739,002 to De Francesco et al, and U.S. Pat. No. 5,597,691 to Houghton et al.

EXAMPLES

The test compounds were dissolved in DMSO at an initial concentration of 200 μM and then were serially diluted in culture medium.

Unless otherwise stated, baby hamster kidney (BHK-21) (ATCC CCL-10) and Bos Taurus (BT) (ATCC CRL 1390) cells were grown at 37° C. in a humidified $CO_2$ (5%) atmosphere. BHK-21 cells were passaged in Eagle MEM additioned of 2 mM L-glutamine, 10% fetal bovine serum (FBS, Gibco) and Earle's BSS adjusted to contain 1.5 g/L sodium bicarbonate and 0.1 mM non-essential amino acids. BT cells were passaged in Dulbecco's modified Eagle's medium with 4 mM L-glutamine and 10% horse serum (HS, Gibco), adjusted to contain 1.5 g/L sodium bicarbonate, 4.5 g/L glucose and 1.0 mM sodium pyruvate. The vaccine strain 17D (YFV-17D) (Stamaril®, Pasteur Merieux) and Bovine Viral Diarrhea virus (BVDV) (ATCC VR-534) were used to infect BHK and BT cells, respectively, in 75 cm$^2$ bottles. After a 3 day incubation period at 37° C., extensive cytopathic effect was observed. Cultures were freeze-thawed three times, cell debris were removed by centrifugation and the supernatant was aliquoted and stored at −70° C. YFV-17D and BVDV were titrated in BHK-21 and BT cells, respectively, that were grown to confluency in 24-well plates.

Example 22

Phosphorylation Assay of Nucleoside to Active Triphosphate

To determine the cellular metabolism of the compounds, HepG2 cells are obtained from the American Type Culture Collection (Rockville, Md.), and are grown in 225 cm$^2$ tissue culture flasks in minimal essential medium supplemented with non-essential amino acids, 1% penicillin-streptomycin. The medium is renewed every three days, and the cells are subcultured once a week. After detachment of the adherent monolayer with a 10 minute exposure to 30 mL of trypsin-EDTA and three consecutive washes with medium, confluent HepG2 cells are seeded at a density of 2.5×10$^6$ cells per well in a 6-well plate and exposed to 10 µM of [$^3$H] labeled active compound (500 dpm/pmol) for the specified time periods. The cells are maintained at 37° C. under a 5% $CO_2$ atmosphere. At the selected time points, the cells are washed three times with ice-cold phosphate-buffered saline (PBS). Intracellular active compound and its respective metabolites are extracted by incubating the cell pellet overnight at −20° C. with 60% methanol followed by extraction with an additional 20 µL of cold methanol for one hour in an ice bath. The extracts are then combined, dried under gentle filtered air flow and stored at −20° C. until HPLC analysis.

Example 23

Bioavailability Assay in Cynomolgus Monkeys

Within 1 week prior to the study initiation, the cynomolgus monkey is surgically implanted with a chronic venous catheter and subcutaneous venous access port (VAP) to facilitate blood collection and underwent a physical examination including hematology and serum chemistry evaluations and the body weight was recorded. Each monkey (six total) receives approximately 250 µCi of $^3$H activity with each dose of active compound at a dose level of 10 mg/kg at a dose concentration of 5 mg/mL, either via an intravenous bolus (3 monkeys, IV), or via oral gavage (3 monkeys, PO). Each dosing syringe is weighed before dosing to gravimetrically determine the quantity of formulation administered. Urine samples are collected via pan catch at the designated intervals (approximately 18–0 hours pre-dose, 0–4, 4–8 and 8–12 hours post-dosage) and processed. Blood samples are collected as well (pre-dose, 0.25, 0.5, 1, 2, 3, 6, 8, 12 and 24 hours post-dosage) via the chronic venous catheter and VAP or from a peripheral vessel if the chronic venous catheter procedure should not be possible. The blood and urine samples are analyzed for the maximum concentration ($C_{max}$), time when the maximum concentration is achieved ($T_{max}$), area under the curve (AUC), half life of the dosage concentration (T½), clearance (CL), steady state volume and distribution ($V_{ss}$) and bioavailability (F).

Example 24

Bone Marrow Toxicity Assay

Human bone marrow cells are collected from normal healthy volunteers and the mononuclear population are separated by Ficoll-Hypaque gradient centrifugation as described previously by Sommadossi J-P, Carlisle R. "Toxicity of 3'-azido-3'-deoxythymidine and 9-(1,3-dihydroxy-2-propoxymethyl)guanine for normal human hematopoietic progenitor cells in vitro" Antimicrobial Agents and Chemotherapy 1987; 31:452–454; and Sommadossi J-P, Schinazi R F, Chu C K, Xie M-Y. "Comparison of cytotoxicity of the (−)- and (+)-enantiomer of 2',3'-dideoxy-3'-thiacytidine in normal human bone marrow progenitor cells" Biochemical Pharmacology 1992; 44:1921–1925. The culture assays for CFU-GM and BFU-E are performed using a bilayer soft agar or methylcellulose method. Drugs are diluted in tissue culture medium and filtered. After 14 to 18 days at 37° C. in a humidified atmosphere of 5% $CO_2$ in air, colonies of greater than 50 cells are counted using an inverted microscope. The results are presented as the percent inhibition of colony formation in the presence of drug compared to solvent control cultures.

Example 25

Mitochondria Toxicity Assay

HepG2 cells are cultured in 12-well plates as described above and exposed to various concentrations of drugs as taught by Pan-Zhou X-R, Cui L, Zhou X-J, Sommadossi J-P, Darley-Usmer V M. "Differential effects of antiretroviral nucleoside analogs on mitochondrial function in HepG2 cells" Antimicrob Agents Chemother 2000; 44:496–503. Lactic acid levels in the culture medium after 4 day drug exposure are measured using a Boehringer lactic acid assay kit. Lactic acid levels are normalized by cell number as measured by hemocytometer count.

Example 26

Cytotoxicity Assay

Cells are seeded at a rate of between 5×10$^3$ and 5×10$^4$/well into 96-well plates in growth medium overnight at 37° C. in a humidified $CO_2$ (5%) atmosphere. New growth medium containing serial dilutions of the drugs is then added. After incubation for 4 days, cultures are fixed in 50% TCA and stained with sulforhodamineB. The optical density was read at 550 nm. The cytotoxic concentration was expressed as the concentration required to reduce the cell number by 50% ($CC_{50}$). The preliminary results are tabulated in the Table 1 below.

TABLE 1

| MDBK versus Human Hepatoma | |
|---|---|
| Compound | $CC_{50}$, µM MDBK |
| β-D-4'-$CH_3$-riboG | >250 |
| β-D-4'-$CH_3$-ribo-4-thioU | >250 |
| β-D-4'-$CH_3$-riboC | >250 |
| β-D-4'-$CH_3$-ribo-5-fluoroU | >167 |
| β-D-4'-$CH_3$-riboT | >250 |
| β-D-4'-$CH_3$-riboA | >250 |

This invention has been described with reference to its preferred embodiments. Variations and modifications of the invention, will be obvious to those skilled in the art from the foregoing detailed description of the invention.

What is claimed is:

1. A compound of Formula I:

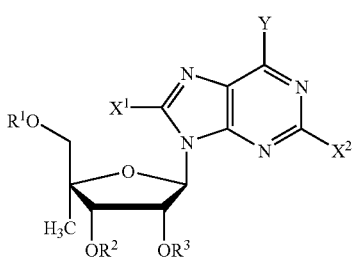

(I)

or a pharmaceutically acceptable salt or prodrug thereof, wherein:
- $R^1$ is alkyl; a, a phospholipid; an amino acid; a carbohydrate; a peptide; or cholesterol
- $R^2$ and $R^3$ are independently H, mono-phosphate, di-phosphate, tri-phosphate; a stabilized phosphate prodrug; acyl; alkyl; sulfonate ester; a phospholipid; an amino acid; a carbohydrate; a peptide; cholesterol; or other pharmaceutically acceptable leaving group that when administered in vivo provides a compound wherein $R^2$ and $R^3$ are independently H or phosphate;
- Y is hydrogen, bromo, chloro, fluoro, iodo, $OR^4$, $NR^4R^5$ or $SR^4$;
- $X^1$ and $X^2$ are independently selected from the group consisting of H, alkyl, CO-alkyl, CO-aryl, CO-alkoxyalkyl, chloro, bromo, fluoro, iodo, $OR^4$, $NR^4NR^5$ or $SR^4$; and
- $R^4$ and $R^5$ are independently hydrogen, acyl, or alkyl.

2. A compound of Formula II:

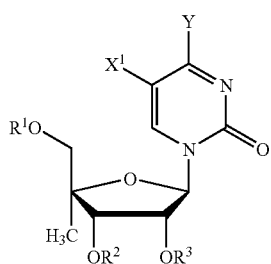

(II)

or a pharmaceutically acceptable salt or prodrug thereof, wherein:
- $R^1$ is alkyl; a phospholipid; an amino acid; a carbohydrate; a peptide; or cholesterol
- $R^2$ and $R^3$ are independently H, mono-phosphate, di-phosphate, tri-phosphate; a stabilized phosphate prodrug; acyl; alkyl; sulfonate ester; a phospholipid; an amino acid; a carbohydrate; a peptide; cholesterol; or other pharmaceutically acceptable leaving group that when administered in vivo provides a compound wherein $R^2$ and $R^3$ are independently H or phosnhate;
- Y is hydrogen, bromo, chloro, fluoro, iodo, $OR^4$, $NR^4R^5$ or $SR^4$;
- $X^1$ is selected from the group consisting of H, alkyl, CO-alkyl, CO-aryl, CO-alkoxyalkyl, chloro, bromo, fluoro, iodo, $OR^4$, $NR^4NR^5$ or $SR^4$; and
- $R^4$ and $R^5$ are independently hydrogen, acyl, or alkyl.

3. A compound of Formula III, IV or V, or a pharmaceutically acceptable salt or prodrug thereof, is provided:

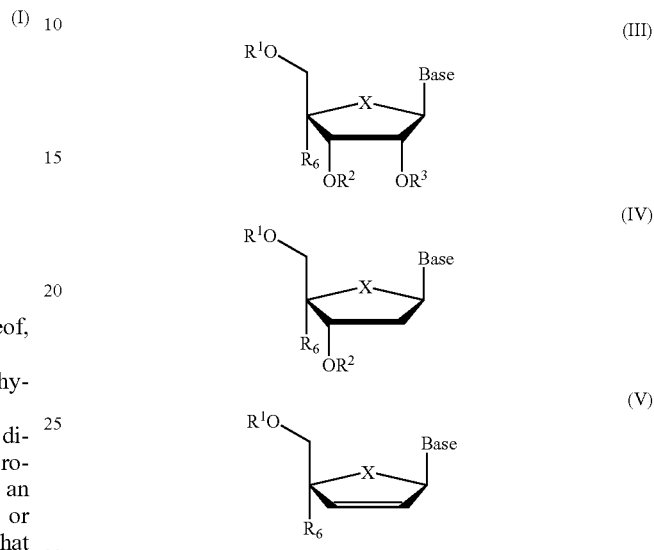

wherein:
- Base is a purine or pyrimidine base;
- $R^1$, $R^2$ and $R^3$ are independently H; mono-phosphate, di-phosphate, tri-phosphate, a stabilized phosphate prodrug; acyl; alkyl; sulfonate ester; a lipid, a phospholipid; an amino acid; a carbohydrate; a peptide; cholesterol; or other pharmaceutically acceptable leaving group that when administered in vivo provides a compound wherein $R^1$, $R^2$ or $R^3$ is independently H or phosphate;
- $R^6$ is hydroxy, Br-vinyl, —C(O)O(alkyl), —C(O)O(lower alkyl), —O(acyl), —O(lower acyl), —O(alkenyl), NH(acyl), —N(lower alkyl)$_2$, —N(acyl)$_2$; and
- X is O, S, SO$_2$ or CH$_2$.

4. A compound of Formula III, IV or V, or a pharmaceutically acceptable salt or prodrug thereof, is provided:

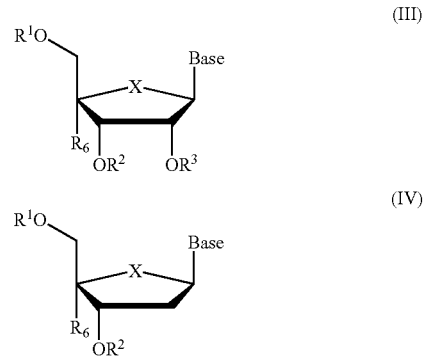

-continued

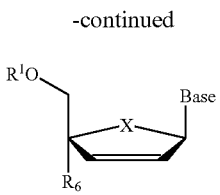
(V)

wherein:
Base is a purine or pyrimidine base;
$R^1$, $R^2$ and $R^3$ are independently hydrogen or phosphate;
$R^6$ is Br-vinyl; and
X is O, S, $SO_2$ or $CH_2$.

5. A compound of Formula III, IV or V, or a pharmaceutically acceptable salt or prodrug thereof, is provided:

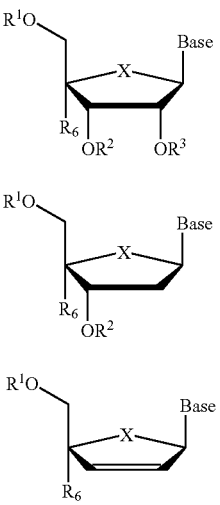
(III)
(IV)
(V)

wherein:
Base is a purine or pyrimidine base;
$R^1$, $R^2$ and $R^3$ are hydrogens;
$R^6$ is Br-vinyl; and
X is O, S, $SO_2$ or $CH_2$.

6. A compound of Formula III, IV or V, or a pharmaceutically acceptable salt or prodrug thereof, is provided:

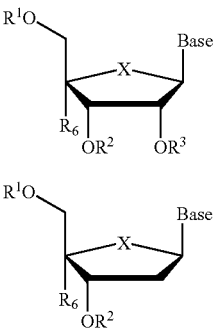
(III)
(IV)

-continued

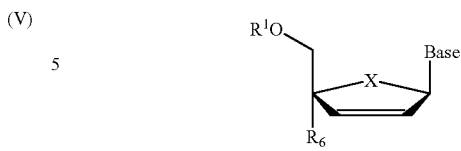
(V)

wherein:
Base is a purine or pyrimidine base;
$R^1$, $R^2$ and $R^3$ are independently hydrogen or phosphate;
$R^6$ is Br-vinyl; and
X is O.

7. A compound of Formula IV, or its pharmaceutically acceptable salt or prodrug, is provided:

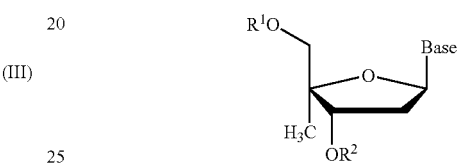
(IV)

wherein:
Base is a purine or pyrimidine base; optionally substituted with an amine or cyclopropyl; and
$R^1$ and $R^2$ are independently mono-phosphate, di-phosphate, tri-phosphate, a stabilized phosphate prodrug; sulfonate ester; a lipid, a phospholipid; an amino acid; a carbohydrate; a peptide; cholesterol; or other pharmaceutically acceptable leaving group that when administered in vivo provides a compound wherein $R^1$ or $R^2$ is independently H or phosphate.

8. A compound of Formula VI, or a pharmaceutically acceptable salt or prodrug thereof:

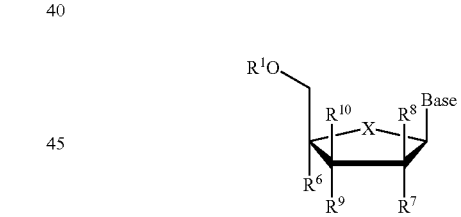
(VI)

wherein:
Base is a purine or pyrimidine base;
$R^1$ and $R^2$ are independently H; mono-phosphate, di-phosphate, tri-phosphate, a stabilized phosphate prodrug; acyl; alkyl; sulfonate ester; a lipid, a phospholipid; an amino acid; a carbohydrate; a peptide; cholesterol; or other pharmaceutically acceptable leaving group that when administered in vivo provides a compound wherein $R^1$ or $R^2$ independently H or phosphate;
$R^6$ is hydroxy, alkyl, azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;
$R^7$ and $R^9$ are independently $OR^2$, hydroxy, azido, cyano, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$;

$R^8$ is chlorine, bromine or iodine;

$R^{10}$ is H, alkyl, chlorine, bromine or iodine; and

X is O, S, $SO_2$ or $CH_2$.

9. A pharmaceutical composition for the treatment of a hepatitis C virus in a host, comprising an effective amount of a compound of Formula I:

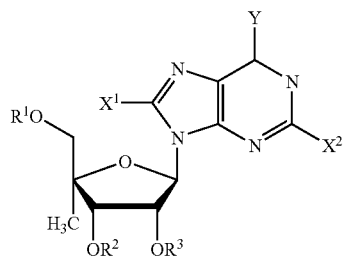

(I)

or a pharmaceutically acceptable salt or prodrug thereof, together with a pharmaceutically acceptable carrier or diluent, wherein:

$R^1$ is alkyl; a phospholipid; a carbohydrate; a peptide; an amino acid or cholesterol $R^2$ and $R^3$ are independently H, mono-phosphate, di-phosphate, tri-phosphate; a stabilized phosphate prodrug; acyl; alkyl; sulfonate ester; a lipid a phospholipid; an amino acid; a carbohydrate; a peptide; cholesterol; or other pharmaceutically acceptable leaving group that when administered in vivo provides a compound wherein $R^2$ and $R^3$ are independently H or phosphate;

Y is hydrogen, bromo, chloro, fluoro, iodo, $OR^4$, $NR^4R^5$ or $SR^4$;

$X^1$ and $X^2$ are independently selected from the group consisting of hydrogen, alkyl, CO-alkyl, CO-aryl, CO-alkoxyalkyl, chloro, bromo, fluoro, iodo, $OR^4$, $NR^4NR^5$ or $SR^4$; and $R^4$ and $R^5$ are independently hydrogen, acyl, or alkyl.

10. A pharmaceutical composition for the treatment of a hepatitis C virus in a host, comprising an effective amount of a compound of Formula II:

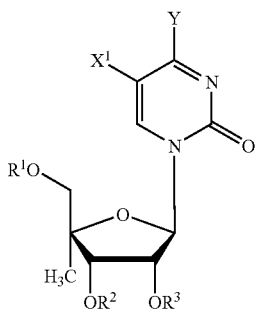

(II)

or a pharmaceutically acceptable salt or prodrug thereof, together with a pharmaceutically acceptable carrier or diluent, wherein:

$R^1$ is alkyl; a phospholipid; an amino acid; a carbohydrate; a peptide or cholesterol;

$R^2$ and $R^3$ are independently H, mono-phosphate, di-phosphate, tri-phosphate; a stabilized phosphate prodrug; acyl; alkyl; sulfonate ester; a lipid, a phospholipid; an amino acid; a carbohydrate; a peptide; cholesterol; or other pharmaceutically acceptable leaving group that when administered in vivo provides a compound wherein $R^2$ and $R^3$ are independently H or phosphate;

Y is hydrogen, bromo, chloro, fluoro, iodo, $OR^4$, $NR^4R^5$ or $SR^4$;

$X^1$ is selected from the group consisting of H, alkyl, CO-alkyl, CO-aryl, CO-alkoxyalkyl, chloro, bromo, fluoro, iodo, $OR^4$, $NR^4NR^5$ or $SR^4$; and $R^4$ and $R^5$ are independently hydrogen, acyl, or alkyl.

11. A pharmaceutical composition for the treatment of a hepatitis C virus in a host, comprising an effective amount of a compound selected from Formulas III, IV and V, or a pharmaceutically acceptable salt or prodrug thereof, is provided:

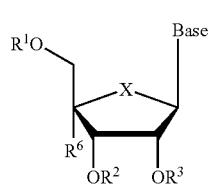

(III)

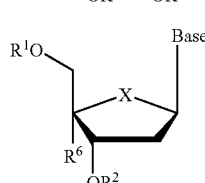

(IV)

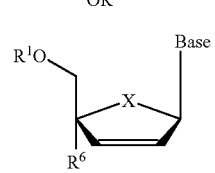

(V)

together with a pharmaceutically acceptable carrier or diluent, wherein:

Base is a purine or pyrimidine base;

$R^1$, $R^2$ and $R^3$ are independently H; mono-phosphate, di-phosphate, tri-phosphate, a stabilized phosphate prodrug; acyl; alkyl; sulfonate ester, a lipid, a phospholipid; an amino acid; a carbohydrate; a peptide; cholesterol; or other pharmaceutically acceptable leaving group that when administered in vivo provides a compound wherein $R^1$, $R^2$ or $R^3$ independently H or phosphate;

$R^6$ is hydroxy, Br-vinyl, —C(O)O(alkyl), —C(O)O(lower alkyl), —O(acyl), —O(lower acyl), —O(alkenyl), $NO_2$, $NH_2$, —NH(lower alkyl), —NH(acyl), —N(lower alkyl)$_2$, —N(acyl)$_2$; and X is O, S, $SO_2$ or $CH_2$.

12. A pharmaceutical composition for the treatment of a hepatitis C virus in a host, comprising an effective amount of a compound of Formula VI, or a pharmaceutically acceptable salt or prodrug thereof:

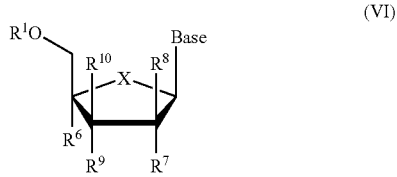

together with a pharmaceutically acceptable carrier or diluent, wherein:

Base is a purine or pyrimidine base;

$R^1$ and $R^2$ are independently H; mono-phosphate, di-phosphate, tri-phosphate, a stabilized phosphate prodrug; acyl; alkyl; sulfonate ester, a lipid, including a phospholipid; an amino acid; a carbohydrate; a peptide; cholesterol; or other pharmaceutically acceptable leaving group when administered in vivo provides a compound wherein $R^1$ or $R^2$ is independently H or phosphate;

$R^6$ is hydroxy, alkyl, azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;

$R^7$ and $R^9$ are independently $OR^2$, hydroxy, azido, cyano, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$;

$R^8$ is chlorine, bromine or iodine; —$R^{10}$ is H, alkyl, chlorine, bromine or iodine; and X is O, S, $SO_2$ or $CH_2$.

13. A pharmaceutical composition for the treatment of a hepatitis C virus in a host, comprising an effective amount of a compound of Formula I:

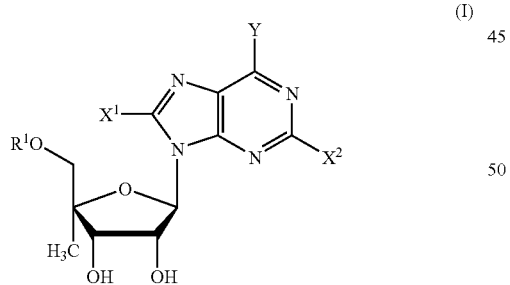

or a pharmaceutically acceptable salt or prodrug thereof, together with a pharmaceutically acceptable carrier or diluent, in combination with one or more other antivirally effective agents, wherein:

$R^1$ is alkyl; a phospholipid; an amino acid; a carbohydrate; a peptide; or cholesterol;

$R^2$ and $R^3$ are independently H, mono-phosphate, di-phosphate, tri-phosphate; a stabilized phosphate prodrug; acyl; alkyl; sulfonate ester; a lipid, a phospholipid; an amino acid; a carbohydrate; a peptide; cholesterol; or other pharmaceutically acceptable leaving group that when administered in vivo provides a compound wherein $R^2$ and $R^3$ are independently H or phosphate;

Y is hydrogen, bromo, chloro, fluoro, iodo, $OR^4$, $NR^4R^5$ or $SR^4$;

$X^1$ and $X^2$ are independently selected from the group consisting of H, alkyl, CO-alkyl, CO-aryl, CO-alkoxyalkyl, chloro, bromo, fluoro, iodo, $OR^4$, $NR^4NR^5$ or $SR^4$; and $R^4$ and $R^5$ are independently hydrogen, acyl, or alkyl.

14. A pharmaceutical composition for the treatment of a hepatitis C virus in a host, comprising an effective amount of a compound of Formula IV:

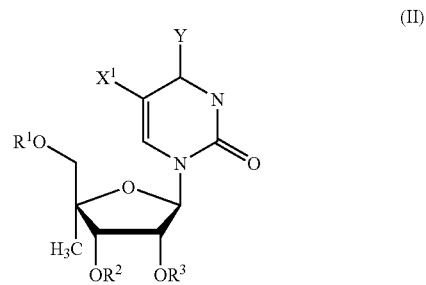

or a pharmaceutically acceptable salt or prodrug thereof, together with a pharmaceutically acceptable carrier or diluent, in combination with one or more other antivirally effective agents, wherein:

$R^1$ is alkyl; a phospholipid; an amino acid; a carbohydrate; a peptide; or cholesterol $R^2$ and $R^3$ are independently H, mono-phosphate, di-phosphate, tri-phosphate; a stabilized phosphate prodrug; acyl; alkyl; sulfonate ester; a lipid, a phospholipid; an amino acid; a carbohydrate; a peptide; a cholesterol; or other pharmaceutically acceptable leaving group that when administered in vivo provides a compound wherein $R^2$ and $R^3$ are independently H or phosphate;

Y is hydrogen, bromo, chloro, fluoro, iodo, $OR^4$, $NR^4R^5$ or $SR^4$;

$X^1$ is selected from the group consisting of H, alkyl, CO-alkyl, CO-aryl, CO-alkoxyalkyl, chloro, bromo, fluoro, iodo, $OR^4$, $NR^4NR^5$ or $SR^4$; and $R^4$ and $R^5$ are independently hydrogen, acyl, or alkyl.

15. A pharmaceutical composition for the treatment of a hepatitis C virus in a host, comprising an effective amount of a compound of Formula III, IV or V, or a pharmaceutically acceptable salt or prodrug thereof, is provided:

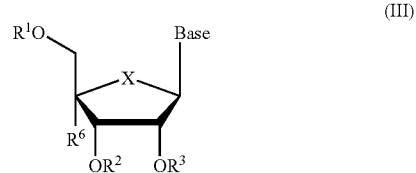

-continued

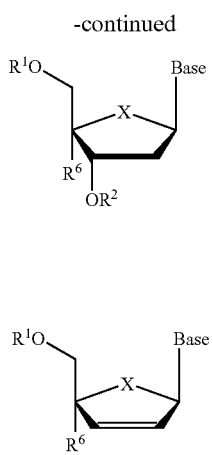
(IV)

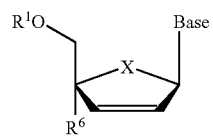
(V)

together with a pharmaceutically acceptable carrier or diluent, in combination with one or more other antivirally effective agents wherein:

Base is a purine or pyrimidine base;

$R^1$, $R^2$ and $R^3$ are independently H; phosphate monophosphate, di-phosphate, tr-iphosphate, a stabilized phosphate prodrug; acyl; alkyl; sulfonate ester, a lipid, a phospholipid; an amino acid; a carbohydrate; a peptide; cholesterol; or other pharmaceutically acceptable leaving group that when administered in vivo provides a compound wherein $R^{1, R2}$ or $R^3$ is independently H or phosphate;

$R^6$ is hydroxy Br-vinyl, —C(O)O(alkyl), —C(O)O(lower alkyl), —O(acyl), —O(lower acyl), —O(alkenyl), $NO_2$, $NH_2$, —NH(lower alkyl), —NH(acyl), —N(lower alkyl)$_2$, —N(acyl)$_2$; and X is O, S, $SO_2$ or $CH_2$.

16. A pharmaceutical composition for the treatment of a hepatitis C virus in a host, comprising an effective amount of a compound of Formula VI, or a pharmaceutically acceptable salt or prodrug thereof:

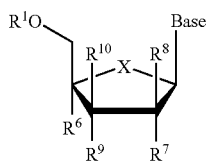
(VI)

together with a pharmaceutically acceptable carrier or diluent, in combination with one or more other antivirally effective agents wherein:

Base is a purine or pyrimidine base;

$R^1$ and $R^2$ are independently H; phosphate mono-phosphate, di-phosphate, tri-phosphate, a stabilized phosphate prodrug; acyl; alkyl; sulfonate ester; a lipid, a phospholipid; an amino acid; a carbohydrate; a peptide; cholesterol; or other pharmaceutically acceptable leaving group that when administered in vivo provides a compound wherein $R^1$ or $R^2$ independently H or phosphate;

$R^6$ is hydroxy, alkyl, azido, cyano, alkenyl, alkynyl, Br-vinyl, —C(O)O(alkyl), —C(O)O(lower alkyl), —O(acyl), —O(lower acyl), —O(alkyl), —O(lower alkyl), —O(alkenyl), chloro, bromo, fluoro, iodo, $NO_2$, $NH_2$, —NH(lower alkyl), —NH(acyl), —N(lower alkyl)$_2$, —N(acyl)$_2$;

$R^7$ and $R^9$ are independently $OR^2$, hydroxy, azido, cyano, Br-vinyl, —C(O)O(alkyl), —C(O)O(lower alkyl), —O(acyl), —O(lower acyl), —O(alkyl), —O(lower alkyl), —O(alkenyl), chlorine, bromine, iodine, $NO_2$, $NH_2$, —NH(lower alkyl), —NH(acyl), —N(lower alkyl)$_2$, —N(acyl)$_2$;

$R^8$ is chlorine, bromine or iodine;

$R^{10}$ is H, alkyl, chlorine, bromine or iodine; and

X is O, S, $SO_2$ or $CH_2$.

17. The compound as described in any of the preceding claims 1–8, wherein the said compound is in the form of a dosage unit.

18. The compound as described in claim 17, wherein the dosage unit contains 10 to 1500 mg of said compound.

19. The compound as described in claim 17 or 18, wherein said dosage unit is a tablet or capsule.

20. A compound as in claims 3, 4, 5, 6, 7, or 8, in which the purine or pyrimidine base is selected from the group consisting of

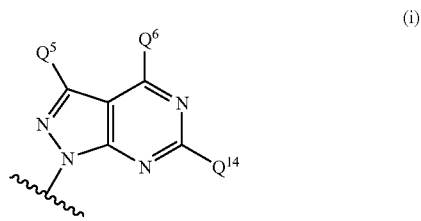
(i)

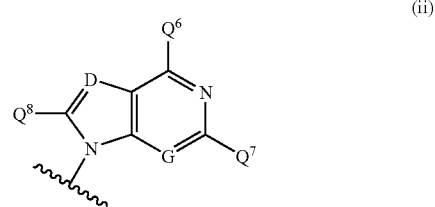
(ii)

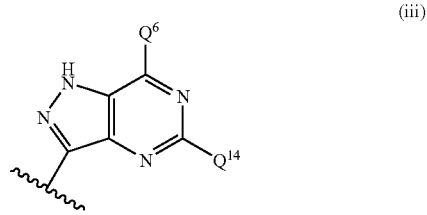
(iii)

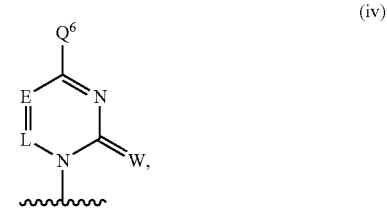
(iv)

-continued

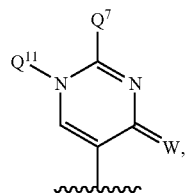
(v)

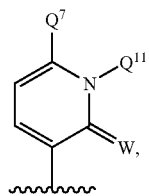
(vi)

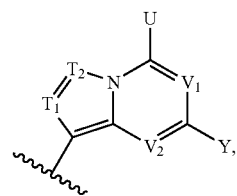
(A)

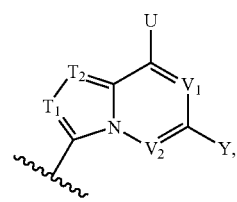
(B)

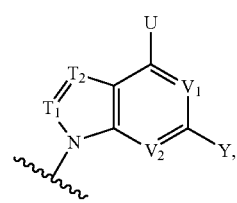
(C)

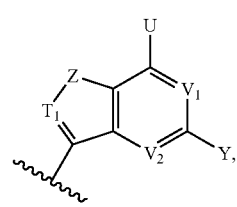
(D)

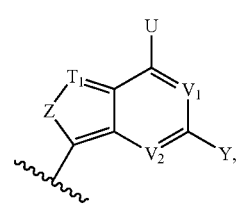
(E)

wherein, and L are each independently CH or N;

D is N, CH, C—CN, C—NO$_2$, C—C$_{1-3}$ alkyl, C—NH-CONH$_2$, C—CONQ$^{11}$Q$^{11}$, C—CSNQ$^{11}$Q$^{11}$, CCOOQ$^{11}$, C—C(=NH)NH$_2$, C-hydroxy, C—C$_{1-3}$alkoxy, C-amino, C—C$_{1-4}$ alkylamino, C—di(C$_{1-4}$ alkyl)amino, C-halogen, C—(1,3-oxazol-2-yl), C—(1,3-thiazol-2-yl), or C—(imidazol-2-yl); wherein alkyl is unsubstituted or substituted with one to three groups independently selected from halogen, amino, hydroxy, carboxy, and C$_{1-3}$ alkoxy;

E is N or CQ$^5$;

W is O, S, or NR;

R is H, OH, alkyl;

Q$^5$ is H, C$_{1-6}$ alkyl, C$_{2-6}$ alkenyl, C$_{2-6}$ alkynyl, C$_{1-4}$ alkylamino, CF$_3$, halogen, N, CN, NO$_2$, NHCONH$_2$, CONQ$^{11}$Q$^{11}$, CSNQ$^{11}$Q$^{11}$, COOQ$^{11}$, C(=NH)NH$_2$, hydroxy, C$_{1-3}$alkoxy, amino, C$_{1-4}$ alkylamino, di(C$_{1-4}$ alkyl) amino, halogen, 1,3-oxazol-2-yl, 1,3-thiazol-2-yl, or imidazol-2-yl; wherein alkyl is unsubstituted or substituted with one to three groups independently selected from halogen, amino, hydroxy, carboxy, and C$_{1-3}$ alkoxy;

Q$^6$ is H, OH, SH, NH$_2$, C$_{1-4}$ alkylamino, di(C$_{1-4}$ alkyl) amino, C$_{3-6}$ cycloalkylamino, halogen, C$_{1-4}$ alkyl, C$_{1-4}$ alkoxy, or CF$_3$;

Q$^7$ and Q$^{14}$ are each independently selected from the group consisting of H, CF$_3$, OH, SH, OR, SR C$_{1-4}$ alkyl, amino, C$_{1-4}$ alkylamino, C$_{3-6}$ cycloalkylanilno, and di(C$_{1-4}$alkyl)amino;

Q$^{11}$ is independently H or C$_{1-6}$ alkyl;

Q$^8$ is H, halogen, CN, carboxy, C$_{1-4}$ alkyloxycarbonyl, N$_3$, amino, C$_{1-4}$ alkylaniino, di(C$_{1-4}$ alkyl)amino, hydroxy, C$_{1-6}$ alkoxy, C$_{1-6}$ alkylthio, C$_{1-6}$ alkylsulfonyl, (C$_{1-4}$ alkyl)0-2 aminomethyl, N, CN, NO$_2$, C$_{1-3}$ alkyl, NHCONH$_2$, CONQ$^{11}$Q$^{11}$, CSNQ$^{11}$Q$^{11}$, COOQ$^{11}$, C(=NH)NH$_2$, 1,3-oxazol-2-yl, 1,3-thiazol-2-yl, or imidazol-2-yl, wherein alkyl is unsubstituted or substituted with one to three groups independently selected from halogen, amino, hydroxy, carboxy, and C$_{1-3}$ alkoxy.

21. A compound as in claims 3, 4, 5, 6, 7, or 8, in which the purine or pyrimidine base is selected from the group consisting of:

wherein:

T$_1$ and T$_2$ are independently selected from N, CH, or C-Q$^{16}$;

Q$^{16}$, U, and Y are independently selected from O, H, OH, substituted or unsubstituted alkyl, substituted or unsubstituted alkenyl, substituted or unsubstituted alkynyl, cycloalkyl, CO-alkyl, CO-aryl, CO-alkoxyalkyl, chloro, bromo, fluoro, iodo, OR$^4$, NR$^4$R$^5$ or SR$^5$, Br-vinyl, —O-alkyl, —O-alkenyl, —O-alkynyl, —O-aryl, —O-aralkyl, —O-acyl, —O-cycloalkyl, NH$_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, CN, N$_3$, COOH, CONH$_2$, CO$_2$-alkyl, CONH-alkyl, CON-dialkyl, OH, CF$_3$, CH$_2$OH, (CH$_2$)$_m$OH, (CH$_2$)$_m$NH$_2$, (CH$_2$)$_m$COOH, (CH$_2$)$_m$CN, (CH$_2$)$_m$NO$_2$, (CH$_2$)$_m$CONH$_2$, C$_{1-4}$ alkylamino, di(C$_{1-4}$ alkyl) amino, C$_{3-6}$ cycloalkylamino, C$_{1-4}$ alkoxy, C$_{1-4}$ alkoxycarbonyl, C$_{1-6}$ alkylthio, C$_{1-6}$ alkylsulfonyl, (C$_{1-4}$ alkyl)$_{0-2}$ aminomethyl, or -NHC(=NH)NH$_2$;

R$^4$ and R$^5$ are independently selected from hydrogen, acyl, or alkyl;

m is 0–10;

Z is S, SO, SO2, C=O, or NQ$^{20}$;

$Q^{20}$ is H or alkyl; and $V_1$ and $V_2$ are independently selected from CH or N.

22. A compound as in claims 3, 4, 5, 6, 7, or 8, in which the purine or pyrimidine base is selected from the group consiting of:

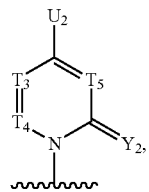
(F)

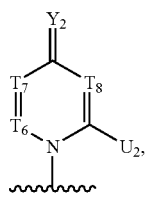
(G)

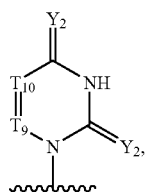
(H)

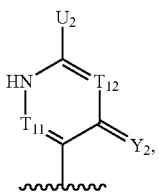
(I)

wherein:

$T_3$ and $T_4$ are independently selected from N or $CQ^{22}$;

$Q^{22}$ is independently selected from O, H, OH, substituted or unsubstituted alkyl, substituted or unsubstituted alkenyl, substituted or unsubstituted alkynyl, cycloalkyl, CO-alkyl, CO-aryl, CO-alkoxyalkyl, chloro, bromo, fluoro, iodo, $OR^4$, $NR^4R^5$ or $SR^5$, Br-vinyl,—O-alkyl, —O-alkenyl, —O-alkynyl, —O-aryl, —O-aralkyl, —O-acyl, —O-cycloalkyl, $NH_2$, NH-alkyl, N-dialkyl, NH-acyl, N-aryl, N-aralkyl, NH-cycloalkyl, SH, S-alkyl, S-acyl, S-aryl, S-cycloalkyl, S-aralkyl, CN, $N_3$, COOGH, $CONH_2$, $CO_2$-alkyl, CONH-alkyl, CON-dialkyl, OH, $CF_3$, $CH_2OH$, $(CH_2)_mOH$, $(CH_2)_mNH_2$, $(CH_2)_mCOOH$, $(CH_2)_mCN$, $(CH_2)_mNO_2$, $(CH_2)_mCONH_2$, $C_{1-4}$ alkylamino, di($C_{1-4}$ alkyl)amino, $C_{3-6}$ cycloalkylamino, $C_{1-4}$ alkoxy, $C_{1-4}$ alkoxycarbonyl, $C_{1-6}$ alkylthio, $C_{1-6}$ alkylsulfonyl, $(C_{1-4}$ alkyl$)_{0-2}$ aminomethyl, or —NHC(=NH)$NH_2$;

$R^4$ and $R^5$ are independently selected from hydrogen, acyl, or alkyl;

m is 0–10;

$T_5$, $T_6$, $T_7$, $T_8$, $T_9$, $T_{10}$, $T_{11}$, and $T_{12}$ are independently selected from N or CH;

$U_2$ is H, straight chained, branched or cyclic alkyl, CO-alkyl, CO-aryl, CO-alkoxyalkyl, chloro, bromo, fluoro, iodo, $OR^4$, $NR^4R^5$ or $SR^5$;

$Y^2$ is O, S, NH, NR or $CQ^{24}Q^{26}$ where R is H, OH, or alkyl;

$Q^{24}$ and $Q^{26}$ are independently selected from H, alkyl, straight chained, branched or cyclic alkyl, CO-alkyl, CO-aryl, CO-alkoxyalkyl, chloro, bromo, fluoro, iodo, $OR^4$, $NR^4R^5$ or $SR^5$.

23. The pharmaceutical composition as described in any of the preceding claims 9 12 and 13 16, wherein the said compound is in the form of a dosage unit.

24. The pharmaceutical composition as described in claim 23, wherein the dosage unit contains 10 to 1500 mg of said compound.

25. The pharmaceutical composition as described in claim 23, wherein said dosage unit is a tablet or capsule.

26. A compound of Formula I:

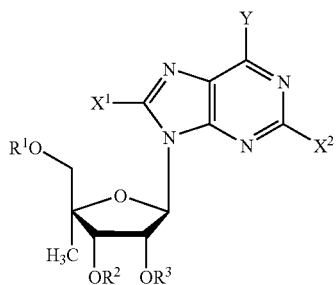
(I)

or a pharmaceutically acceptable salt or prodrug thereof, wherein:

$R^1$ H, mono-phosphate, di-phosphate, tri-phosphate; a stabilized phosphate prodrug; acyl; alkyl; sulfonate ester; a lipid, a phospholipid; an amino acid; a carbohydrate; a peptide; cholesterol ; or other pharmaceutically acceptable leaving group that when administered in vivo provides a compound wherein $R^1$ is independently H or phosphate;

$R^2$ and $R^3$ are independently mono-phosphate, di-phosphate, tri-phosphate; a stabilized phosphate prodrug; a lipid, a phospholipid; a carbohydrate; a peptide; cholesterol; or other pharmaceutically acceptable leaving group that when administered in vivo provides a compound wherein $R^2$ and $R^3$ are phosphate;

Y is hydrogen, bromo, chloro, fluoro, iodo, $OR^4$, $NR^4R^5$ or $SR^4$;

$X^1$ and $X^2$ are independently selected from the group consisting of H, alkyl, CO-alkyl, CO-aryl, CO-alkoxyalkyl, chloro, bromo, fluoro, iodo, $OR^4$, $NR^4NR^5$ or $SR^4$; and $R^4$ and $R^5$ are independently hydrogen, acyl, or alkyl.

27. A compound of Formula II:

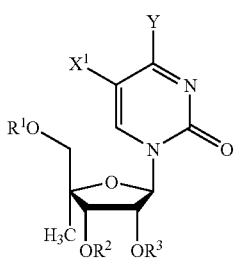
(II)

or a pharmaceutically acceptable salt or prodrug thereof, wherein:

- $R^1$ is H, mono-phosphate, di-phosphate, tri-phosphate; a stabilized phosphate prodrug; acyl; alkyl; sulfonate ester; a lipid, a phospholipid; an amino acid; a carbohydrate; a peptide; cholesterol; or other pharmaceutically acceptable leaving group that when administered in vivo provides a compound wherein $R^1$ is H or phosphate;
- $R^2$ and $R^3$ are independently mono-phosphate, di-phosphate, tri-phosphate; a stabilized phosphate prodrug; a lipid, a phospholipid; a carbohydrate; a peptide; cholesterol; or other pharmaceutically acceptable leaving group that when administered in vivo provides a compound wherein $R^2$ and $R^3$ are phosphate;
- Y is hydrogen, bromo, chloro, fluoro, iodo, $OR^4$, $NR^4R^5$ or $SR^4$;
- $X^1$ is selected from the group consisting of H, alkyl, CO-alkyl, CO-aryl, CO-alkoxyalkyl, chloro, bromo, fluoro, iodo, $OR^4$, $NR^4NR^5$ or $SR^4$; and
- $R^4$ and $R^5$ are independently hydrogen, acyl, or alkyl.

28. A pharmaceutical composition for the treatment of a hepatitis C virus in a host, comprising an effective amount of a compound of Formula I:

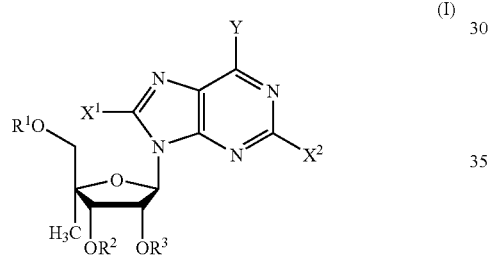

(I)

or a pharmaceutically acceptable salt or prodrug thereof, together with a pharmaceutically acceptable carrier or diluent, wherein:

- $R^1$ is H, mono-phosphate, di-phosphate, tri-phosphate; a stabilized phosphate prodrug; acyl; alkyl; sulfonate ester; a lipid, a phospholipid; an amino acid; a carbohydrate; a peptide; cholesterol; or other pharmaceutically acceptable leaving group that when administered in vivo provides a compound wherein $R^1$ is independently H or phosphate;
- $R^2$ and $R^3$ are independently mono-phosphate, di-phosphate, tri-phosphate; a stabilized phosphate prodrug; a lipid, a phospholipid; a carbohydrate; a peptide; a cholesterol; or other pharmaceutically acceptable leaving group that when administered in vivo provides a compound wherein $R^2$ and $R^3$ are phosphate;
- Y is hydrogen, bromo, chloro, fluoro, iodo, $OR^4$, $NR^4R^5$ or $SR^4$;
- $X^1$ and $X^2$ are independently selected from the group consisting of H, alkyl, CO-alkyl, CO-aryl, CO-alkoxyalkyl, chloro, bromo, fluoro, iodo, $OR^4$, $NR^4NR^5$ or $SR^4$; and
- $R^4$ and $R^5$ are independently hydrogen, acyl, or alkyl.

29. A pharmaceutical composition for the treatment of a hepatitis C virus in a host, comprising an effective amount of a compound of Formula II:

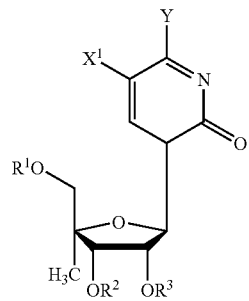

(II)

or a pharmaceutically acceptable salt or prodrug thereof, together with a pharmaceutically acceptable carrier or diluent, wherein:

- $R^1$ is H, mono-phosphate, di-phosphate, tri-phosphate; a stabilized phosphate prodrug; acyl; alkyl; sulfonate ester; a lipid, a phospholipid; an amino acid; a carbohydrate; a peptide; cholesterol; or other pharmaceutically acceptable leaving group that when administered in vivo provides a compound wherein $R^1$ is H or phosphate;
- $R^2$ and $R^3$ are independently mono-phosphate, di-phosphate, tri-phosphate; a stabilized phosphate prodrug; a lipid, a phospholipid; a carbohydrate; a peptide; cholesterol; or other pharmaceutically acceptable leaving group that when administered in vivo provides a compound wherein $R^2$ and $R^3$ are phosphate;
- Y is hydrogen, bromo, chloro, fluoro, iodo, $OR^4$, $NR^4R^5$ or $SR^4$;
- $X^1$ is selected from the group consisting of H, alkyl, CO-alkyl, CO-aryl, CO-alkoxyalkyl, chloro, bromo, fluoro, iodo, $OR^4$, $NR^4NR^5$ or $SR^4$; and
- $R^4$ and $R^5$ are independently hydrogen, acyl, or alkyl.

30. A pharmaceutical composition for the treatment of a hepatitis C virus in a host, comprising an effective amount of a compound of Formula I:

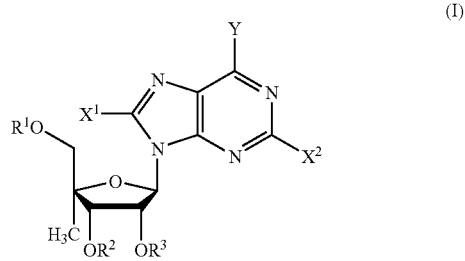

(I)

or a pharmaceutically acceptable salt or prodrug thereof, together with a pharmaceutically acceptable carrier or diluent, in combination with one or more other antivirally effective agents, wherein:

- $R^1$ is H, mono-phosphate, di-phosphate, tri-phosphate; a stabilized phosphate prodrug; acyl; alkyl; sulfonate ester; a lipid, a phospholipid; an amino acid; a carbohydrate; a peptide; cholesterol; or other pharmaceutically acceptable leaving group that when administered in vivo provides a compound wherein $R^1$ is independently H or phosphate;
- $R^2$ and $R^3$ are independently mono-phosphate, di-phosphate, tri-phosphate; a stabilized phosphate prodrug; a lipid, a phospholipid; a carbohydrate; a peptide; cholesterol; or other pharmaceutically acceptable leaving group that when administered in vivo provides a compound wherein $R^2$ and $R^3$ are phosphate;

Y is hydrogen, bromo, chloro, fluoro, iodo, $OR^4$, $NR^4R^5$ or $SR^4$;

$X^1$ and $X^2$ are independently selected from the group consisting of H, alkyl, CO-alkyl, CO-aryl, CO-alkoxyalkyl, chloro, bromo, fluoro, iodo, $OR^4$, $NR^4NR^5$ or $SR^4$; and $R^4$ and $R^5$ are independently hydrogen, acyl, or alkyl.

31. A pharmaceutical composition for the treatment of a hepatitis C virus in a host, comprising an effective amount of a compound of Formula II:

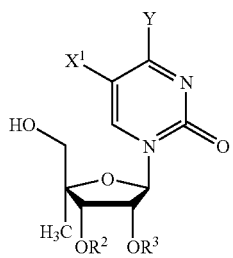

(II)

or a pharmaceutically acceptable salt or prodrug thereof, together with a pharmaceutically acceptable carrier or diluent, in combination with one or more other antivirally effective agents, wherein:

$R^1$ is H, mono-phosphate, di-phosphate, tri-phosphate; a stabilized phosphate prodrug; acyl; alkyl; sulfonate ester; a lipid, a phospholipid; an amino acid; a carbohydrate; a peptide; cholesterol; or other pharmaceutically acceptable leaving group that when administered in vivo provides a compound wherein $R^1$ is H or phosphate;

$R^2$ and $R^3$ are independently mono-phosphate, di-phosphate, tri-phosphate; a stabilized phosphate prodrug; a lipid, a phospholipid; a carbohydrate; a peptide; cholesterol; or other pharmaceutically acceptable leaving group that when administered in vivo provides a compound wherein $R^2$ and $R^3$ are phosphate;

Y is hydrogen, bromo, chloro, fluoro, iodo, $OR^4$, $NR^4R^5$ or $SR^4$;

$X^1$ is selected from the group consisting of H, alkyl, CO-alkyl, CO-aryl, CO-alkoxyalkyl, chloro, bromo, fluoro, iodo, $OR^4$, $NR^4NR^5$ or $SR^4$; and $R^4$ and $R^5$ are independently hydrogen, acyl, or alkyl.

\* \* \* \* \*